United States Patent
Verbeck, IV

(10) Patent No.: US 11,703,490 B2
(45) Date of Patent: *Jul. 18, 2023

(54) DYNAMIC REVERSE GAS STACK MODEL FOR PORTABLE CHEMICAL DETECTION DEVICES TO LOCATE THREAT AND POINT-OF-SOURCE FROM EFFLUENT STREAMS

(71) Applicant: University of North Texas, Denton, TX (US)

(72) Inventor: Guido Fridolin Verbeck, IV, Lewisville, TX (US)

(73) Assignee: University of North Texas, Denton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,323

(22) Filed: Feb. 28, 2022

(65) Prior Publication Data

US 2022/0187264 A1 Jun. 16, 2022

Related U.S. Application Data

(63) Continuation of application No. 15/769,265, filed as application No. PCT/US2016/056601 on Oct. 12, 2016, now Pat. No. 11,287,407.

(Continued)

(51) Int. Cl.
*G01N 33/00* (2006.01)
*G01N 21/3504* (2014.01)
(Continued)

(52) U.S. Cl.
CPC ........... *G01N 33/0036* (2013.01); *G01N 1/22* (2013.01); *G01N 1/26* (2013.01); *G01N 21/3504* (2013.01);
(Continued)

(58) Field of Classification Search
CPC .......... G01N 1/2273; G01N 2001/021; G01N 2001/0221; G01N 21/3504; G01N 33/0075
See application file for complete search history.

(56) References Cited

U.S. PATENT DOCUMENTS 4,736,316 A 4/1988 Wallman
6,287,765 B1 9/2001 Cubicciotti
(Continued)

FOREIGN PATENT DOCUMENTS

CN 201166661 Y 12/2008
CN 101833591 A 9/2010
(Continued)

OTHER PUBLICATIONS

International Search Report and Written Opinion issued for PCT Application No. PCT/US2016/056601, dated Jan. 10, 2017; 14 pages.
(Continued)

*Primary Examiner* — Michael J Dalbo
(74) *Attorney, Agent, or Firm* — Norton Rose Fulbright US LLP

(57) ABSTRACT

The present invention includes an apparatus and method for detecting the location of one or more sources of one or more target molecule, the apparatus comprising: a molecule detector; and a processor connected to the molecule detector and to a global position system, wherein the processor calculates the presence of the one or more target molecules, runs a computer code that determines a dynamic reverse gas stack model for the one or more target molecules, and triangulates the possible position for a source or effluent of the one or more target molecules based on the dynamic reverse gas
(Continued)

stack model. The determined reverse gas stack model may have a Gaussian dispersion over one or more sampled locations.

20 Claims, 39 Drawing Sheets

Related U.S. Application Data

(60) Provisional application No. 62/327,690, filed on Apr. 26, 2016, provisional application No. 62/243,530, filed on Oct. 19, 2015.

(51) Int. Cl.
*G01N 21/65* (2006.01)
*G01N 1/26* (2006.01)
*G01N 1/22* (2006.01)
*G01N 30/72* (2006.01)
*G01N 1/02* (2006.01)

(52) U.S. Cl.
CPC .......... *G01N 21/65* (2013.01); *G01N 30/72* (2013.01); *G01N 33/0057* (2013.01); *G01N 33/0075* (2013.01); *G01N 1/2273* (2013.01); *G01N 30/7206* (2013.01); *G01N 2001/021* (2013.01); *G01N 2201/0221* (2013.01)

(56) References Cited

U.S. PATENT DOCUMENTS

| | | | |
|---|---|---|---|
| 6,577,906 B1* | 6/2003 | Hurtado | G05B 19/41865 700/20 |
| 8,213,007 B2 | 7/2012 | Wang et al. | |
| 9,823,231 B1 | 11/2017 | Steele et al. | |
| 11,287,407 B2* | 3/2022 | Verbeck, IV | G01N 33/0057 |
| 2002/0034757 A1 | 3/2002 | Cubicciotti | |
| 2005/0170523 A1 | 8/2005 | Darrach et al. | |
| 2006/0187017 A1* | 8/2006 | Kulesz | G08B 21/12 340/506 |
| 2007/0029477 A1 | 2/2007 | Miller et al. | |
| 2009/0139299 A1 | 6/2009 | Prince | |
| 2010/0042332 A1 | 2/2010 | Khajehnajafi et al. | |
| 2010/0070197 A1 | 3/2010 | Wang et al. | |
| 2010/0185349 A1 | 7/2010 | Harada et al. | |
| 2010/0185549 A1 | 7/2010 | York et al. | |
| 2011/0063116 A1* | 3/2011 | Lepley | G01N 33/0075 340/605 |
| 2011/0094291 A1 | 4/2011 | Gidon et al. | |
| 2011/0109464 A1 | 5/2011 | Lepley et al. | |
| 2014/0032129 A1* | 1/2014 | Rella | G01N 21/3504 702/23 |
| 2015/0310731 A1* | 10/2015 | Shahraz | G08B 29/18 340/515 |
| 2016/0146696 A1* | 5/2016 | Steele | F17D 5/02 702/51 |
| 2016/0290979 A1* | 10/2016 | Cogill | G01N 33/004 |
| 2017/0022807 A1 | 1/2017 | Dursun et al. | |

FOREIGN PATENT DOCUMENTS

| | | |
|---|---|---|
| CN | 102338764 A | 2/2012 |
| CN | 104280789 A | 1/2015 |
| JP | H09-236561 A | 9/1997 |
| JP | H09-245277 A | 9/1997 |
| JP | 2006511062 A | 3/2006 |
| JP | 2012-132847 A | 7/2012 |
| JP | 2015-121946 A | 7/2015 |
| JP | 2015-176318 A | 10/2015 |

OTHER PUBLICATIONS

Office Action issued for Chinese Patent Application No. 201680071271.3, dated Apr. 16, 2019, with English translation, 12 pages.

Hirst, B. et al. "Locating and Quantifying Gas Emission Sources Using Remotely Obtained Concentration Data" Atmospheric Environment, vol. 74, (2013): pp. 141-158; 18 pages.

Mach, P. M. et al. "Vehicle-Mounted Portable Mass Spectrometry System for the Covert Detection via Spatial Analysis of Clandestine Methamphetamine Laboratories" Analytical Chemistry, vol. 87, (2015): p. 11501-11508, 8 pages.

Communication, extended European search report issued for European Patent Application No. 16858005.8, includes pursuant to Rule 62 EPC, the supplementary European search report and the European search opinion, dated May 28, 2019, 8 pages.

De la Mora, J. F. "The Heavy Molecule—Aerosol Analogy, and the Dispersion of Sound by Gas Mixtures of Disparate Masses," J. Phy. Chem., vol. 88, No. 20, 1984, 4 pages.

Communication pursuant to Article 94(3) EPC issued for European Application No. 16858005.8, dated Jun. 5, 2020, 5 pages.

First Office Action issued for Japanese Patent Application No. 2018-539227, dated Jun. 23, 2020, 9 pages with English translation.

* cited by examiner

DYNAMIC REVERSE GAS STACK MODEL FOR PORTABLE CHEMICAL DETECTION DEVICES TO LOCATE THREAT AND POINT-OF-SOURCE FROM EFFLUENT STREAMS

CROSS-REFERENCE TO RELATED APPLICATIONS

The present application is a continuation of U.S. patent application Ser. No. 15/769,265 filed Apr. 18, 2018 and entitled "DYNAMIC REVERSE GAS STACK MODEL FOR PORTABLE CHEMICAL DETECTION DEVICES TO LOCATE THREAT AND POINT-OF-SOURCE FROM EFFLUENT STREAMS," which claims the benefit of priority from U.S. Provisional Patent Application No. 62/243,530, filed on Oct. 19, 2015, and claims the benefit of priority from U.S. Provisional Patent Application No. 62/327,690, filed on Apr. 26, 2016, the contents of which are incorporated herein by reference in their entirety.

TECHNICAL FIELD OF THE INVENTION

The present invention relates in general to the field of chemical detection, and more particularly, to a dynamic reverse gas stack model for portable chemical detection devices to locate threat and point-of-source from effluent streams.

STATEMENT OF FEDERALLY FUNDED RESEARCH

None.

BACKGROUND OF THE INVENTION

Without limiting the scope of the invention, its background is described in connection with detection of chemical agents.

U.S. Patent Application No. 20090011953, filed by Cooks et al. 2009, discloses methods and apparatuses that use mass spectrometry for preparation of a surface to have catalytic activity through molecular soft-landing of mass selected ions. Mass spectrometry is used to generate combinations of atoms in a particular geometrical arrangement, and ion soft-landing selects this molecular entity or combination of entities and gently deposits the entity or combination intact onto a surface.

U.S. Pat. No. 7,081,617 issued to Mclean et al. 2006, discloses a method and device for the gas-phase separation of ionic biomolecules including peptide, and protein or inorganic cluster ions or nanoparticles by ion mobility and for depositing them intact on a surface in a spatially addressable manner. The surface onto which the proteins are deposited may be modified for the purpose of constructing microarrays of biologically relevant materials or for promoting the growth of highly ordered protein crystals.

U.S. Pat. No. 7,202,472 issued to Schmucker et al., 2007, relates to an improved method for mass spectrometric analysis, in particular for matrix-assisted laser desorption/ionization time-of-flight mass spectrometry (MALDI-TOF MS) using nanoparticles. In the Schmucker patent an analyte is added to a nanoparticle suspension, and the suspension containing the bound analyte is then deposited directly on a MALDI sample carrier and investigated by mass spectrometry, and to a nanoparticle suitable for this method.

SUMMARY OF THE INVENTION

In one embodiment, the present invention includes an apparatus comprising: a portable molecule detector; and a processor connected to the portable molecule detector and to a global positioning system. The processor calculates the presence of one or more target molecules, runs a computer code that determines a dynamic reverse gas stack model for the one or more target molecules to determine a possible position for a source or effluent of the one or more target molecules based on the dynamic reverse gas stack model. In an aspect, the dynamic reverse gas stack model may have a Gaussian dispersion for the one or more target molecules over the one or more sampled locations. In one aspect, the portable molecule detector may be configured to detect chemicals produced by clandestine laboratories, environmental threats, hazardous spills, chemical weapon deployments, or other chemical based threats or hazards. In another aspect, the portable molecule detector may be a portable heavy molecule detector. In another aspect, the portable molecule detector may be selected from at least one of a Raman, infrared (IR), chemical sensor, or mass spectrometer. In another aspect, the processor further obtains environmental data (e.g., wind speed, direction, temp, barometric pressure, other environmental data, or a combination thereof) and determines and/or revises the location of the source based on the environmental data. In another aspect, the portable molecule detector may mounted on, or integrated with a vehicle. In a particular aspect, the vehicle may be a hybrid vehicle or an all-electric vehicle. In another aspect, the processor further obtains infrastructure data that eliminates or enhances an area for a possible location of the source based on a lack of, or presence of, infrastructure including water, electricity, buildings, sewage, wind, or a combination thereof. In another aspect, the volume of sample tested may be increased by the use of a sampling pump that increases gas liquid throughput into the portable molecule detector. In another aspect, the portable molecule detector comprises specific detectors for one or more types of molecules.

In another embodiment, the present invention includes a method of detecting molecules comprising: communicatively coupling a portable molecule detector to a processor and to a global position system, where the processor: receives information indicating the presence of one or more target molecules, runs a computer code that determines a dynamic reverse gas stack model for the one or more target molecules, and triangulates a possible position for a source of the one or more target molecules based on the dynamic reverse gas stack model; and contacting the portable molecule detector with a sample that is suspected of having a molecule to be detected, where the processor determines an approximate location for a source of the molecule based on the level of detection of the molecule and the relative position of the portable molecule detector with relation to global position. In an aspect, the dynamic reverse gas stack model may have a Gaussian dispersion for the one or more target molecules over the one or more sampled locations. In another aspect, the method further comprises the step of selecting the portable molecule detector to detect chemicals produced by clandestine laboratories, environmental threats, hazardous spills, chemical weapon deployments, or other chemical based threats or hazards. In another aspect, the portable molecule detector may be a portable heavy molecule detector. In another aspect, the method further comprises the step of selecting a portable molecule detector from at least one of a Raman, infrared (IR), chemical sensor, or mass spectrometer. In another aspect, the method further comprises the steps of obtaining environmental data (e.g., wind speed, direction, temp, barometric pressure, other environmental data, or a combination thereof) and determining and/or revising the location of the source based on the environmental data. In another aspect, the method further comprises the step of mounting the portable molecule detector in or on a vehicle. In an aspect, the vehicle may be a hybrid vehicle or an all-electric vehicle. In another aspect, the method further comprises the step of obtaining infrastructure data that eliminates or enhances an area for a possible location of the source based on a lack of, or presence of, infrastructure including water, electricity, buildings, sewage, wind, or a combination thereof. In another aspect, the volume of sample tested may be increased by using a sampling pump that increases gas liquid throughput into the portable molecule detector. In another aspect, the method further comprises the step of selecting one or more specific detectors connected to the portable molecule detector, where each of the one or more detectors is selected to detect for one or more types of molecules.

Yet another embodiment of the present invention includes a method of detecting a clandestine laboratory, environmental threats, hazardous spills, chemical weapon deployments, or other chemical based threats or hazards, the method comprising: measuring, at two or more times, samples for one or more detectable agents suspected of being used in the clandestine laboratory, environmental threats, hazardous spills, chemical weapon deployments, or other chemical based threats or hazards with an apparatus, the apparatus comprising: a portable molecule detector; and a processor connected to the portable molecule detector and to a global position system. The processor may be configured to: receive information indicating the presence of one or more target molecules, run a computer code that determines a dynamic reverse gas stack model for the one or more target molecules, and to triangulate a possible position for a source of the one or more target molecules based on the dynamic reverse gas stack model. In an aspect, the dynamic reverse gas stack model may have a Gaussian dispersion for the one or more target molecules over the one or more sampled locations. The processor may further determine the possible location of the clandestine laboratory, environmental threats, hazardous spills, or chemical weapon deployments based on a dynamic reverse gas stack model for the one or more target molecules that is statistically significant as compared other ambient sample, where a statistically significant change in the target molecules indicates the presence and possible location for the clandestine laboratory, environmental threats, hazardous spills, or chemical weapon deployments. In another aspect, the method further comprises the step of selecting a portable molecule detector from at least one of a Raman, infrared (IR), chemical sensor, or mass spectrometer. In another aspect, the method further comprises the step of obtaining environmental data (e.g., wind speed, direction, temp, barometric pressure, other environmental data, or a combination thereof) and determines and/or revises the location of the source based on the environmental data. In another aspect, the method further comprises the step of mounting the portable molecule detector in or on a vehicle, a hybrid vehicle or an all-electric vehicle. In another aspect, the method further comprises the step of obtaining infrastructure data that eliminates or enhances an area for a possible location of the source based on a lack of, or presence of, infrastructure including water, electricity, buildings, sewage, wind, or a combination thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
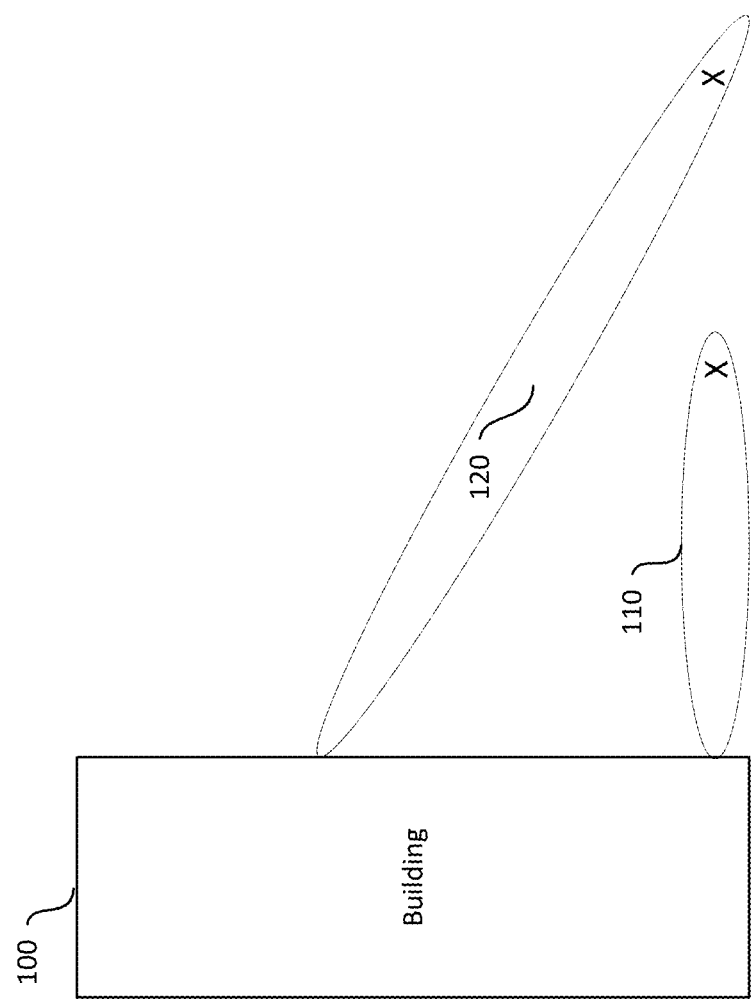
FIG. 1 is a block diagram illustrating differences between embodiments of the present invention and conventional gas stack modelling techniques.

Embodiments of the present disclosure provide for apparatuses, non-transitory computer-readable media, and methods for detecting source locations of one or more target molecules. Gas stack models determined according to embodiments of the present disclosure may be considered reverse gas stack models because, unlike traditional gas stack models that start from a source of one or more molecules and then predict where those one or more molecules will be dispersed into the surrounding environment, gas stack models determined according to embodiments of the present disclosure are derived by detection of the presence of one or more molecules in a sampled environment, and are then used to predict a location of the source of the one or more detected molecules. Thus, gas stack models determined according to embodiments of the present disclosure operates may be considered reverse gas stack models because they are generated from detection of one or more molecules in an environment, and are used to identify a sour for the one or more molecules, rather than being generated based on characteristics of a source and then being used to determine where the molecules will be dispersed into the surrounding environment. Further, reverse gas stack models determined according to embodiments may be dynamic. For example, as sampling of an environment is performed, data points (e.g., molecule concentrations, positioning information, environmental data, infrastructure data, or a combination thereof) may be collected that may be used to predict where the source of the one or more molecules is located. As additional data points are collected/determined, the location of the source may be refined or enhanced to facilitate a more accurate location prediction. The ability to identify the source of the one or more molecules based on collected data points provides dynamic new capabilities in the field of gas stack modeling which are not available using traditional gas stack modeling techniques (e.g., gas stack models constructed based on characteristics of a source). Thus, the reverse gas stack models determined according to embodiments may be considered dynamic reverse gas stack models.

As described in more detail below, chemical detection devices configured according to embodiments are operable to create a dynamic reverse gas stack model that may be utilized to locate threat and point-of-source from effluent streams. Conventional gas stack dispersion modelling technology estimates downwind ambient concentration and dispersion of a stream (e.g., a stream of air pollutants or toxins) based on known source properties, such as the elevation of the source, the rate at which the stream is being released from the source, and the like. While these conventional dispersion models may vary in terms of their implementation, each requires source properties as inputs, such as an emission rate, a source location, a source elevation, and the like. The dynamic reverse gas stack modelling techniques of the embodiments below operates to derive what were once required inputs in conventional gas stack dispersion models using molecule distributions that are dynamically detected in a distributed environment. That is to say, whereas conventional gas stack dispersion modeling technology takes source input data associated with dispersion of a stream into the air and then determines the extent to which the stream will travel, embodiments of the present disclosure utilize new modelling techniques that utilize detection of molecules of interest to predict and/or estimate the location of the source of the molecule of interest. It is noted that the influence of unknown emission source properties prevents source detection using conventional gas stack techniques.

For example, and referring to FIG. 1, a block diagram illustrating differences between embodiments of the present disclosure and conventional gas stack modelling techniques are shown. In FIG. 1, a multistory building 100 is shown. If a tenant of the multistory building 100 was performing clandestine activities, such as making illegal drugs or explosive devices, in the multistory building 100, a stream of molecules may be dispersed into the air which may escape the building, after which the molecules will be dispersed into the surrounding environment. Depending on where the tenant is located the stream of molecules may be dispersed to different distances. For example, if the tenant is located on the first floor of the multistory building 100, a stream of molecules 110 may form and if the tenant is located on the first floor of the multistory building 100, a stream of molecules 120 may form. Because the stream of molecules 120 is released from the multistory building 100 at a higher elevation than the stream of molecules 110, the stream of molecules 120 may be distributed a greater distance into the surrounding environment than the stream of molecules 110. However, both of the streams of molecules 110 and 120 may exhibit similar concentrations at particular points in their relative distributions into the surrounding environment.

For example, at points "X" in each of the streams of molecules 110 and 120 concentrations of a particular molecule may be approximately equal. Using conventional gas stack modeling techniques, models of the streams of molecules 110 and 120 may be determined based on the point of origin for each of the streams of molecules 110 and 120. However, concentrations of a molecule or molecules of interest (e.g., "X" in FIG. 1) may not be used in conventional gas stack modeling techniques to identify the source of the streams of molecules as coming from the first floor of the multistory building 100 (e.g., the molecules of interest correspond to the stream of molecules 110) or a floor higher up in the multistory building 100 (e.g., the molecules of interest correspond to the stream of molecules 120). In contrast, embodiments of the present disclosure utilize new gas stack modeling techniques to sample concentrations of molecules in an environment and determine a potential point of origin or source for the molecules (e.g., based on a concentrations of molecules of interest detected in an environment, such as concentrations of molecule(s) "X" in FIG. 1, embodiments of the present disclosure are capable of determining whether the molecules of interest correspond to the stream of molecules 110 coming from the first story of the multistory building 100 or the stream of molecules 120 coming from the a floor higher up in the multistory building 100), as described in more detail below. In other words, embodiments of the present invention provide new and robust gas stack modeling techniques that allow identification of a point of origin from information about a stream of molecules distributed in an environment, a capability that currently available gas stack modeling techniques are not capable of performing. Additional aspects of embodiments of the present disclosure are described in more detail below, with reference to FIGS. 2-34.

While aspects related to the making and usage of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In the field, chemical effluent streams are formed under a myriad of examples. Some of these are clandestine labs, environmental threats, hazardous spills, and chemical weapon deployments. These are specific examples of effluent streams that have an unknown source at time of detection. These types of activities would go undetected, or at best, be detected by a report of smells or chemical activity. However, portable mass spectrometers are now capable of detecting many of the chemical streams produced during activities identified in the above list, and can be trained to look for types of chemical effluent streams. This combined with the current global positioning system (GPS) capabilities, and system advisor model (SAM) Weather data that can be accessed in real time, may allow a chemical detector (here a mass spectrometer) configured according to embodiments of the present disclosure to pinpoint and map effluent, thereby enabling a source of the effluent to be identified.

Chemical detectors according to embodiments of the present disclosure may be embodied in aerial, ground, water, even outer worldly applications, and may enable detection of clandestine labs (e.g., drugs, weapons, counterfeit, explosives, etc.), hazardous effluent (e.g., oil and gas, chemical spills, industrial fires, etc.), poisonous streams (e.g., chemical weapons, high level toxicity), and natural chemical streams (e.g., volcano, seepage, etc.).

Chemical detectors according to embodiments of the present disclosure may determine chemistry while on the move. Once a chemical is detected, a dynamic reserve gas stack model may be used to determine a dispersion model that may be utilized to locate a potential point of source for an effluent stream. In an embodiment, this model may be revised by integrating environmental data (e.g., wind speed, direction, temp, barometric pressure, etc.), or infrastructure data (e.g., water, electrical, sewage, gas, buildings, etc.), or both to narrow or refine a potential point of source for the effluent stream. In an additional or alternative embodiment, integrating environmental data (e.g., wind speed, direction, temp, barometric pressure, etc.), or infrastructure data (e.g., water, electrical, sewage, gas, buildings, etc.), or both to narrow or refine a potential point of source for the effluent stream may be performed during the initial determination of the dynamic reverse gas stack model. As the chemical detector senses the chemistry, software executing at the chemical detector may instruct the operator as to the direction of source. New chemistry can then be detected (heavier constituents or higher concentrations of the molecule(s)), and this may be used to further narrow the point of source, and identify the potential threat to the community, local environment, or identify illegal chemical activity.

Chemical detectors configured according to embodiments may utilize a variety of chemical sensors, such as Raman spectrometer, infrared (IR) spectrometer, chemical sensors, mass spectrometers, another type of sensor operable to detect molecules of interest, or a combination thereof. Chemical detectors configured according to embodiments may also cover a broad spectrum of chemical information and threat assessment, and may be utilized in conjunction with aerial, ground, water, and submersible devices to perform the operations described herein for locating a point of source of an effluent stream.

The uses of chemical detectors configured according to embodiments of the present disclosure may be applied to portable chemical detector operators, automation (e.g., the software may be configured to drive a vehicle), and remote uses. This may be employed in aerial, ground, water, even outer-worldly deployments. The chemical detectors according to embodiments may detect a very large dynamic range of concentrations, such as percent or part-per-trillion concentrations.

Figure 2:
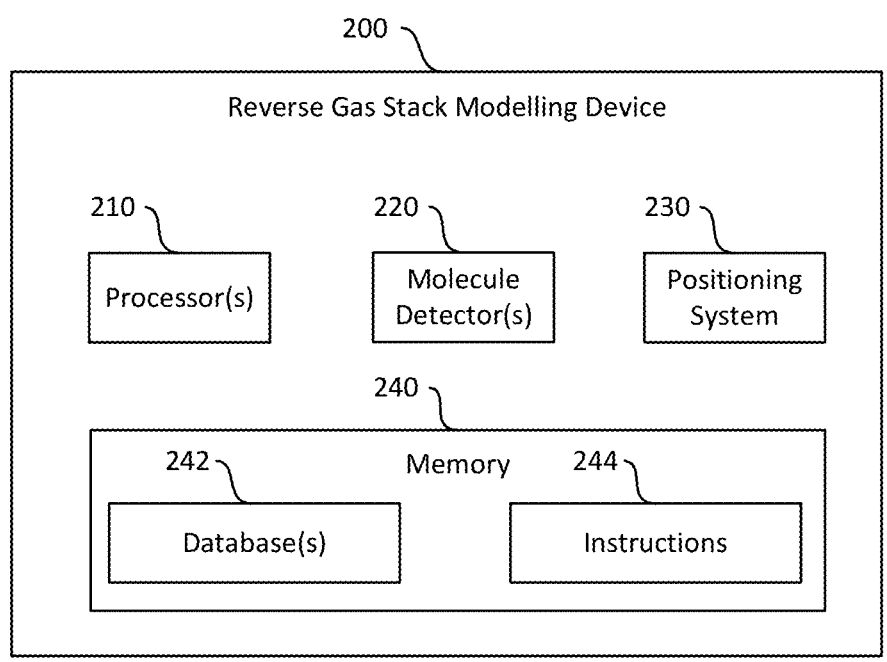
FIG. 2 is a block diagram illustrating an embodiment of an apparatus for locating a source of one or more target molecules in accordance with embodiments of the present disclosure.

Referring to FIG. 2, a block diagram of an exemplary apparatus for locating a source of one or more target molecules in accordance with embodiments of the present disclosure is shown as a dynamic reverse gas stack modeling device 200. As shown in FIG. 2, reverse gas stack modeling device 200 may include one or more processors 210, one or more sensors 220, a positioning system 230, and a memory 240. The memory 240 may include one or more databases 242. Additionally, the memory 240 may store instructions 244 that, when executed by the one or more processors 210, cause the one or more processors 210 to perform operations for locating a source of one or more target molecules in accordance with embodiments of the present disclosure, as described in detail below. In an embodiment, the reverse gas stack modeling device 200 may be a portable device. For example, the reverse gas stack modeling device 200 may be integrated within, installed on, or otherwise utilized as part of a mobile molecule detection platform. In an embodiment, the mobile molecule detection platform may comprise a vehicle, such as a hybrid vehicle, a hydrogen vehicle, or an all-electric vehicle. In an additional or alternative embodiment, the mobile molecule detection platform may comprise a plane, a drone, an unmanned aerial vehicle, a helicopter, or another form of aircraft. In yet another additional or alternative embodiment, the mobile molecule detection platform may comprise a boat, a submarine, a hovercraft, or another form of watercraft. In still another additional or alternative embodiment, the mobile molecule detection platform may deployed in other configurations, such as a backpack-sized system, a robot, and the like. It is noted that the particular components of the reverse gas stack modeling device 200 illustrated in FIG. 2 are provided for purposes of illustration, rather than by way of limitation, and the reverse gas stack modeling device 200 may include other components, not shown in FIG. 2. For example, the reverse gas stack modeling device 200 may include a power supply, a display device, one or more input/output (I/O) devices and/or interfaces (e.g., a keyboard, a mouse or other pointing device, and the like), one or more communication interfaces (e.g., a wireless communication interface, a wired communication interface, and the like), or other components.

The one or more molecule detectors 220 may be adapted to generate information representative of the presence of one or more target molecules based on one or more samples of an environment. For example, the reverse gas stack modeling device 200 may be traversed across an environment (e.g., a geographic area, such as an area surrounding a building, a neighborhood, a road, a city, and the like) and, as the reverse gas stack modeling device 200 traverses the area, the one or more molecule detectors 220 may periodically or continuously sample aspects of the environment (e.g., surfaces within the environment, air within the environment, water within the environment, and the like). In an embodiment, as the one or more molecule detectors 220 sample the environment, the information representative of the presence of one or more target molecules based on one or more samples of an environment may be generated and stored in the database(s) 242. In an additional or alternative embodiment, the information representative of the presence of one or more target molecules based on one or more samples of an environment may be generated by the one or more molecule detectors 220 and provided to the one or more processors 210 as a stream of data. In still another additional or alternative embodiment, the information representative of the presence of one or more target molecules based on one or more samples of an environment may be generated by the one or more molecule detectors 220 and provided to the one or more processors 210 as a stream of data simultaneously with storing the information in the database(s) 242. In an embodiment, the one or more target molecules may be associated with one or more chemicals produced by, or as a byproduct of production processes performed at, clandestine laboratories, environmental threats, hazardous spills, environmental pollutants, effluent chemicals, chemical weapon deployments, or a combination thereof. In an embodiment, the one or more molecule detectors 220 may comprise at least one heavy molecule detector. In an additional or alternative embodiment, the one or more molecule detectors 220 may comprise one or more Raman spectrometers, infrared (IR) spectrometers, chemical sensors, mass spectrometers, or a combination thereof. In an embodiment, the one or more molecule detectors 220 may comprise specific detectors for one or more types of molecules associated compounds comprising polycyclic aromatic hydrocarbon emissions (PAHs), benzene, alkyl benzene, chlorobenzene, or trichlorobenzene, isopropylbenzene, ethylbenzene, cyclohexanone, xylene, p-cymene, hydrocarbons produced by oil and gas exploration or extraction, methane, ethane, propane, butane, pentane, hexane, toluene, trichloroethene, chloroform, tetrachloroethane, 1,1,1-trichloroethane, 1,1,2,2-tetrachloroethane, xylene, carbon tetrachloride, 1,1-dichloroethane, or 1,2-dichloroethane. It is noted that, in some embodiments, detectors for one or more other types of molecules may also be provided depending on the particular molecules for which the reverse gas stack modelling device 200 is configured to detect, and that the molecules listed above are provided for purposes of illustration, rather than by way of limitation. For example, the reverse gas stack modelling device 200 may be configured detect to both aromatic and non-aromatic molecules, hydrocarbons, and the like. In an embodiment, the reverse gas stack modeling device 200 may comprise one or more pumps (not shown in FIG. 2) configured to increase a volume of sample tested by the one or more molecule detectors 220.

As the environment is sampled, the positioning system 230 may periodically generate location information representative of one or more locations, where each of the one or more locations corresponds to a location where a sample of the one or more samples of the environment was obtained. In an embodiment, as the positioning system 230 generates the location information, the location information may be stored in the database(s) 242. In an additional or alternative embodiment, the location information may be generated by the positioning system 230 and provided to the one or more processors 210 as a stream of location data. In still another additional or alternative embodiment, the location information may be generated by the positioning system 230 and provided to the one or more processors 210 as a stream of location data simultaneously with storing the information in the database(s) 242. In an embodiment, the positioning system 230 may comprise a global positioning system (GPS). In an additional or alternative embodiment, the positioning system 230 may comprise a telecommunications-based positioning system, such as a positioning system that uses cellular communication system (e.g., cellular base stations, access points or other wireless communication technologies) to determine a position for a respective sample. In still another additional or alternative embodiment, the positioning system 230 may comprise a local positioning system. For example, when the scanning or sampling of an environment is not capable of utilizing GPS or telecommunications-based positioning technologies (e.g., because the sampling is performed inside a building or underground where signals necessary for obtaining positioning information using GPS and telecommunications-based technologies cannot be reliably obtained), a local coordinate system may be used, and the local coordinate system may be subsequently mapped to "real-world" coordinates. This may be done by configuring the local coordinate system such that at least one point in the local coordinate system corresponds to a location known in "real-world" coordinates, and the mapping the coordinates obtained in the local coordinate system to "real-world" coordinates based on the at least one point having a location known in both the local coordinate system and "real-world" coordinates. When a local coordinate system is used, the reverse gas stack modeling device may comprise one or more accelerometers and/or gyroscopes which may be utilized by the reverse gas stack modeling device 200 to measure linear and rotational acceleration and/or velocity of the reverse gas stack modeling device 200 during the sampling. In an embodiment, the positioning system 230 may comprise a combination of these different systems and/or other positioning systems not described herein for simplicity of the disclosure.

In an embodiment, the location information and the information representative of the presence of one or more target molecules based on one or more samples of an environment may be timestamped. For example, when a sample of the environment is obtained and information representative of the presence of one or more target molecules based on the sample of the environment is generated, the presence information may be timestamped and location information corresponding to the location where the sample of the environment occurred may also be generated and timestamped. In such an embodiment, the processing of the samples to identify the source of the one or more target molecules may be performed at a later time (e.g., using the information stored in the database). This may enable the reverse gas stack modelling device 200 to be constructed at a reduced cost (e.g., because the device would require less power and computational resources during operation).

In an embodiment, the one or more processors 210 may initiate and control the sampling. For example, the instructions 244 may provide an application that may be executed by the one or more processors 210 to control the operations of the reverse gas stack modeling device 210, such as to initiate the sampling by the one or more molecule detectors 220 and to obtain the location information from the positioning system 230. The one or more processors 210 may be configured to receive the information representative of the presence of one or more target molecules based on one or more samples of an environment and the location information, and to determine, based on the information representative of the presence of one or more molecules and the location information, a dynamic reverse gas stack model for the one or more target molecules over the one or more sampled locations. In an embodiment, the dynamic reverse gas stack model may have a Gaussian dispersion for the one or more target molecules over the one or more sampled locations. In an embodiment, this information may be received directly from the one or more molecule detectors 220 and the positioning system 230. In an additional or alternative embodiment, this information may be received by retrieving the information from the database(s) 242. After determining the dynamic reverse gas stack model with the Gaussian dispersion for the one or more target molecules over the one or more sampled locations with respect to Equations 1-17, detailed below, the one or more processors 210 of FIG. 2 may predict a location for a source of the one or more target molecules based on the dynamic reverse gas stack model.

In an embodiment, the dynamic reverse gas stack model with a Gaussian dispersion for the one or more target molecules over the one or more sampled locations may be generated by solving a Gaussian dispersion equation based on the presence and/or concentration of sensed chemicals. In an embodiment, the Gaussian dispersion equation may be a Generalized Gaussian Dispersion Equation for a Continuous Point-Source Plume, and may be given by:

$$C_{(x,y,z_r)} = \frac{Q}{u\sigma_z\sigma_y 2\pi}e^{\frac{-y^2}{2\sigma_y^2}}\left[e^{\frac{-(z_r-H_e)^2}{2\sigma_z^2}}+e^{\frac{-(z_r+H_e)^2}{2\sigma_z^2}}\right] \qquad \text{Eq. 1}$$

Where: C=concentration of emissions, $g/m^3$, at any location located at:
x meters downwind
y meters from centerline
$z_r$ meters above ground
Q=source emission rate, g/sec
u=horizontal wind velocity, m/sec
$H_e$=plume centerline height above ground, m
$\sigma_z$=vertical standard deviation of the emission distribution, m
$\sigma_y$=horizontal standard deviation of the emission, m In embodiments where ground-based chemical detection systems are deployed, analysis may concentrate on downwind ground level detection of concentrations, $z_r$=0, and the Ground-Level Centerline and Crosswind Concentrations may be reduced from Eq. 1 to:

$$C_{(x,y,0)} = \frac{Q}{u\sigma_z\sigma_y\pi}e^{\frac{-y^2}{2\sigma_y^2}}e^{\frac{-H_e^2}{2\sigma_z^2}} \qquad \text{Eq. 2}$$

Primary analysis may begin at the highest concentration and deviation from that detected point will surmise the Gaussian shape. Thus, a maximum ground level concentrations may be detected at $z_r$=0 and y=0. Thus, Eq. 1 can be reduced to the Ground-Level Centerline Concentration:

$$C_{(x,0,0)} = \frac{Q}{u\sigma_z\sigma_y\pi}e^{\frac{-H_e^2}{2\sigma_z^2}} \qquad \text{Eq. 3}$$

Additionally, since embodiments may primarily target ground level or near ground level emissions, $z_r$=0, y=0, and He=0, the Ground-Level Centerline Concentrations from Ground-Level Plumes may be:

$$C_{(x,0,0)} = \frac{Q}{u\sigma_z\sigma_y\pi} \qquad \text{Eq. 4}$$

Equations 1 and conditional reduced forms may be used to back calculate a given location from a detected plume. While a certain degree of uncertainty may be expected, refinement of the application of these deduced equations can serve to limit a region for point source determination to within a threshold distance of the point source.

The Gaussian function may be presented as:

$$y = Ae^{\frac{-(x-\mu)^2}{2\sigma^2}} \qquad \text{Eq. 5}$$

Whereby the curve is centered at x=μ, with A being the height of the peak and σ the standard deviation width on both sides of the peak curve. Taking the natural logarithm of the Gaussian function in Eq. 5 yields:

$$\ln y = \ln A + \frac{-(x-\mu)^2}{2\sigma^2} \qquad \text{Eq. 6}$$

Equation 6 expanded:

$$\ln y = \ln A - \frac{\mu^2}{2\sigma^2} + \frac{2\mu x}{2\sigma^2} - \frac{x^2}{2\sigma^2} \qquad \text{Eq. 7}$$

Equation 7 takes the Quadratic form shown in Equation 8:

$$\ln y = a + bx + cx^2 \qquad \text{Eq. 8}$$

When: $a = \ln A - \frac{\mu^2}{2\sigma^2}$ $b = \frac{\mu}{\sigma^2}$ $c = \frac{-1}{2\sigma^2}$ The Gaussian parameters A, µ, and σ may be calculated from a, b, c. Curve fitting of a parabola like data set from the mobile mass spectrometer may be accomplished in the least squares sense. Solving for the series of quadratic coefficients, a Gauss error function from Eq. 8 may be given by:

$$\delta = \ln y - (a + bx + cx^2) \qquad \text{Eq. 9}$$

A linear system of equations results when differentiating the sum of $\delta^2$ with respect to a,b, and c while setting the linear system of equations to zero yields:

$$\begin{bmatrix} N & \Sigma x & \Sigma x^2 \\ \Sigma x & \Sigma x^2 & \Sigma x^3 \\ \Sigma x^2 & \Sigma x^3 & \Sigma x^4 \end{bmatrix} \begin{bmatrix} a \\ b \\ c \end{bmatrix} = \begin{bmatrix} \Sigma \ln y \\ \Sigma x \ln y \\ \Sigma x^2 \ln y \end{bmatrix} \qquad \text{Eq. 10}$$

Where N is the number of collected data points (e.g., the number of sampled locations) and $\Sigma$ denotes $\Sigma_{n-1}^{N} x$. Solving this linear system of equations will yield a, b, and c, which can then be used to deduce the Gaussian parameters A, µ, and σ, via:

$$\mu = \frac{-b}{2c} \qquad \text{Eq. 11}$$

$$\sigma = \sqrt{\frac{\pm 1}{2c}} \qquad \text{Eq. 12}$$

$$A = e^{\frac{a-b^2}{4c}} \qquad \text{Eq. 13}$$

Unification of Equation 4 may be accomplished by relating the height of a given Gaussian peak, A, to as obtained from a dataset from Equation 13 to the concentration C, of Equation 14. The obtained path of sampling provides a Gaussian shape, whereby point µ is a point where a line normal to the sampling path provides the linear path of air dispersion between the point source and detection. Final application to either Equation 3 or 4, the σ value is used to calculate final distance normal to a Gaussian fit. Equation 14, $$\sigma = e^{I + J(\ln x) + K(\ln x)^2} \qquad \text{Eq. 14}$$

solves for the upwind distance using a standard deviation of the concentration in the horizontal or vertical, in the case of solving the He value in Equation 3, in meters, the natural log of the downwind distance, hereby the target value for solving Equation 14, in kilometers, and I, J, and K are empirical constants for a given atmospheric stability. Finally the degree of deviation, σ, is relatable to the distance of the point source and its location. Solving Equation 14 for x, the distance upwind for the source location yield:

$$x = e^{\pm \frac{\sqrt{4\sigma K - 4IK + J^2} - J}{2K}} \qquad \text{Eq. 15}$$

Whereby, I, J, and K are obtained from atmospheric conditions, and $\sigma_y$ is solved via the approximation in Eq. 12.

A continuous point source emission depends on a variety of assumptions and requires an ideal setting for effective approximation. Such constraints include: (1) emission being continuous, (2) no chemical reactions or absorption of emissions, (3) wind direction and speed are constant, and/or (4) dispersion is Gaussian in nature. These constraints are frequently observed atmospherically and application of the model can be accomplished routinely. For ground level detection and emission, the distance upwind, x, to such emissions from detection can be approximated via unification of the elucidated formulas, such that Eq. 4 and 15 are united in:

$$x = \frac{Q}{Cu\sigma_z \left| e^{\pm \frac{\sqrt{4\sigma K - 4IK + J^2} - J}{2K}} \right| \pi} \qquad \text{Eq. 16}$$

Equation 15 may also be applied to Eqs. 2 and 3 so terms that further approximate atmospheric chemical release, including increased release height and crosswind variability. Equation 16 solves the Gaussian dispersion of atmospheric dispersion in reverse such that known concentrations or intensities obtained from portable instrumentation may be used to approximate upwind distance. Such solutions exhibit an ability to approximate upwind distance from a Gaussian dispersion of chemical detection.

The approximate determination of location for emission release may be applied to many different situations. Tracking anomalous plumes and determining location may be useful for environmental regulatory agencies. Law enforcement applications include tracking emissions of active clandestine manufacture of illegal substances. Disaster response would be able to directly measure effected regions and confirm location of toxic spills or releases of dangerous chemicals, and offer further dispersal predictions. A mobile mass spectrometer configured according to embodiments may serve as a complete sensing unit with multiple usages that could be rapidly deployed from routine mapping and air quality measurements to emergency response. FIG. 2, described above, and FIGS. 9-11, described in more detail below, provide various different configurations for embodiments of a mobile mass spectrometer according to the present disclosure, and include a standalone unit (e.g., FIG. 2), a modular system (e.g., FIG. 9), and a cloud-based system (e.g., FIG. 10). Additionally, embodiments may further comprise fixed systems configured to detect point sources of effluent streams, as described in more detail below with reference to FIG. 11.

Figure 3:
FIG. 3 shows a Gaussian dispersion model of benzene, xylenes, and p-cymene.

Examining the effect of traversing winds, molecular mass, and boiling points of chemical interests provides an indication of how the model operates in real world situations. For example, FIG. 3 shows a conventional gas stack model of a hypothetical release of benzene, xylenes, and p-cymene modeled in the Areal Locations of Hazardous Atmospheres (ALOHA) software, starting from a known emission source. ALOHA utilizes atmospheric distribution equations to model how hazardous gases travel downwind. FIG. 3 shows an example of point source modeling that shows the dispersion of chemical interests of increasing mass of benzene and alkyl benzene class of chemicals, ignoring overtly large buildings and anomalous landscapes. Conditions modeled are at 70° F., with north winds at 5 mph, 50% humidity, with stable atmospheric conditions. Each region plotted is modeled to be a 100 ppb concentration from an emission source at a known point of origin at a rate of 1 g/min. Dispersal of these chemicals has discernable regional downwind dispersion that is due to inherent chemical properties.

Figure 4:
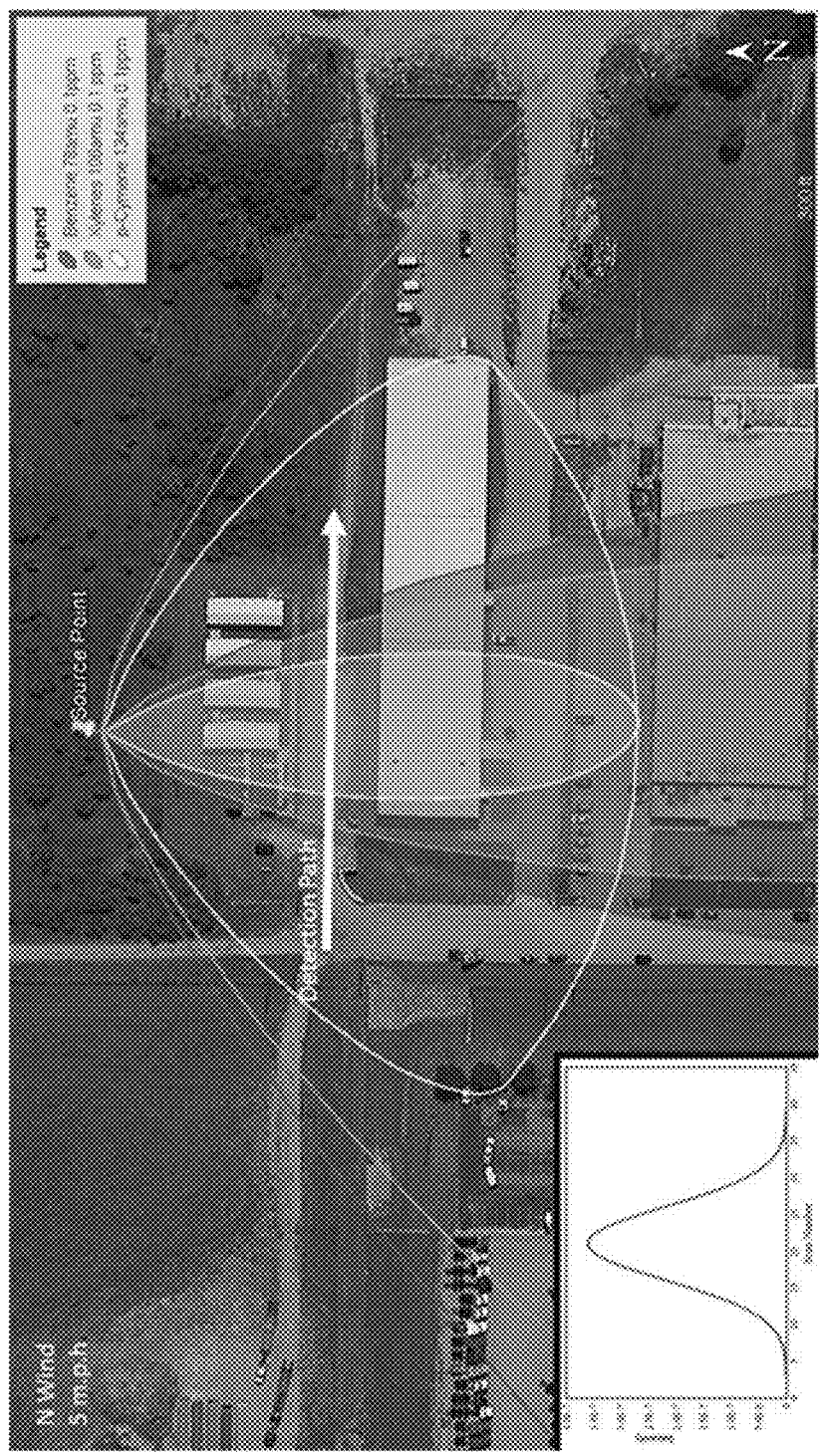
FIG. 4 shows a detection path through the Gaussian dispersion model of benzene, xylenes, and p-cymene illustrated in FIG. 3.

Using a portable chemical detector of the present invention, such as a mass spectrometer configured according to embodiments of the present disclosure, to validate the emission source of the ALOHA model illustrated in FIG. 3, a path may be traversed, as indicated in FIG. 4, to detect the presence of molecules of interest. It can be noted that obtained data will have a normal distribution. In FIG. 4, the rise and fall of the concentration of the chemical interest in the atmosphere is shown. The peak of the curve would be the point where a line normal to the traversed detection path upwind where the chemical of interest would be located. Higher standard deviation may be indicative of more highly distributed chemical compounds. Multiple such normal distributions would exist for mixed chemical interests. Each scan may be tagged with location data (e.g., GPS data or another form of location data) so that relevant spatial information is obtained, stored and/or correlated to the location of the detected chemicals.

Figure 5:
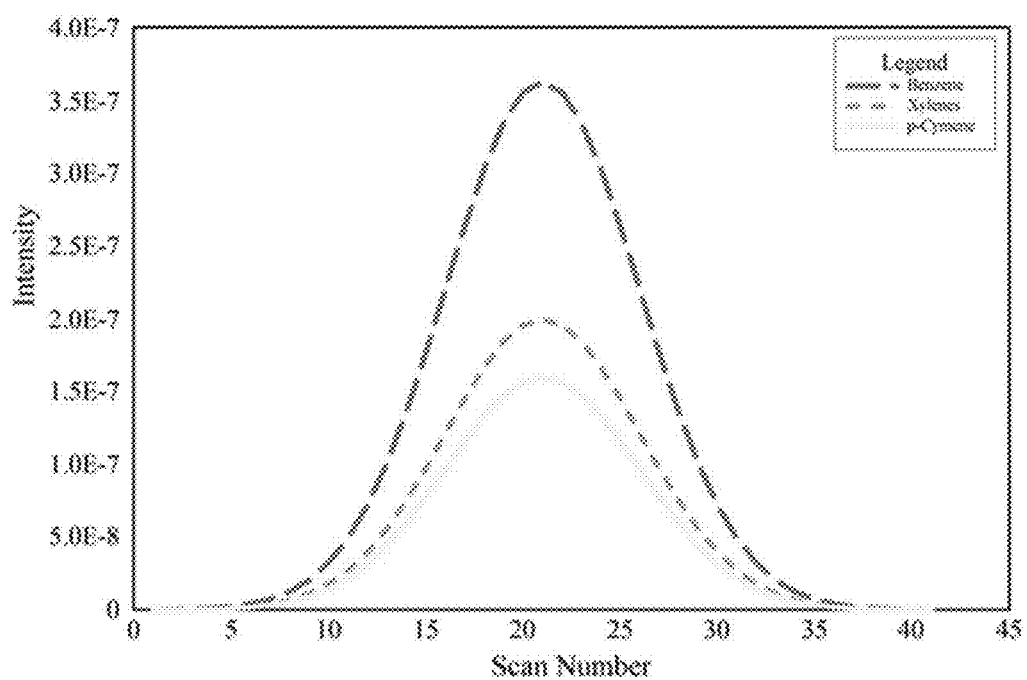
FIG. 5 is a graph that shows multiple detections of normal distributions from the simulated dataset illustrated in FIG. 3.

Since most data sets will contain multiple chemical compounds, the distributions of detected chemical compounds may contain differing characteristics, including different peak heights and standard deviations. FIG. 5 illustrates the plotting of multiple chemicals and their detection in an idealized setting. As the mobile system traverses a given region, detection may begin with the most distributed chemical compound and subsequent detections may be less dispersed compounds. Multiple alignments of the peak, based upon scan number (e.g., the number of locations where samples are obtained) and positioning information (e.g., GPS information and the like), may provide further indication of upwind release.

In consideration of mobile mass spectrometric systems, inherent fragmentation due to ionization produces similar results. As a chemical with a given precursor mass is introduced, product fragments produced via ionization align with the product ion mass, albeit with differing intensity corresponding to the degree of fragmentation of the precursor ion. Precursor ions and their associated product ions serve as a method of identification in mass spectrometers. While fragmentation operations may not be carried out in a given scan, normal distributions that have aligning peak heights and standard deviations have an association to each other, with the highest mass being the precursor ion. This may be useful as many fragments and precursor ions are detected, spectra are deconvoluted and separated by association in similar normal distributions.

As an operator cannot always traverse normal to the line of downwind release, the direction of travel and direction from which the wind is traveling become highly important in localizing sources. Such data sets may be normal in distribution, but skewed as the standard deviations, +σ and −σ, either side of the peak may not be equal. Regardless, a directional line towards the source can be determined by observing the peak of a normal distribution and tracing a route upwind towards the cardinal direction the wind is originating from.

Increases in molecular mass and additional functional groups effect boiling point, among other factors, and allow for a noticeable difference in dispersion and release of chemicals. For example, with hydrocarbon chains, increases in mass correspond to increases in boiling point. Considerations may be made to account for the correlation between detections of compounds and those detected chemical's properties. While volatilized chemicals may be carried via wind and affected by atmospheric conditions, rates may differ due to the chemical nature of those compounds. Early detected compounds may have chemical properties that include lower boiling point and higher vapor pressure.

When membrane inlet mass spectrometry (MIMS) is used during mobile detection according to embodiments, the system may take into account the rate of permeability of different compounds. Rates of permeability may be determined for known compounds for a given system, but for unknowns and detection in the field, chemical properties may be assumed to narrow down possible chemical constituents. Types of membrane that are installed may be selective for certain chemistries, thus limiting the structural properties of a chemical that is detected. Timing of detection relating to mass can be accomplished by assuming that lower mass compounds volatilize first and are more widely dispersed, as in FIG. 3. Furthermore, efforts have quantified polydimethylsiloxane (PDMS) MIMS response times for a variety of chemical interests. Membrane response time may be determined by membrane thickness and diffusion coefficient. Thin membranes may offer time-scale rates of detection in seconds for VOCS. Table 1 shows one example of relevant membrane response times for a 25 μm thick PDMS, and correlates to mass and boiling point.

TABLE 1

| Compund | Response Time (s ± 1 s) * | Molar Mass (g/mol) | Boiling Point (° C.) |
|---|---|---|---|
| Toluene | 1.3 | 92.14 | 110.60 † |
| Trichloroethene | 1 | 131.38 | 87.20 † |
| Benzene | 1.1 | 78.11 | 80.08 † |
| Chloroform | 1.2 | 119.38 | 61.17 † |
| Tetrachloroethene | 1.4 | 165.833 | 121.3 † |
| 1,1,1-Trichloroethane | 1.7 | 133.404 | 74.00 † |
| 1,1,2,2-Tetrachloroethane | 2.5 | 167.849 | 146.15 † |
| o-Xylene | 1.7 | 106.165 | 144.50 † |
| p-Xylene |  |  | 138.23 † |
| m-Xylene |  |  | 139.07 † |
| Carbon tetrachloride | 1.1 | 153.823 | 76.65 ‡ |
| 1,1-Dichloroethane | 1 | 98.959 | 57.35 ‡ |
| (Z)-1,2-Dichloroethene | 1.1 | 96.943 | 60.20 † |
| (E)-1,2-Dichloroethene |  |  | 48.50 † |
| Chlorobenzene | 1.9 | 112.557 | 131.75 ‡ |
| 1,3-Dichlorobenzene | 2.2 | 147.002 | 173.05 ‡ |
| 1,2,4-Trichlorobenzene | 3 | 181.447 | 213.55 ‡ |

‡ Linstrom, Peter J., and W. G. Mallard. "NIST Chemistry webbook; NIST standard reference database No. 69." (2001). Boiling Point Data" by R. L. Brown and S. E. Stein.
† National Center for Biotechnology Information. PubChem Compound Database; CID = 5934766, http://pubchem.ncbi.nlm.nih.gov/summary/summary.cgi?cid=5934766
* R. Ketola, M. Ojala, H. Sorsa, T. Kotiaho, R. Kostiainen, Development of a membrane inlet mass spectrometric method for analysis of air samples, Analytica chimica acta, 349 (1997) 359-365

Figure 6:
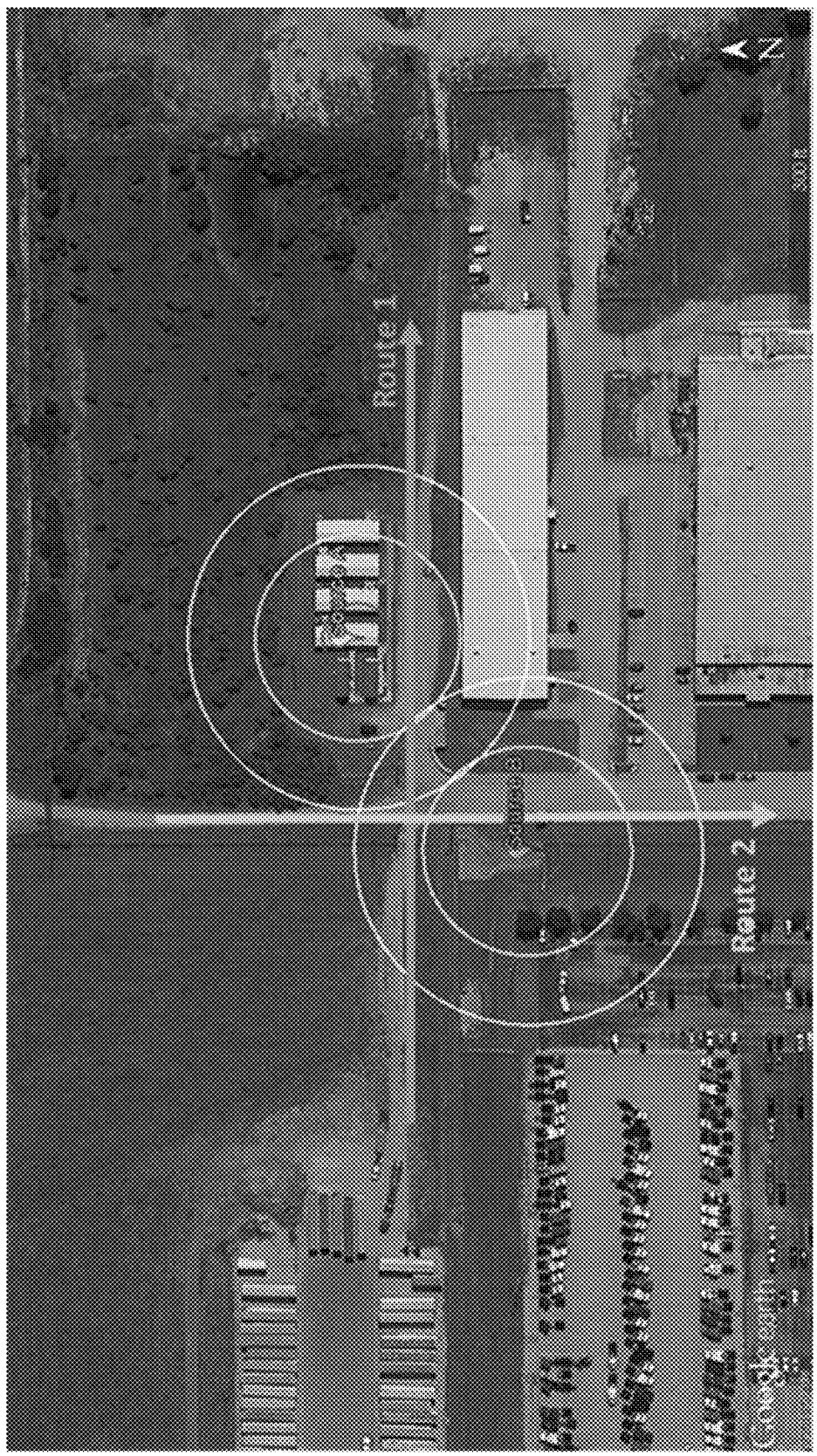
FIG. 6 shows the detection of multiple compounds from two sources via two differing routes to determine of the location of each source according to embodiments.

One of the analytical problems of such analysis is sampling an environment that has multiple sources emitting. FIG. 6 illustrates two possible routes for traversing a region with two continuous point sources. The two illustrated routes, Route 1 and Route 2, traverse through two plumes each. Concentric rings represent differing compounds being emitted, and all are targets for detection. Route 1, traveling from west to east, detect the most disperse compound from Source B first. Upon reaching the dispersed chemical interests from Source A, initial detection is the most dispersed, outer circle, and followed by the second most dispersed, middle circle. Detecting multiple compounds successively as an operator nears a source confirms an approach that provides two Gaussian curves for reverse modeling. Route 2 depicts a similar scenario, traversing from north to south. It detects the most disperse chemical from Source A first, then it dissipates. Source B's emitting chemicals are subsequently detected, with the most dispersed detected first and then the least dispersed (e.g., the center interior circle surrounding source B). Route 1 detects three chemicals of interest, proving three Gaussian curves for determinations.

Figure 7:
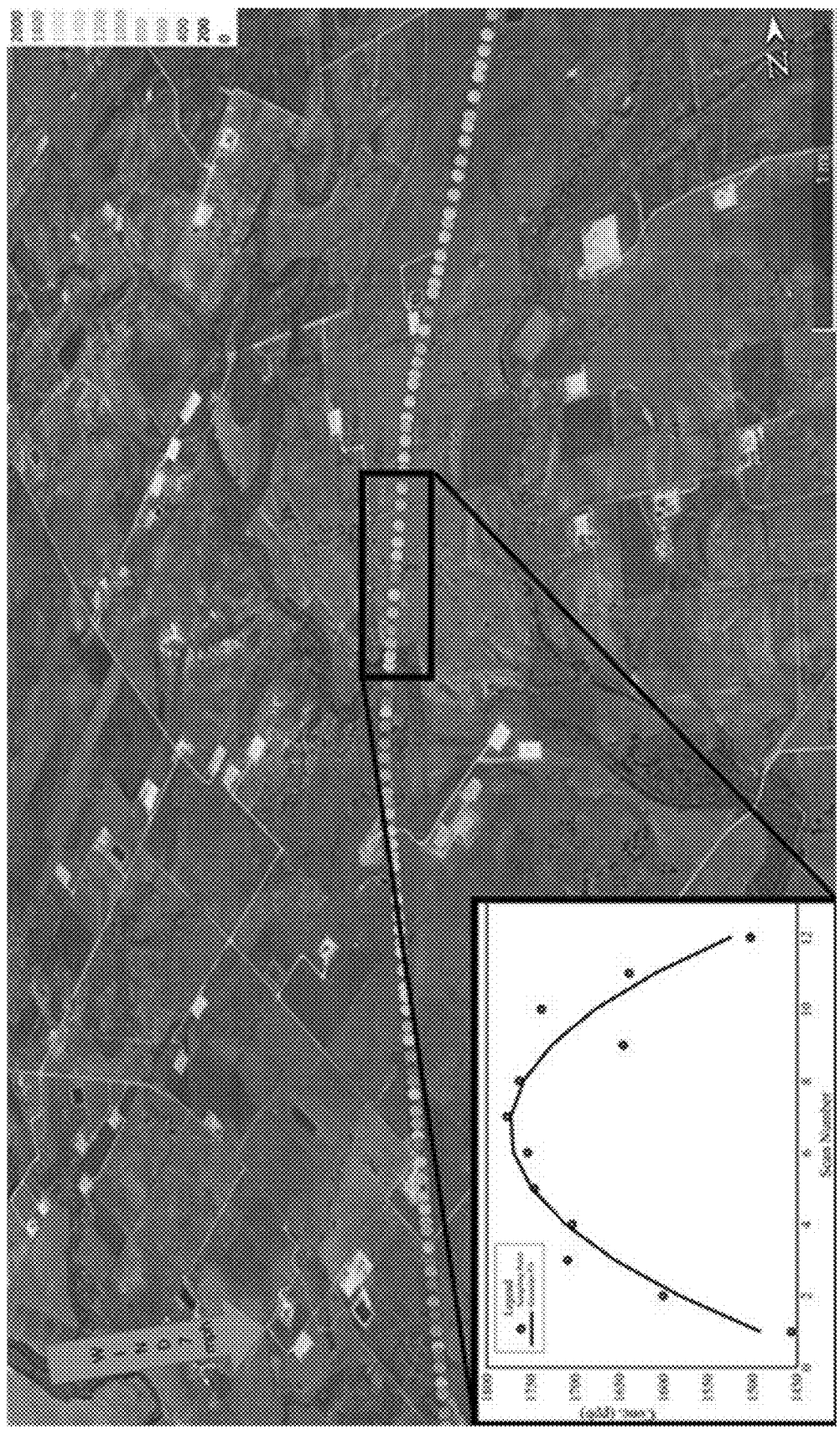
FIG. 7 shows a detection data set obtained from the Eagle Ford Shale region according to embodiments.

In another test scenario, a mobile mass spectrometer system according to embodiments was deployed to the Eagle Ford Shale in central Texas. Over 1,000 miles of roadway was mapped. FIG. 7 shows data points obtained over a county road. Each circle plotted represents a detected concentration of toluene (91 m/z), and this highlighted area covers approximately three-quarters of a mile. A plot of the obtained concentration for successive scans has been fit to a quadratic function, Eq 17.

$$y=-8.7684x^2+116.94x+1384.4 \qquad \text{Eq. 17}$$

The Gaussian parameters were solved for using Eq. 11-13, such that $\mu=-0.042235$, $\sigma=0.019$, and $A=1.32553$. The day of sampling falls into Stability Class D, according to Beychok and Turner. The approximate source distance may be calculated from Eq. 16. In FIG. 7, the star 700 marks the calculated point source approximately 4,224.016 feet west of the detection on the roadway. Downwind detection of Gaussian peak distribution remains the most important part of atmospheric dispersion detections. Portable and mobile units, such as the reverse gas stack modelling device 200 of FIG. 2, concentrating on Gaussian dispersion identification and calculating the peak of those obtained curves may provide insight into upwind location.

Figure 8:
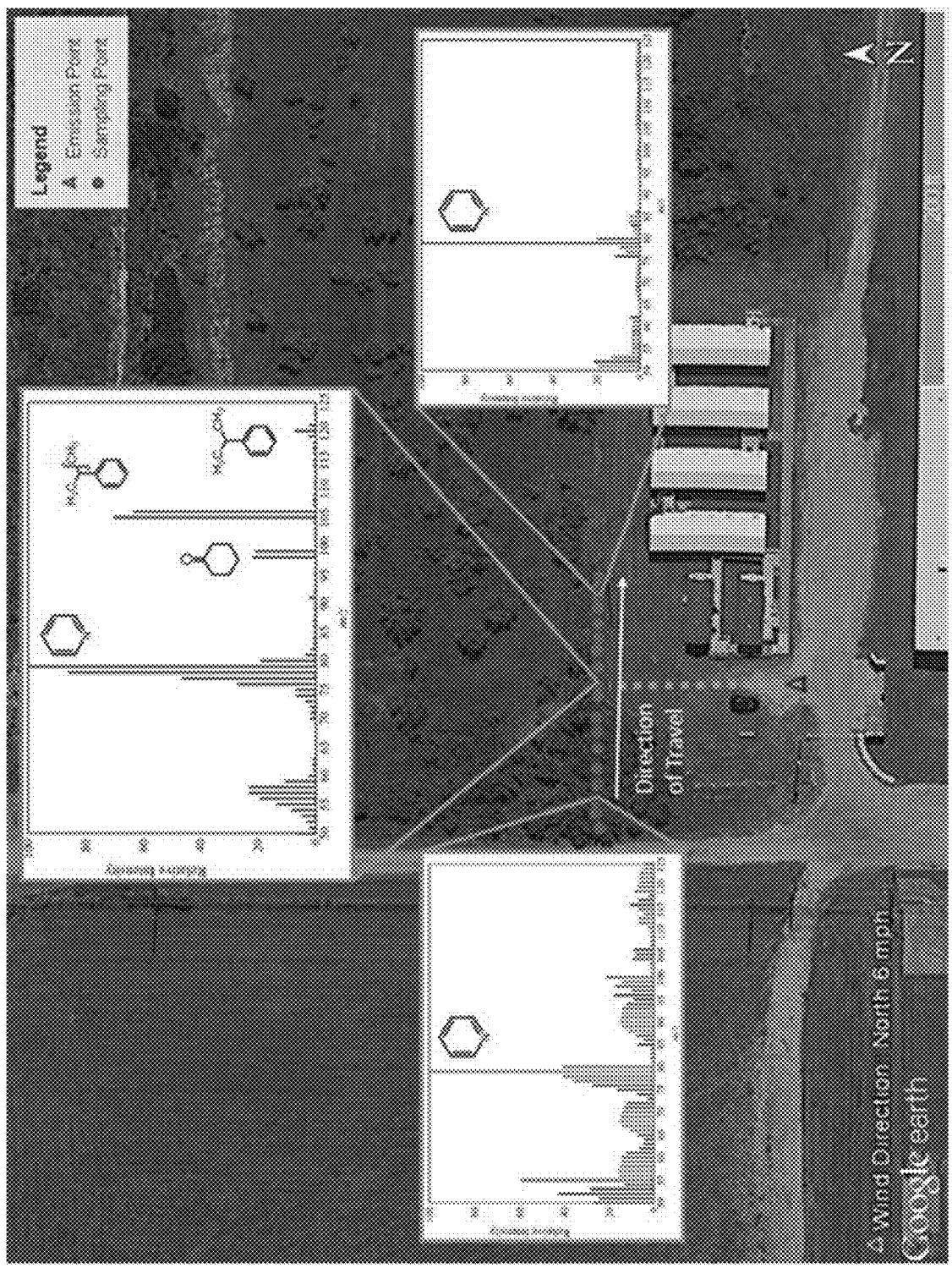
FIG. 8 shows the emission of pyridine, cyclohexanone, and isopropylbenzene, as illustrated in FIG. 3, and subsequent downwind detection.

For example, FIG. 8 shows the results of sampling according to embodiments in an environment where three chemicals were emitted and subsequently detected downwind. Approximately 100 mL of tracer chemicals were emitted and subsequently detected. Pyridine (79 m/z) was the most scattered in the sampling region. While centerline, or near centerline, mass spectra indicated the presence of isopropylbenzene (120 m/z) and associated ethylbenzene fragment (105 m/z), further confirmation of centerline detection included cyclohexanone (98 m/z). The degree of dispersal along the detection path is small due to the short distance (107 ft). Relative intensity spectra were used to illustrate the obtained datasets, as the most intense peak confirms the most disperse and most volatile chemical interest, in the highest concentration. Higher intensities off-center may be indicative of the volatility of the chemical of interest and its ability to be dispersed in the atmosphere. Increasing peaks as an operator approaches a center is helpful to confirm downwind dispersal and centering of normal distribution position.

Tabled atmospheric stability constants for I, J, and K, (see equations 15 and 16 above), were determined for up to 10 km distances. It may be assumed that at such distances downwind and limited exhausting of detectable chemical interests has minimal impact on the usefulness of this model. Dispersion of chemical interests at distances over 10 km would result in concentrations currently below the threshold of detection, but concentration of the sample or more sensitive detectors make higher distances possible.

Membrane response and diffusion of chemicals into the vacuum of the mass spectrometer may effect time of detection. Detected Gaussian dispersions may be shifted in the direction of travel, as the vehicle is still moving while diffusion is occurring. Noting the speed of travel and creating an average diffusion for a class of chemicals that are permeable for a given membrane composition, the location of detection can be back calculated according to embodiments. Operating at slower speeds reduces the amount of distance traveled before detection. As a series of locations or sampling points may be obtained and time-stamped during sampling of an environment, and observed spectra may be attributed to a spatial position that better corresponds to speed of travel and membrane response time.

The empirical values may be solved using Equation 14. These values have been evaluated to contain a 4% maximum error when approximating the standard distribution from the Gaussian. Values generally averaged about 1% error on the horizontal standard deviation, and 2% on the vertical deviation. While partings from a given value of this magnitude should be considered significant, the 4% wider Gaussian has been found herein to have a minimal effect on the mathematical calculation. Greater variance can be expected from personnel extracting atmospheric values differently.

In an embodiment, the reverse gas stack modeling device 200 of FIG. 2 may include one or more environmental sensors (not shown in FIG. 2). The one or more environmental sensors may be adapted to generate environmental data comprising wind speed data, wind direction data, ambient temperature data, barometric pressure data, other types of environmental data or a combination thereof. In an additional or alternative embodiment, the reverse gas stack modeling device 200 may include a communication interface configured to communicatively couple the reverse gas stack modeling device 200 to a network, and the environmental data may be received from a third party source, such as a third party weather service, via a communication link (e.g., a wired or wireless communication link). The environmental data may be used by the one or more processors to predict the location of the source of the one or more target molecules. For example, the wind speed and direction data may be utilized to determine the reverse gas stack model with the Gaussian dispersion for the one or more target molecules over the one or more sampled locations, as described above with respect to Equations 1-17.

In an embodiment, the database(s) 242 may store infrastructure data associated with the one or more sampled locations. The infrastructure data may comprise information identifying water infrastructure, electrical infrastructure, buildings, sewage infrastructure, other types of infrastructure (e.g., natural gas and/or oil pipelines, etc.), or a combination thereof located proximate to the one or more sampled locations. The infrastructure data may be utilized by the one or more processors 210 to predict the location of the source of the one or more target molecules based on the infrastructure data by eliminating or enhancing an area for the source, as described above.

As explained above, the reverse gas stack modeling device 200 provides new techniques for analyzing molecule dispersion, such as enabling a point source of molecules or effluent to be identified. It is noted that embodiments may be adapted to predict the source in two dimensions (e.g., determine a bounded area predicted to contain the source) or three dimensions (e.g., determine a bounded area predicted to contain the source as well as a prediction as to the elevation of the source). This may provide substantial benefit in urban environments, such as where numerous multi-story building may be in close proximity.

Figure 9:
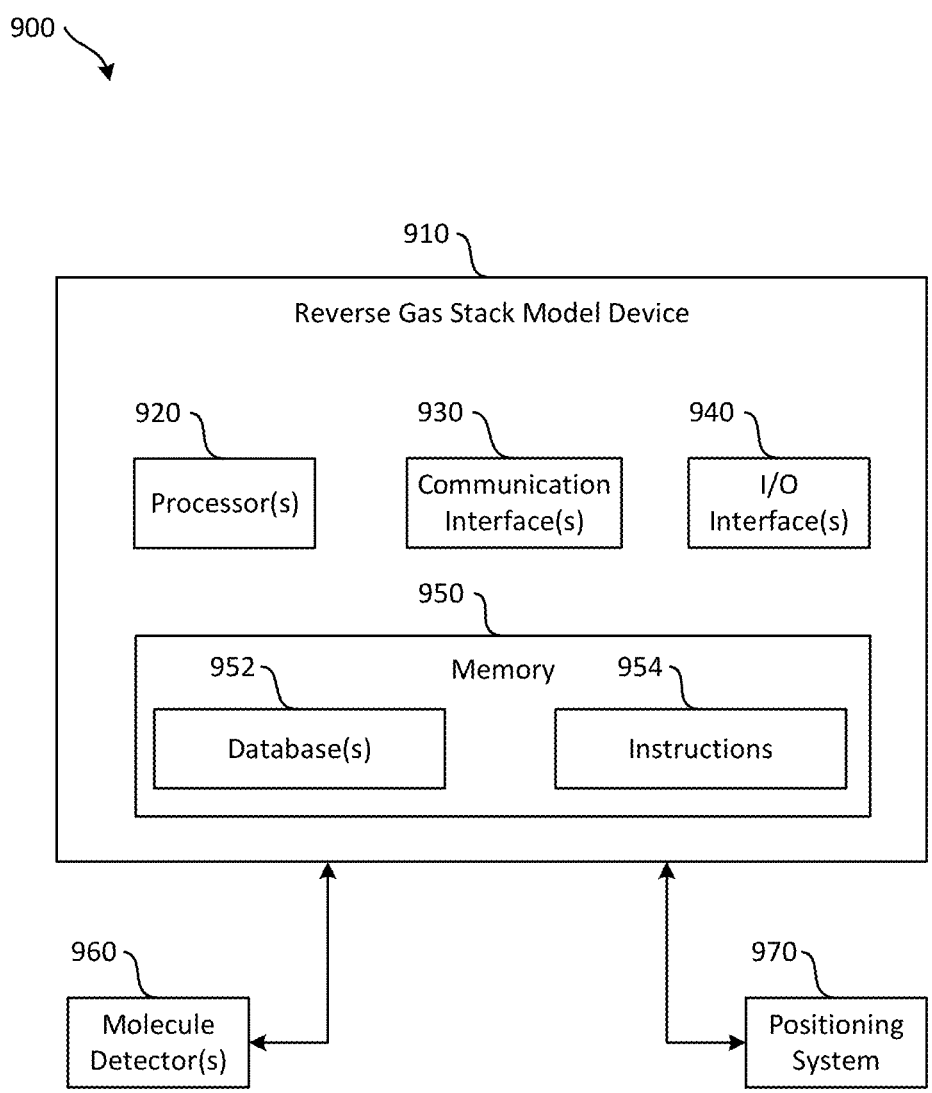
FIG. 9 is a block diagram illustrating a modular system of devices for locating a source of one or more target molecules in accordance with embodiments of the present disclosure.

Referring to FIG. 9, a block diagram illustrating an exemplary modular system of devices for locating a source of one or more target molecules in accordance with embodiments of the present disclosure is shown as a modular system 900. As shown in FIG. 9, the exemplary modular system 900 may include reverse gas stack modeling device 910 and various modules communicatively coupled thereto. The reverse gas stack modeling device 910 may include one or more processors 920, one or more communication interfaces 930, I/O interfaces 940, and memory 950. Memory 950 may store one or more databases 952 and instructions 954. The instructions 954 may be executed by the one or more processors 920 to locate a source of one or more target molecules in accordance with embodiments of the present disclosure. Additionally, as shown in FIG. 9, the modular system 900 includes one or more molecule detectors 960 and positioning system 970 communicatively coupled to the reverse gas stack modeling device 910. In an embodiment, the one or more molecule detectors 960 and the positioning system 970 may be communicatively coupled to the reverse gas stack modeling device 910 via one or more communication interfaces 930 (e.g., via a wired or wireless communication network) and/or one or more of the I/O interfaces 940 (e.g., a Universal Serial Bus (USB) interface, a serial interface, a memory card interface, and the like).

It is noted that although shown as separate devices, in some embodiments, the one or more molecule detectors 960 and the positioning system 970 may be integrated into a single data collection device configured to sample and environment at one or more locations and then provide the collected data (e.g., information representative of the presence of one or more molecules detected at one or more sample locations in an environment and location data corresponding to each of the one or more sample locations). For example, the one or more molecule detectors 960 and the positioning system 970 may be integrated within a vehicle or other mobile platform (e.g., the mobile platform described above with reference to FIG. 2) and may traverse an environment to obtain samples at one or more locations within the environment. As the samples are collected, the information representative of one or more molecules detected at one or more sample locations in an environment may be generated by the one or more molecule detectors 960, and the location data corresponding to each of the one or more sampled locations may be generated by the positioning system 970. Subsequently, the collection device may be communicatively coupled to the reverse gas stack modeling device 910 to upload the collected information to the reverse gas stack modeling device 910. In an embodiment, the collected information may be stored at the database(s) 952. In an embodiment, the collected information may be timestamped, as described above with reference to FIG. 2, which may enable the one or more processors 920 to correlate each of the samples included the information representative of the presence of one or more molecules detected at one or more sample locations to the corresponding location data for each of the one or more sampled locations.

In an embodiment, the one or more molecule detectors 960 may be substantially similar to the one or more molecule detectors 220 of FIG. 2. For example, the one or more target molecules detectable by the one or more molecule detectors 960 may be associated with one or more chemicals produced by, or as a byproduct of production processes performed at, clandestine laboratories, environmental threats, hazardous spills, environmental pollutants, effluent chemicals, chemical weapon deployments, or a combination thereof. In an embodiment, the one or more molecule detectors 960 may comprise at least one heavy molecule detector. In an additional or alternative embodiment, the one or more molecule detectors 960 may comprise one or more Raman spectrometers, infrared (IR) spectrometers, chemical sensors, mass spectrometers, or a combination thereof. In an embodiment, the one or more molecule detectors 960 may comprise specific detectors for one or more types of molecules associated with chemicals comprising polycyclic aromatic hydrocarbon emissions (PAHs), benzene, alkyl benzene, chlorobenzene, or trichlorobenzene, isopropylbenzene, ethylbenzene, cyclohexanone, xylene, p-cymene, hydrocarbons produced by oil and gas exploration or extraction, methane, ethane, propane, butane, pentane, hexane, toluene, trichloroethene, chloroform, tetrachloroethane, 1,1,1-trichloroethane, 1,1,2,2-tetrachloroethane, xylene, carbon tetrachloride, 1,1-dichloroethane, or 1,2-dichloroethane. It is noted that, in some embodiments, detectors for one or more other types of molecules may also be provided depending on the particular molecules for which the system 900 is configured to detect, and that the molecules listed above are provided for purposes of illustration, rather than by way of limitation. For example, the system 900 may be configured to detect both aromatic and non-aromatic molecules, and other hydrocarbon molecules of interest. In an embodiment, the system 900 may comprise one or more pumps (not shown in FIG. 9) configured to increase a volume of sample tested by the one or more molecule detectors 960.

In an embodiment, the positioning system 970 may comprise a global positioning system (GPS). In an additional or alternative embodiment, the positioning system 970 may comprise a telecommunications-based positioning system, such as a positioning system that uses cellular communication system (e.g., cellular base stations, access points or other wireless communication technologies) to determine a position for a respective sample. In still another additional or alternative embodiment, the positioning system 970 may comprise a local positioning system. For example, when the scanning or sampling of an environment is not capable of utilizing GPS or telecommunications-based positioning technologies (e.g., because the sampling is performed inside a building or underground where signals necessary for obtaining positioning information using GPS and telecommunications-based technologies cannot be reliably obtained), a local coordinate system may be used, and the local coordinate system may be subsequently mapped to "real-world" coordinates. This may be done by configuring the local coordinate system such that at least one point in the local coordinate system corresponds to a location known in "real-world" coordinates, and the mapping the coordinates obtained in the local coordinate system to "real-world" coordinates based on the at least one point having a location known in both the local coordinate system and "real-world" coordinates. When a local coordinate system is used, the positioning system 970 may comprise one or more accelerometers and/or gyroscopes which can be utilized to measure linear and rotational acceleration and/or velocity of the positioning system 970 (or collection device) during the sampling. In an embodiment, the positioning system 970 may comprise a combination of these different systems and/or other positioning systems not described herein for simplicity of the disclosure.

In an embodiment, the one or more processors 920 may initiate and control the sampling. For example, the instructions 954 may provide an application that may be executed by the one or more processors 920 to initiate and control the sampling by the one or more molecule detectors 960 and to obtain the location information from the positioning system 970. For example, when sampling is to be performed, the one or more molecule detectors 960 and the positioning system 970 may be coupled to the reverse gas stack modeling device 910 to form the system 900, which may be operable to sample an environment, obtain location information associated with the locations where samples are obtained, and perform operations to determine a source of the one or more target molecules using the techniques described herein. In an additional or alternative embodiment, the one or more molecule detectors 960 and the positioning system 970 may be controlled separate from the reverse gas stack modeling device 910 (e.g., the one or more molecule detectors 960 and the positioning system 970 may be operated independent of the reverse gas stack modeling device 910 during the sampling). The one or more processors 920 may be configured to receive the information representative of the presence of one or more target molecules based on one or more samples of an environment and the location information, and to determine, based on the information representative of the presence of one or more molecules and the location information, a dynamic reverse gas stack model for the one or more target molecules over the one or more sampled locations. In an embodiment, the dynamic reverse gas stack model may have a Gaussian dispersion for the one or more target molecules over the one or more sampled locations. In an embodiment, this information may be received directly from the one or more molecule detectors 960 and the positioning system 970. For example, the one or more molecule detectors 960 may transmit or otherwise provide the information representative of the presence of one or more target molecules based on one or more samples of an environment and the positioning system 970 may provide the location information to the one or more processors 920 of the reverse gas stack modeling device 900 or the database(s) 952 upon being communicatively coupled to the reverse gas stack modeling device 910, where the communicative coupling may occur subsequent to the sampling by the one or more molecule detectors 960 and the position determinations by the positioning system 970. When the information is provided to the database(s) 952, it may be retrieved by the one or more processors 920 in response to an input requesting generation of the dynamic reverse gas stack model for the one or more target molecules. In an embodiment, the dynamic reverse gas stack model for the one or more target molecules may be generated by the one or more processors 920 as described above with respect to Equations 1-17, and may be output to, or presented at, one of the I/O devices 940, such as a display device. After calculating the dynamic reverse gas stack model with the Gaussian dispersion for the one or more target molecules over the one or more sampled locations, the one or more processors 920 may predict a location for a source of the one or more target molecules based on the dynamic reverse gas stack model, which may be displayed to a user of the reverse gas stack modeling device 910.

In an embodiment, the modular system 900 may include one or more environmental sensors (not shown in FIG. 9). The one or more environmental sensors may be adapted to generate environmental data comprising wind speed data, wind direction data, ambient temperature data, barometric pressure data, other types of environmental data or a combination thereof. In an additional or alternative embodiment, the reverse gas stack modeling device 910 may receive (or retrieve) from a third party source, such as a third party weather service, via a communication link (e.g., a wired or wireless communication link). The environmental data may be retrieved, at least in part, based on the position data, which may indicate particular locations and times for which environmental data is needed. The environmental data may be used by the one or more processors 920 to predict the location of the source of the one or more target molecules. For example, the wind speed and direction data may be utilized to calculate the reverse gas stack model with the Gaussian dispersion for the one or more target molecules over the one or more sampled locations, as described above with respect to Equations 1-17.

In an embodiment, the database(s) 952 may store infrastructure data associated with the one or more sampled locations. The infrastructure data may comprise information identifying water infrastructure, electrical infrastructure, buildings, sewage infrastructure, other types of infrastructure (e.g., natural gas and/or oil pipelines, etc.), or a combination thereof located proximate to the one or more sampled locations. The infrastructure data may be utilized by the one or more processors 920 to predict the location of the source of the one or more target molecules based on the infrastructure data by eliminating or enhancing an area for the source, as described above. It is noted that in some embodiments, the database(s) 952 may be stored external to the reverse gas stack modeling device 910. For example, a network attached storage (NAS) device, database server, or other form of network addressable storage may be utilized in the modular system 900 to provide the database(s) 952.

As explained above, the modular system 900 provides new techniques for analyzing molecule dispersion, such as enabling a point source of molecules or effluent to be identified. It is noted that embodiments may be adapted to predict the source in two dimensions (e.g., determine a bounded area predicted to contain the source) or three dimensions (e.g., determine a bounded area predicted to contain the source as well as a prediction as to the elevation of the source). This may provide substantial benefit in urban environments, such as where numerous multistory building may be in close proximity. Further, by providing the system 900 as a modular system, the modular system 900 may provide increased flexibility in terms of deployment. For example, a collection device (e.g., a drone, a robot, and the like) may be equipped with the one or more molecule detectors and the positioning system and then deployed to an area or environment for sampling purposes. Once the environment has been sampled, or during the sampling, data associated with the sampling (e.g., the observed concentrations of the one or more target molecules and the location information) may be provided to the reverse gas stack modeling device 910 and the source of the one or more molecules may be identified. Further, in a modular system deployment, the collection device (e.g., the device used to perform the sampling) may be smaller and cheaper (e.g., because the processing resources and hardware for calculating the reverse gas stack model are provided on a separate device). This may be beneficial in deployments where damage to the collection device(s) may occur during the sampling, and may prevent data loss (e.g., because the collected information may be streamed to the reverse gas stack modeling device during the sampling via a network). Further, in embodiments of a modular system, such as the modular system 900 of FIG. 9, the one or more molecule detectors may be interchangeable, allowing rapid deployment of the molecule detectors for different purposes. For example, because each of the one or more molecule detectors 960 may be configured to detect a particular set of one or more target molecules. The different molecule detectors, each configured to detect different molecules or sets of molecules, may be deployed for sampling an environment without requiring reconfiguration of the entire sampling system setup (e.g., changing inlet membranes, etc.). In other embodiments, a modular system may be reconfigured to detect new target molecules by changing one or more aspects of the one or more detectors 960, such as changing inlet membranes, and the like, however, such processes may introduce delay in the sampling of an environment as compared to embodiments that utilize different detector modules separately, which may be deployed in a more "plug-and-play" type deployments.

Figure 10:
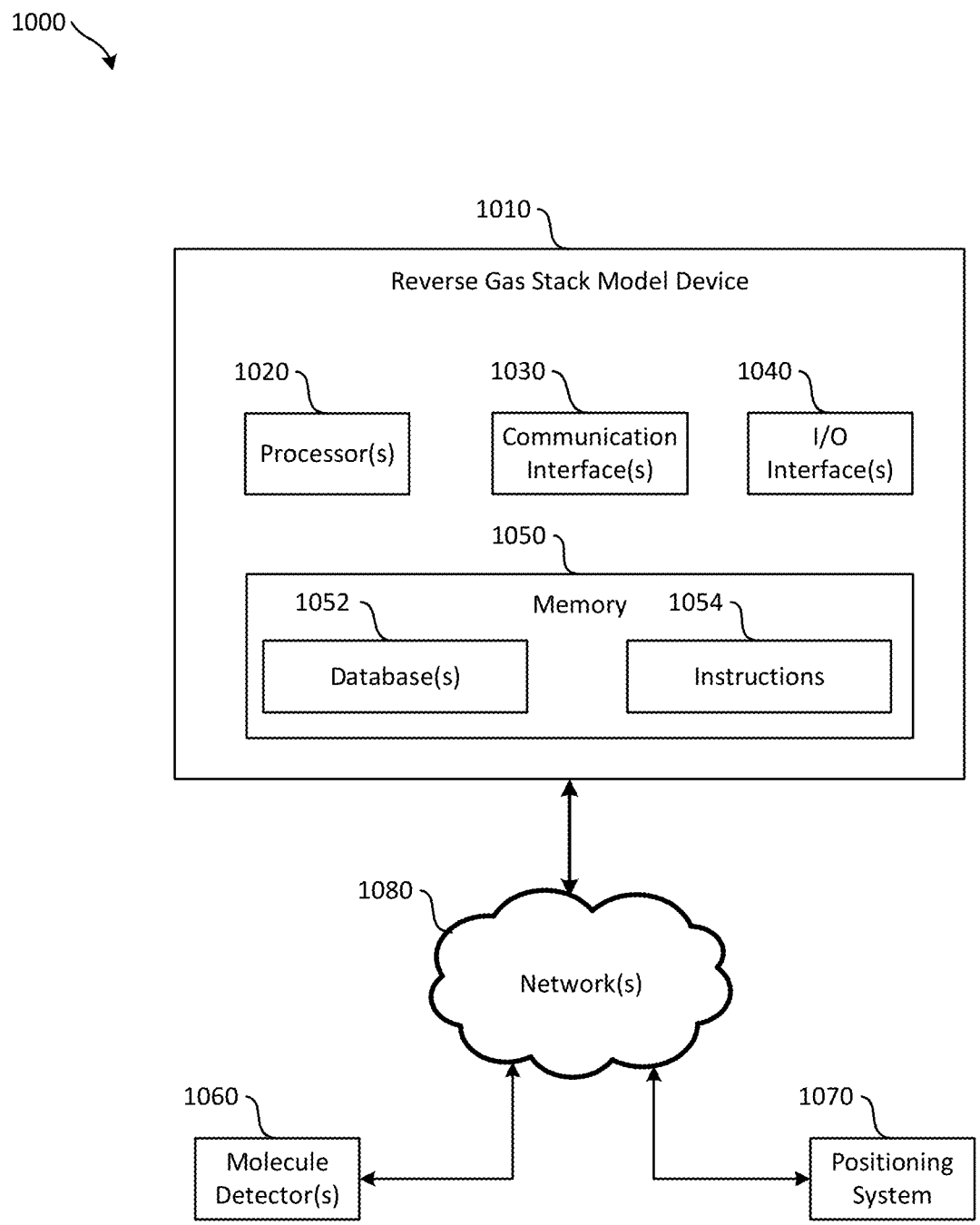
FIG. 10 is a block diagram illustrating a cloud-based system for locating a locating source of one or more target molecules in accordance with embodiments of the present disclosure.

Referring to FIG. 10, a block diagram of an exemplary cloud-based system for locating a source of one or more target molecules in accordance with embodiments of the present disclosure is shown as a cloud-based system 1000. As shown in FIG. 10, the cloud-based system 1000 may include a reverse gas stack modelling device 1010 and various modules communicatively coupled thereto via one or more networks 1080. In one embodiment, the reverse gas stack modelling device 1010 may include one or more processors 1020, one or more communication interfaces 1030, I/O interfaces 1040, and memory 1050. Memory 1050 may further include one or more databases 1052 and instructions 1054. The instructions 1054 may be executed by the one or more processors 1020 to locate a source of one or more target molecules in accordance with embodiments of the present disclosure, as described above with reference to FIGS. 2 and 9, and Equations 1-17. The cloud-based system 1000 may also comprise one or more molecule detectors 1060 and a positioning system 1070. As shown in FIG. 10, in the cloud-based system 1000, the one or more molecule detectors 1060 and the positioning system 1070 may be communicatively coupled to the reverse gas stack modelling device 1010 via the one or more networks 1080.

It is noted that although shown as separate devices, in some embodiments, the one or more molecule detectors 1060 and the positioning system 1070 may be integrated into a single data collection device configured to sample and environment at one or more locations and then provide the collected data (e.g., information representative of the presence of one or more molecules detected at one or more sample locations in an environment and location data corresponding to each of the one or more sample locations). For example, the one or more molecule detectors 1060 and the positioning system 1070 may be integrated within a vehicle or other mobile platform (e.g., the mobile platform described above with reference to FIG. 2) and may traverse an environment to obtain samples at one or more locations within the environment. As the samples are collected, the information representative of one or more molecules detected at one or more sample locations in an environment may be generated by the one or more molecule detectors 1060, and the location data corresponding to each of the one or more sample locations may be generated by the positioning system 1070. Subsequently, the collection device may be communicatively coupled to the reverse gas stack modeling device 1010 to upload the collected information to the reverse gas stack modeling device 1010. In an embodiment, the collected information may be stored at the database(s) 1052. In an embodiment, the collected information may be timestamped, as described above with reference to FIG. 2, which may enable the one or more processors 1020 to correlate each of the samples included the information representative of the presence of one or more molecules detected at one or more sample locations to the corresponding location data for each of the one or more sample locations.

In an embodiment, the one or more molecule detectors 1060 may be substantially similar to the one or more molecule detectors 220 of FIG. 2. For example, the one or more target molecules detectable by the one or more molecule detectors 1060 may be associated with one or more chemicals produced by, or as a byproduct of production processes performed at, clandestine laboratories, environmental threats, hazardous spills, environmental pollutants, effluent chemicals, chemical weapon deployments, or a combination thereof. In an embodiment, the one or more molecule detectors 1060 may comprise at least one heavy molecule detector. In an additional or alternative embodiment, the one or more molecule detectors 1060 may comprise one or more Raman spectrometers, infrared (IR) spectrometers, chemical sensors, mass spectrometers, or a combination thereof. In an embodiment, the one or more molecule detectors 1060 may comprise specific detectors for one or more types of molecules associated with chemicals comprising polycyclic aromatic hydrocarbon emissions (PAHs), benzene, alkyl benzene, chlorobenzene, or trichlorobenzene, isopropylbenzene, ethylbenzene, cyclohexanone, xylene, p-cymene, hydrocarbons produced by oil and gas exploration or extraction, methane, ethane, propane, butane, pentane, hexane, toluene, trichloroethene, chloroform, tetrachloroethane, 1,1,1-trichloroethane, 1,1,2,2-tetrachloroethane, xylene, carbon tetrachloride, 1,1-dichloroethane, or 1,2-dichloroethane. It is noted that, in some embodiments, detectors for one or more other types of molecules may also be provided depending on the particular molecules for which the system 1000 is configured to detect, and that the molecules listed above are provided for purposes of illustration, rather than by way of limitation. For example, the system 1000 may be configured to detect both aromatic and non-aromatic molecules, as well as other types of hydrocarbon molecules. In an embodiment, the system 1000 may comprise one or more pumps (not shown in FIG. 10) configured to increase a volume of sample tested by the one or more molecule detectors.

In an embodiment, the positioning system 1070 may comprise a global positioning system (GPS). In an additional or alternative embodiment, the positioning system 1070 may comprise a telecommunications-based positioning system, such as a positioning system that uses cellular communication system (e.g., cellular base stations, access points or other wireless communication technologies) to determine a position for a respective sample. In still another additional or alternative embodiment, the positioning system 1070 may comprise a local positioning system. For example, when the scanning or sampling of an environment is not capable of utilizing GPS or telecommunications-based positioning technologies (e.g., because the sampling is performed inside a building or underground where signals necessary for obtaining positioning information using GPS and telecommunications-based technologies cannot be reliably obtained), a local coordinate system may be used, and the local coordinate system may be subsequently mapped to "real-world" coordinates. This may be done by configuring the local coordinate system such that at least one point in the local coordinate system corresponds to a location known in "real-world" coordinates, and the mapping the coordinates obtained in the local coordinate system to "real-world" coordinates based on the at least one point having a location known in both the local coordinate system and "real-world" coordinates. When a local coordinate system is used, the positioning system 1070 may comprise one or more accelerometers and/or gyroscopes which can be utilized to measure linear and rotational acceleration and/or velocity of the positioning system 1070 (or collection device) during the sampling. In an embodiment, the positioning system 1070 may comprise a combination of these different systems and/or other positioning systems not described herein for simplicity of the disclosure.

In an embodiment, the one or more processors 1020 may initiate and control the sampling. For example, the instructions 1054 may provide an application that may be executed by the one or more processors 1020 to initiate and control the sampling by the one or more molecule detectors 1060 and to obtain the location information from the positioning system 1070. For example, when sampling is to be performed, the one or more processors 1020 may receive an input instructing the one or more processors to initiate sampling of an environment, and the reverse gas stack modeling device may transmit a signal to the one or more molecule detectors 1060 and the positioning system 1070 via the one or more networks 1080 instructing these devices to sample the environment at one or more locations and to obtain location information associated with the locations where samples are obtained. In an additional or alternative embodiment, the one or more molecule detectors 1060 and the positioning system 1070 may be controlled separate from the reverse gas stack modeling device 1010 (e.g., the one or more molecule detectors 1060 and the positioning system 1070 may be operated independent of the reverse gas stack modeling device 1010 during the sampling), and may subsequently transmit the information representative of the presence of one or more target molecules based on one or more samples of an environment and the location information to the one or more processors 1020 and/or the database(s) 1052. The one or more processors 1020 may be configured to receive the information representative of the presence of one or more target molecules based on one or more samples of an environment and the location information, and to calculate, based on the information representative of the presence of one or more molecules and the location information, a dynamic reverse gas stack model for the one or more target molecules over the one or more sampled locations. In an embodiment, the dynamic reverse gas stack model may have a Gaussian dispersion for the one or more target molecules over the one or more sampled locations. When the information is provided to the database(s) 1052, it may be retrieved by the one or more processors 1020 in response to an input requesting generation of the dynamic reverse gas stack model for the one or more target molecules over the one or more sampled locations. In an embodiment, the dynamic reverse gas stack model for the one or more target molecules over the one or more sampled locations may be generated by the one or more processors 1020 as described above with respect to Equations 1-17, and may be output to, or presented at, one of the I/O devices 1040, such as a display device. After calculating the dynamic reverse gas stack model with the Gaussian dispersion for the one or more target molecules over the one or more sampled locations, the one or more processors 1020 may predict a location for a source of the one or more target molecules based on the dynamic reverse gas stack model, which may be displayed to a user of the reverse gas stack modeling device 1010.

In an embodiment, the cloud-based system 1000 may include one or more environmental sensors (not shown in FIG. 10). The one or more environmental sensors may be adapted to generate environmental data comprising wind speed data, wind direction data, ambient temperature data, barometric pressure data, other types of environmental data or a combination thereof. In an additional or alternative embodiment, the reverse gas stack modeling device 1010 may receive (or retrieve) from a third party source, such as a third party weather service, via a communication link (e.g., a wired or wireless communication link). The environmental data may be retrieved, at least in part, based on the position data, which may indicate particular locations and times for which environmental data is needed. The environmental data may be used by the one or more processors 1020 to predict the location of the source of the one or more target molecules. For example, the wind speed and direction data may be utilized to calculate the reverse gas stack model with the Gaussian dispersion for the one or more target molecules over the one or more sampled locations, as described above with respect to Equations 1-17.

In an embodiment, the database(s) 1052 may store infrastructure data associated with the one or more sampled locations. The infrastructure data may comprise information identifying water infrastructure, electrical infrastructure, buildings, sewage infrastructure, other types of infrastructure (e.g., natural gas and/or oil pipelines, etc.), or a combination thereof located proximate to the one or more sampled locations. The infrastructure data may be utilized by the one or more processors 1020 to predict the location of the source of the one or more target molecules based on the infrastructure data by eliminating or enhancing an area for the source, as described above. It is noted that in some embodiments, the database(s) 1052 may be stored external to the reverse gas stack modeling device 1010. For example, a NAS device, database server, or other form of network addressable storage may be utilized in the cloud-based system 1000 to provide the database(s) 1052.

As explained above, the cloud-based system 1000 provides new techniques for analyzing molecule dispersion, such as enabling a point source of molecules or effluent to be identified. It is noted that embodiments may be adapted to predict the source in two dimensions (e.g., determine a bounded area predicted to contain the source) or three dimensions (e.g., determine a bounded area predicted to contain the source as well as a prediction as to the elevation of the source). This may provide substantial benefit in urban environments, such as where numerous multistory building may be in close proximity. Further, by providing the system 1000 as a cloud-based system, the cloud-based system 1000 may provide increased flexibility in terms of deployment. For example, a collection device (e.g., a drone, a robot, and the like) may be equipped with the one or more molecule detectors and the positioning system and then deployed to an area or environment for sampling purposes. Once the environment has been sampled, or during the sampling, data associated with the sampling may be provided to the reverse gas stack modeling device 1010 and the source of the one or more molecules may be identified. Further, in a cloud-based system deployment, the collection device (e.g., the device used to perform the sampling) may be smaller and cheaper (e.g., because the processing resources and hardware for calculating the reverse gas stack model are provided on a separate device). This may be beneficial in deployments where damage to the collection device(s) may occur during the sampling, and may prevent data loss (e.g., because the collected information may be streamed to the reverse gas stack modeling device during the sampling via a network). The cloud-based system 1000 may operate to determine or predict a location of a source for the one or more target molecules in a manner substantially similar to the flow of operations described above with respect to FIGS. 2 and 9 and Equations 1-17, and those processes and flows are not repeated here. The cloud-based system 1000 may provide several advantages over those embodiments due to its deployment configuration. For example, in cloud-based systems, computational and data storage resources reside in a network-based deployment configuration. Thus, the cloud-based system 1000 may be more easily scaled to provide the appropriate level of computational and data storage resources required for a particular deployment. Further, cloud-based systems may provide increased access to the system and may provide increased data redundancy and/or resiliency. Further, it is noted that in some deployments of the cloud-based system 1000, one or more components may be eliminated. For example, as explained in more detail below with reference to FIG. 11, in some system deployment configurations utilizing cloud-based reverse gas stack modeling devices, the positioning system 1070 may be removed (e.g., when the one or more molecule detectors 1060 are placed at known locations during the sampling of the environment.

Figure 11:
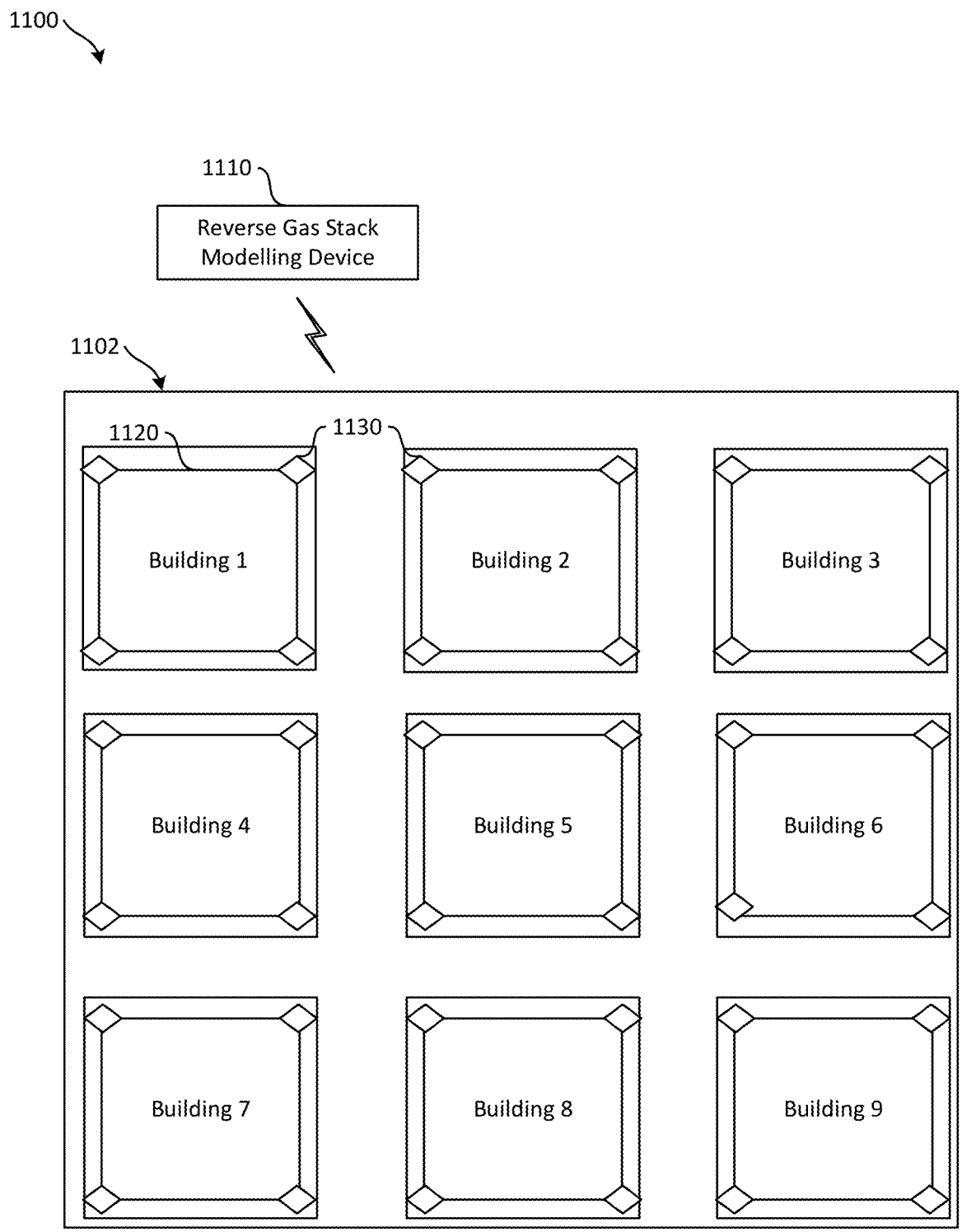
FIG. 11 is a block diagram illustrating another system for locating a source of one or more target molecules in accordance with embodiments of the present disclosure.

Referring to FIG. 11, a block diagram of another exemplary cloud-based system for locating a source of one or more target molecules in accordance with embodiments of the present disclosure is shown as a cloud-based system 1100. As shown in FIG. 11, the cloud-based system 1100 may include a reverse gas stack modelling device 1110 and one or more molecule detectors 1130. The cloud-based system 1100 may operate in substantially the same manner as the cloud-based system 1000 described above with reference to FIG. 10, however, in the cloud-based system 1100 of FIG. 11, the one or more molecule detectors 1130 have been deployed at known locations, allowing the positioning system to be omitted. For example, in FIG. 11, the one or more molecule detectors have been placed at various locations within a portion of a city 1102, such as on one or more corners of buildings 1120. It is noted that the cloud-based system 1100 illustrated in FIG. 11 shows molecule detectors 1130 located at each corner of every building 1120 for purposes of illustration, rather than by way of limitation, and embodiments of the present disclosure should not be limited to a particular number or arrangement of molecule detectors placed at a particular building. For example, in some embodiments, the molecule detectors 1130 may be placed on every other building or some other arrangement suitable for providing a grid of molecule detectors capable of sampling an environment (e.g., the portion of the city 1102) for the presence of one or more target molecules in accordance with embodiments of the present disclosure.

As briefly described above, each of the molecule detectors 1130 may be placed at a known location within the environment. In an embodiment, the molecule detectors 1130 may be permanently installed in the environment (e.g., where the molecule detectors 1130 are to be used for continuous monitoring of the environment). In an additional or alternative embodiment, the molecule detectors may be temporarily placed at known locations to facilitate sampling of the environment, and may be moved or removed once the sampling is complete. It is noted that permanently installed molecule detectors may find particular utility in embodiments where periodic and rapid testing of an environment may be beneficial, such as at refineries, chemical and oil production facilities, cities, and the like. Further, temporarily deployed molecule detectors may be more suited for other types of environments, such as concert venues, festival venues, or other environments where continuous sampling is not needed.

Because each of the molecule detectors may be deployed at a known location (e.g., a location which may initially be determined using a positioning system at the time each molecule detector is installed), a positioning system is not required during operation of the cloud-based system 1100 to sample an environment. Rather, the known locations of the molecule detectors may be stored in a database (e.g., a database accessible to the reverse gas stack modeling device 1110), and the reverse gas stack modeling device 1110 may be operable to correlate the information representative of one or more target molecules in the environment 1102 to particular known locations of the molecule detectors 1130 during calculation of the source of the one or more target molecules. Each of the molecule detectors 1130 may be communicatively coupled to the reverse gas stack modelling device 1110 (e.g., via communication interfaces, one or more I/O interfaces, one or more networks), and the like. In an embodiment, at least two of the molecule detectors 1130 may be deployed at different elevations. This may enable sampling of the environment in a manner that provides a more detailed view of the one or more target molecules present within the sampled environment, and may facilitate more accurate calculations of the source of the one or more target molecules. It is noted that although the molecule detectors 1130 are illustrated as being placed at corners of buildings, embodiments of the present disclosure are not to be limited to such deployments. Rather, the known locations may be any location within the environment to be sampled including, but not limited to, street lamps and signs, sewer and subway systems, or other infrastructure present within the environment to be sampled. Upon obtaining the information representative of the one or more target molecules present in the sampled environment, the reverse gas stack modeling device 1110 may calculate a dynamic reverse gas stack model for the one or more target molecules over the one or more sampled locations. In an embodiment, the dynamic reverse gas stack model may have a Gaussian dispersion for the one or more target molecules over the one or more sampled locations. In an embodiment, the dynamic reverse gas stack model for the one or more target molecules over the one or more sampled locations may be generated by one or more processors of the reverse gas stack modeling device 1110, as described above with respect to Equations 1-17, and may be output to, or presented at, an I/O device, such as a display device, communicatively coupled to the reverse gas stack modeling device 1110. After calculating the dynamic reverse gas stack model with the Gaussian dispersion for the one or more target molecules over the one or more sampled locations, the reverse gas stack modeling device 1110 may predict a location for a source of the one or more target molecules based on the dynamic reverse gas stack model, which may be displayed to a user of the reverse gas stack modeling device 1110.

Further, it is noted that in some embodiments of the cloud-based system 1100, a combination of molecule detectors deployed at known locations and molecule detectors provided via a mobile platform may be utilized during the sampling. For example, the molecule detectors 1130 may be deployed sparsely in the environment and, upon detecting the presence of a particular target molecule within a particular portion of the environment, a mobile platform (e.g., the reverse gas stack modeling device 200 of FIG. 2 or the modular system 900 of FIG. 9) may be utilized to perform a thorough sampling of the particular portion of the environment where the one or more target molecules were detected. Such an embodiment may provide for rapid notification of the presence of one or more target molecules, and may enable the location where the one or more target molecules are present to be sampled more quickly, which may improve safety (e.g., by discovering a potential threat or hazard quickly).

Further, it is noted that in addition to deploying the molecule detectors 1130, in some embodiments, the cloud-based system 1100 may include one or more environmental sensors (not shown in FIG. 11) for providing environmental data that may be used by the reverse gas stack modeling device 1110 to predict or revise the location of the source for the one or more target molecules, as described above. In an additional or alternative embodiment, the cloud-based system 1100 may integrate environmental data (e.g., wind speed, direction, temp, barometric pressure, etc.), or infrastructure data (e.g., water, electrical, sewage, gas, buildings, etc.), or both to narrow or refine a potential point of source for the effluent stream during the initial determination of the dynamic reverse gas stack model. In an additional or alternative embodiment, the reverse gas modeling device 1110 may retrieve the environmental data from an external source or service based on the known locations and times when the samples were obtained. In an embodiment, the cloud-based system 1100 may further utilize infrastructure information to predict, determine, or revise the location of the source for the one or more target molecules, as described above.

Figure 12:
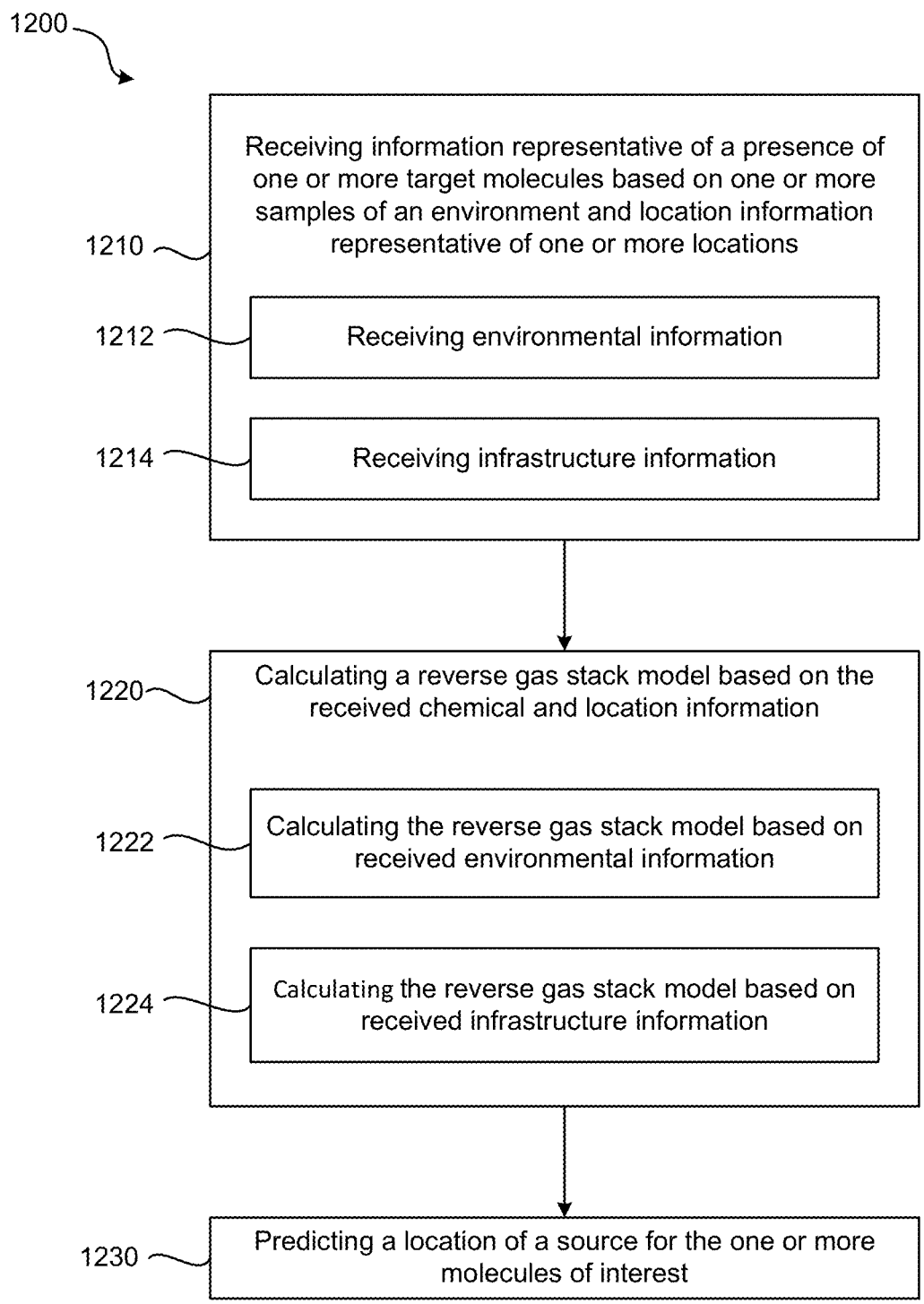
FIG. 12 is a flow diagram of a method for locating threat and point-of-source from effluent streams according to an embodiment of the present invention.

Referring to FIG. 12, a flow diagram of a method for locating threat and point-of-source from effluent streams in accordance with an embodiment of the present disclosure is shown as a method 1200. In an embodiment, the method 1200 may correspond to the flow of operations described above with respect to FIGS. 2 and 9-11 and Equations 1-17, and the steps of the method 1200 may be stored as instructions executable by one or more processors to perform operations for locating threat and point-of-source from effluent streams in accordance with embodiments of the present disclosure. At 1210, the method 1200 includes receiving information associated with the presence of one or more target molecules detected at each of one or more sampled locations and location information location information representative of one or more sampled locations. In an embodiment, the information associated with the presence of one or more target molecules detected at each of one or more sampled locations may be received by at least one processor from a molecule detector (e.g., the one or more molecule detectors 220 of FIG. 2, the one or more molecule detectors 960 of FIG. 9, the one or more molecule detectors 1060 of FIG. 10, or the one or more molecule detectors 1130 of FIG. 11), and the location information may be received from a positioning system (e.g., the positioning system 230 of FIG. 2, the positioning system 970 of FIG. 9, the positioning system 1070 of FIG. 10, or known position information as described with FIG. 11). In an embodiment, the one or more molecule detectors and positioning system may be housed within a standalone device, such as the dynamic reverse gas stack modelling device 200 of FIG. 2. In an additional or alternative embodiment, the one or more molecule detectors and positioning system may be provided as part of a system, such as the module system 900 of FIG. 9, the cloud-based system 1000 of FIG. 10, or the system 1100 of FIG. 11. As shown in FIG. 12, the method 1200 may also include, at 1212, receiving environmental information associated with the location information, and/or, at 1214, receiving infrastructure information associated with the location information. The environmental information may comprise wind speed data, wind direction data, temperature data, barometric pressure data, other types of environmental data, or a combination thereof, and may correspond to the environment where the one or more samples were obtained. The infrastructure information may identify infrastructure such as water, electricity, buildings, sewage, wind, oil and gas pipelines, other types of infrastructure, or a combination thereof proximate to or within a threshold distance of the environment where the one or more samples were obtained. At 1220, the method 1200 includes determining a dynamic reverse gas stack model based on the received information. In an embodiment, the dynamic reverse gas stack model may have a Gaussian dispersion for the one or more target molecules over the one or more sampled locations. In an embodiment, the dynamic reverse gas stack model may be determined by at least one processor (e.g., the one or more processors 210 of FIG. 2, the one or more processors 920 of FIG. 9, the one or more processors 1020 of FIG. 10, or one or more of the reverse gas stack modelling device 110 of FIG. 11). In an embodiment, the determination of the dynamic reverse gas stack model may be generated in accordance with Equations 1-17, as described above. As shown in FIG. 12, determining the dynamic reverse gas stack model may also include, at 1222, determining the dynamic reverse gas stack model based on environmental information received at 1212, and/or, at 1224, determining the dynamic reverse gas stack model based on infrastructure information received at 1214. At 1230, the method 1200 includes predicting a location of a source for one or more molecules of interest detected during sampling of the environment. In an embodiment, the predicted location of the source may overlaid on a geographic map, such as a map of the environment where the one or more samples were obtained. In an additional or alternative embodiment, the predicted location of the source may be further utilized to model a conventional gas stack model to be overlaid on a geographic map, such as to predict an extent of the distribution of the one or more target molecules into the surrounding area, which may include predicting distribution of the one or more target molecules into areas outside of the sampled environment (e.g., the environment may be sampled across small portion of the total area into which the one or more target molecules may be distributed). This may be useful for identifying additional areas from which to obtain samples, such as to predict and then verify the distribution of one or more target molecules.

Figure 13:
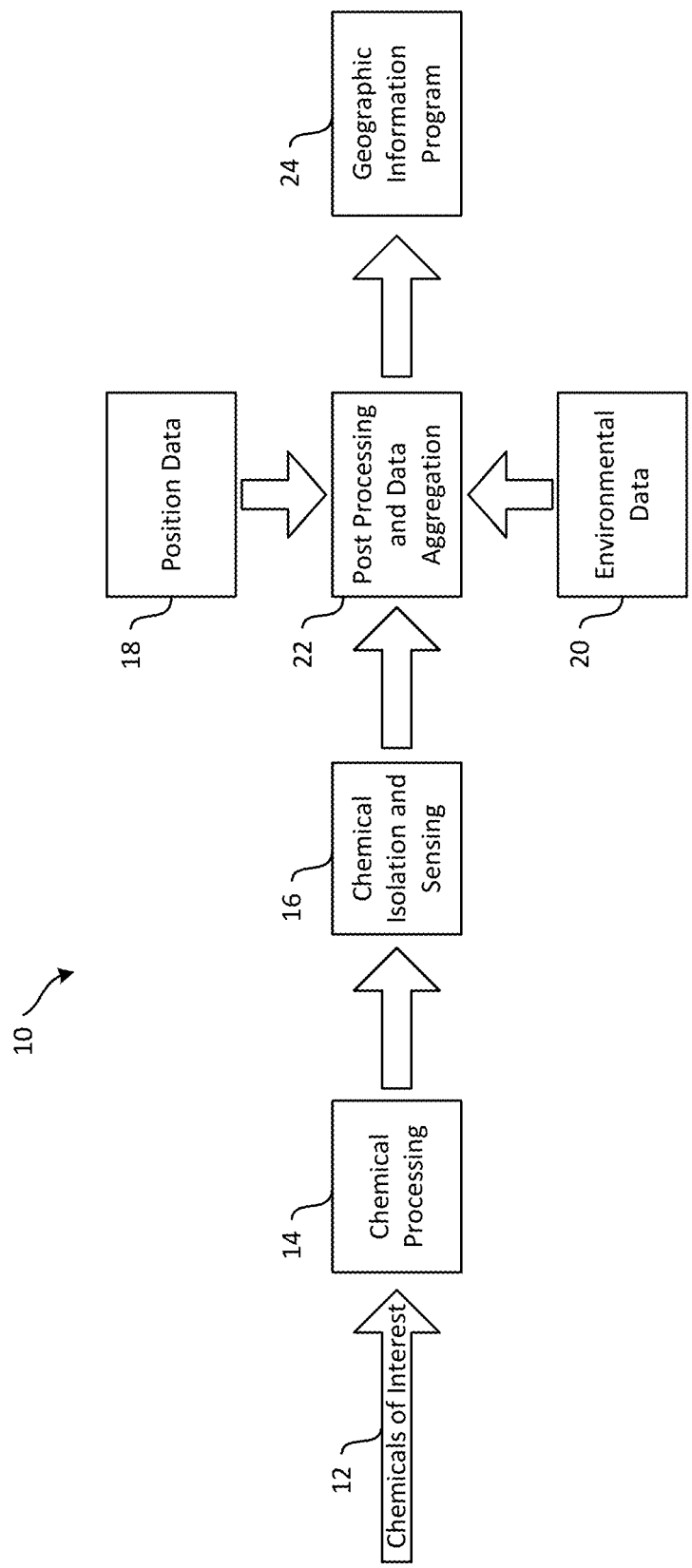
FIG. 13 is a flowchart that shows a detailed process flow of a particular embodiment of the present invention.

FIG. 13 is a flowchart that shows a process flow 10 of the present invention. Process flow 10 is an expanded view of the flow diagram shown in FIG. 12. A chemical of interest 12 is introduced into the system. Initially, chemical preprocessing 14 occurs whereby separatory methods are employed. In an embodiment, the separatory methods may isolate the analyte from the matrix, such as aqueous or atmospheric substituents. Such methods are, but not limited to, gas chromatography (GC), solid phase micro-extraction (SPME), or membrane permeation. Once matrix separation has occurred analytes proceed to isolation and sensing 16. Mechanisms of identification include, but are not limited to: electronic chemical sensors, optoelectronic sensors, chemiresistors, infrared spectroscopy (IR), ultraviolet-visible spectroscopy (UV-Vis), and mass spectrometry (MS). As identification occurs, positional data 18 is acquired by means of a positioning system. In an embodiment, the positioning system may include a global positioning system (GPS), a telecommunication-based localization positioning system (e.g., triangulation using cellular communication systems), or another type of positioning system (e.g., a positioning system that utilizes a coordinate system that is local to a location where the sensing occurs and which can be mapped to coordinates corresponding to a real-world location). Environmental data 20 may be acquired from onboard sensors and/or from surface atmospheric monitoring sites, including wind speed and direction, humidity, pressure, other environmental data, or a combination thereof. Post processing 22 may couple the chemical identification information, the positional information, and the environmental data, thereby attributing this information to a given point or location. This process may be repeated periodically (e.g., every "X" number of second, minutes, feet, yards, or some other unit of measure) or continuously over a given sampling area. Gas-stack models may be derived from which detection of a plume source location can be determined. In an embodiment, the sets of data may be formatted for input into one or more geographic information programs 24 for visualization.

Figure 14:
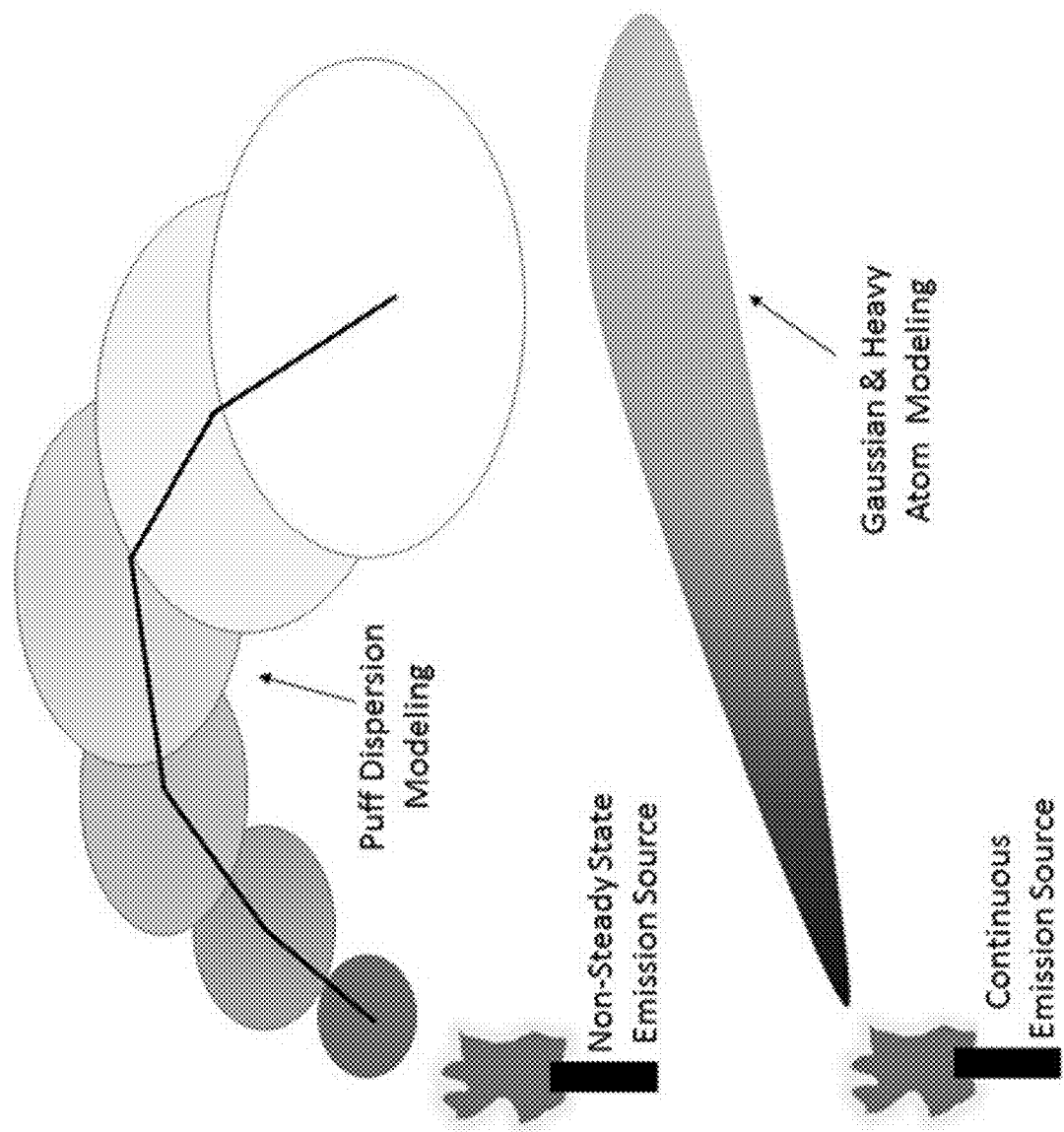
FIG. 14 is a diagram that compares two dispersion models for use with the present invention.

FIG. 14 is a diagram that compares two dispersion models for use with the present invention. Puff dispersion modeling uses non-steady state sources and a Lagrangian field to define the plume. These 'puffs' are parcels that are tracked through the model. Parcels are subjected to dispersion parameters that affect the trajectory, such as wind, terrain, and other environmental influences. Modeling is terminated when the perceived concentration of a given parcel is in union with ambient conditions.

Gaussian models assume the chemical of interest is disseminated as a normal probability distribution, or Gaussian dispersion. These distributions occur in two dimensions, a distribution downwind and dispersion broadening. Downwind dispersion yields the distance a given chemical of interest will travel away from a source, with the highest concentration being localized when a majority of surface deposition occurs due to gravity. Broadening occurs due to the non-linear characteristics of prevailing winds and general diffusion. Embodiments of the present invention may be more suitable to situations where the chemical of interest is disseminated as a Gaussian dispersion.

Figure 15:
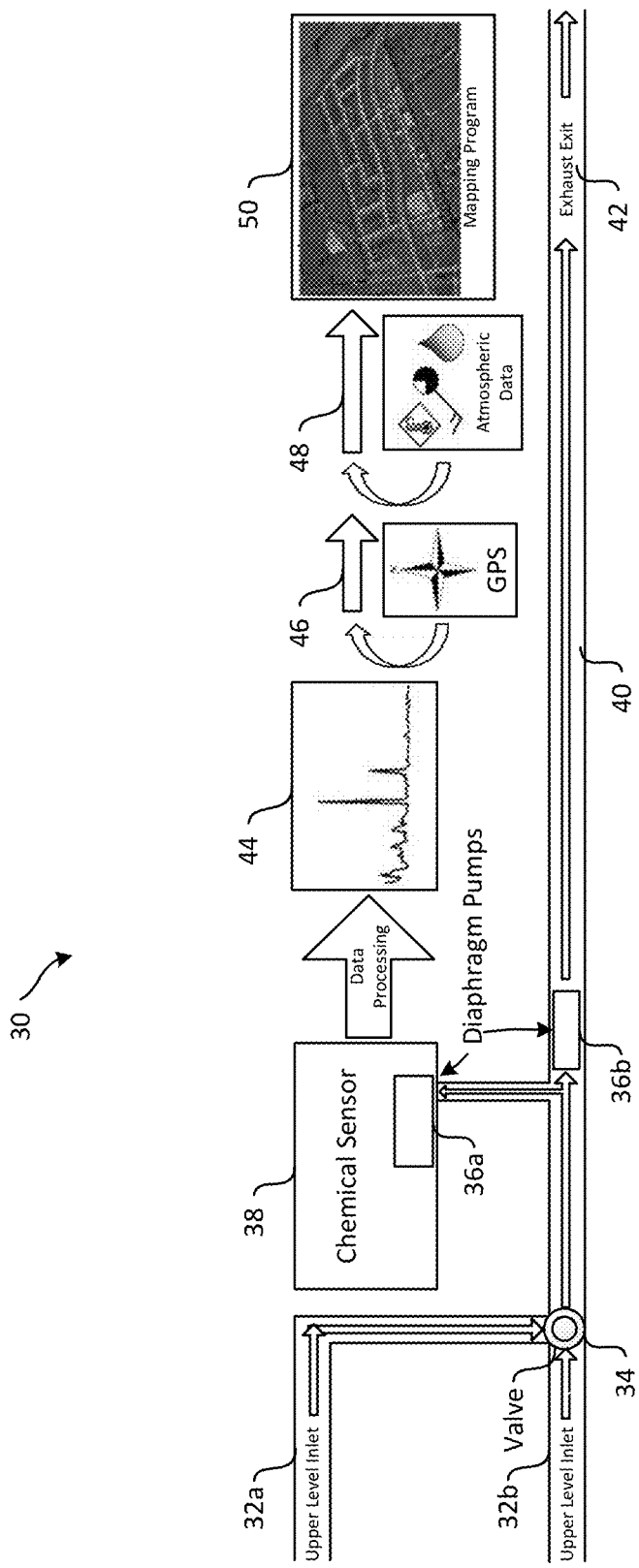
FIG. 15 is an example of a process flow of a particular embodiment of the present invention.
Figure 16:
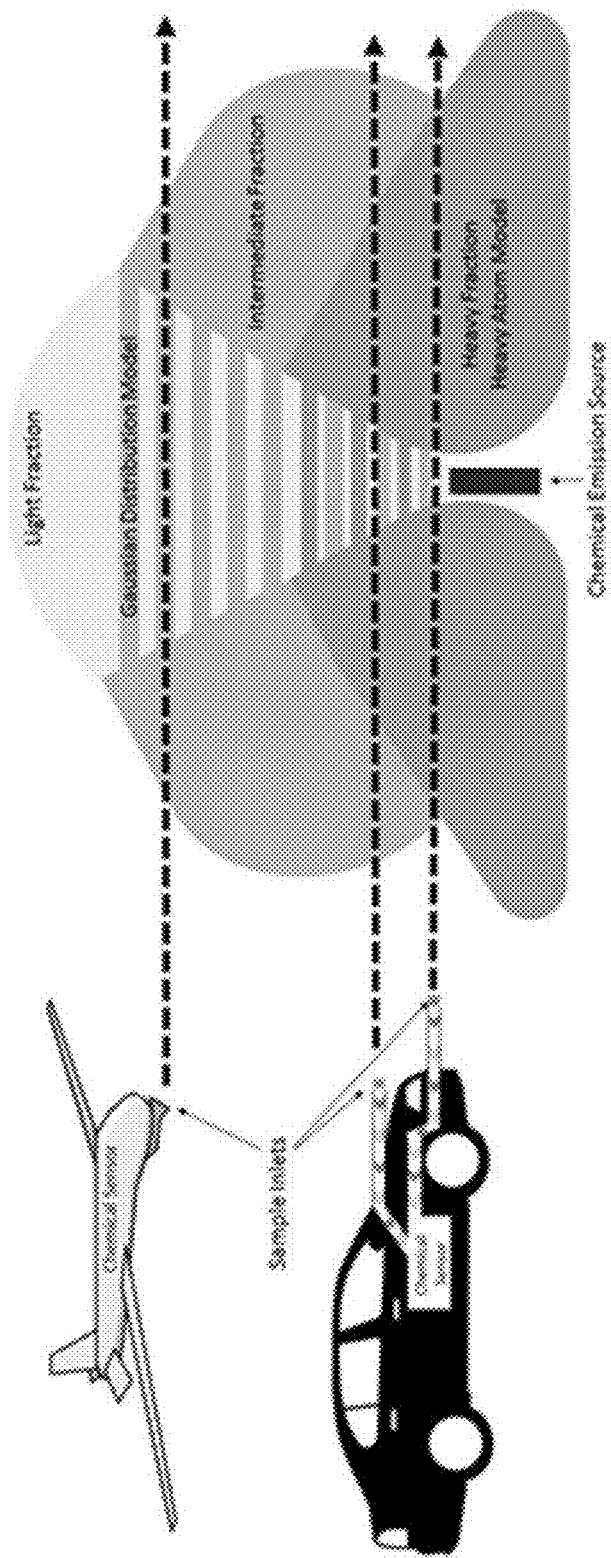
FIG. 16 shows the chemical emission for detecting the source of a chemical in three dimensions and the modeling of the same.
Figure 17:
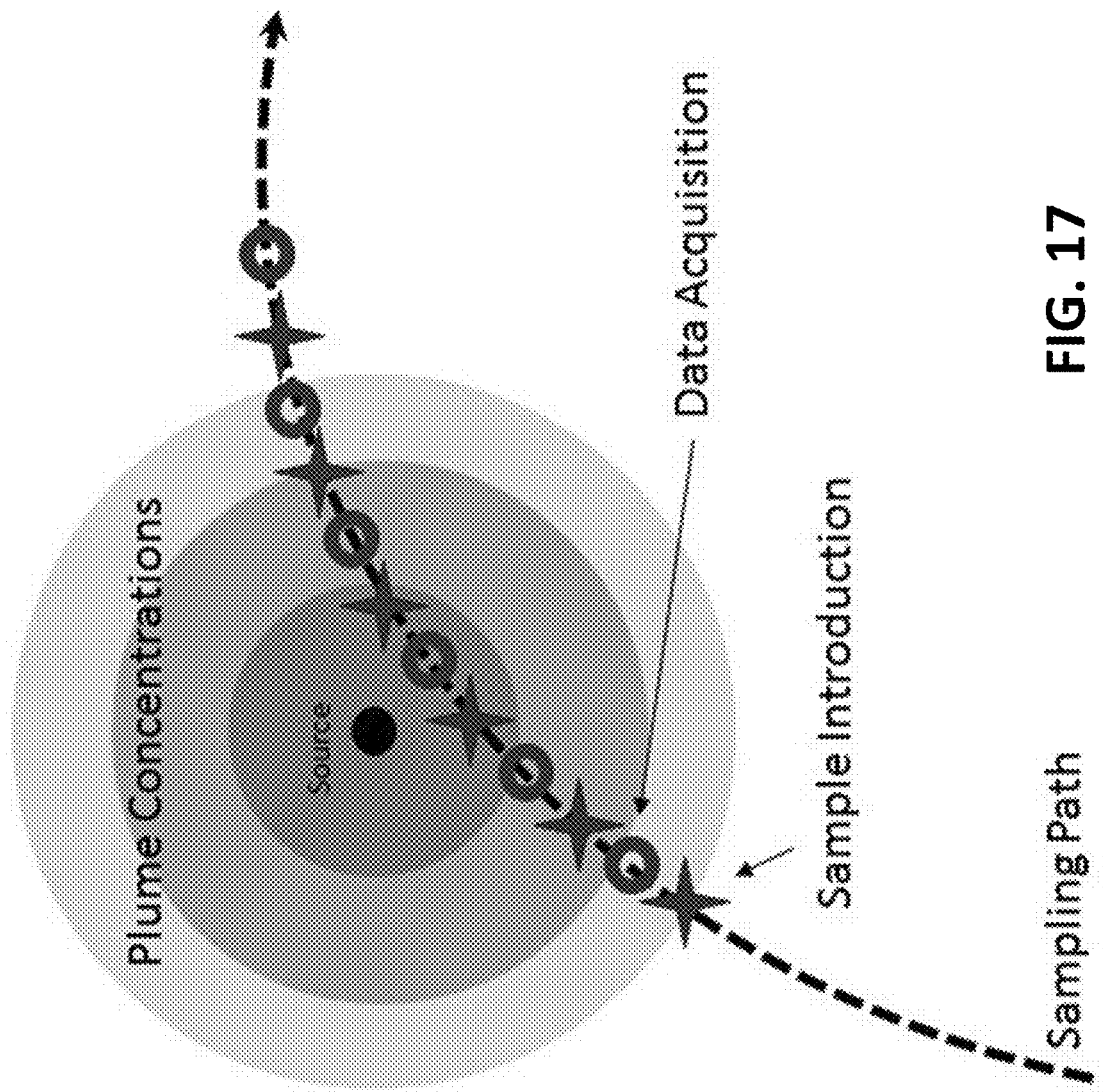
FIG. 17 shows the sampling path and expected detection of various regions of a chemical plume.
Figure 18:
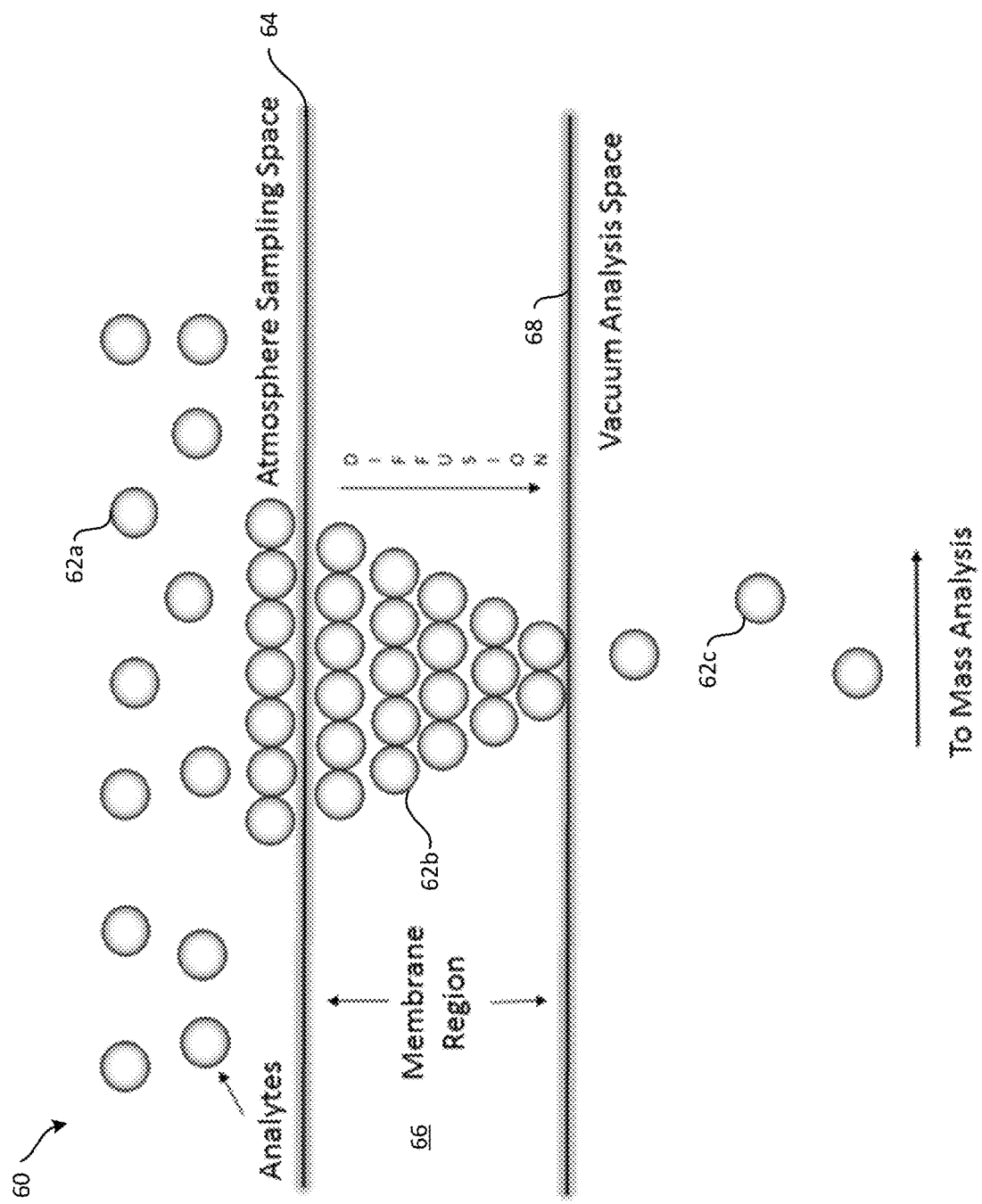
FIG. 18 shows an example of membrane inlet mass spectrometry (MIMS) for use with the present invention.
Figure 19:
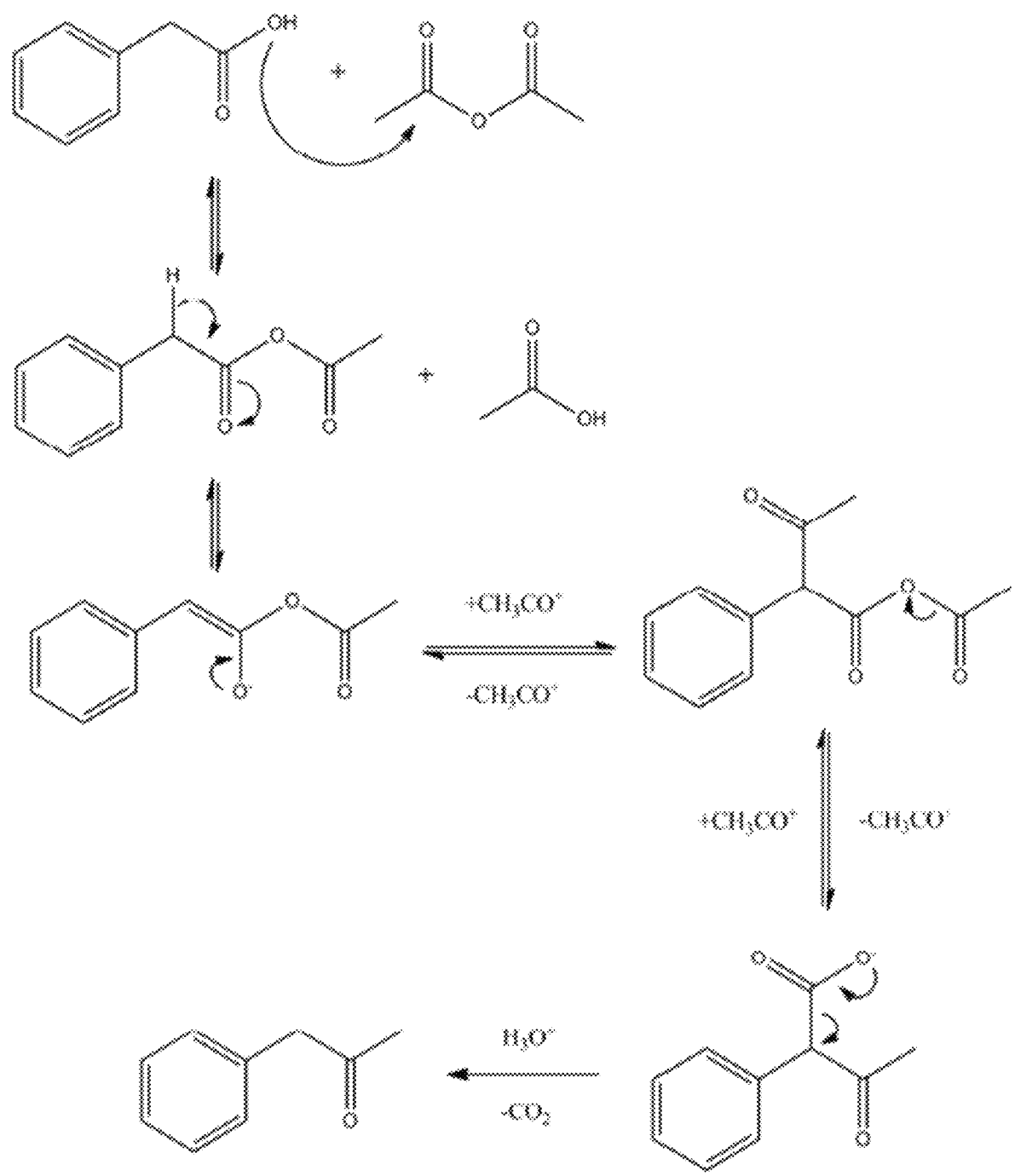
FIG. 19 reaction mechanism for the production of phenylpropanone (P2P)

FIG. 15 is another more detailed example of a process flow 30 for utilizing the present invention in an embodiment comprising a vehicular platform. Chemical of interests may be introduced into the vehicular platform via one of two inlets 32a, 32b. In an embodiment, the upper level inlet may be located a threshold distance above ground level (e.g., approximately four feet from a road surface), and the ground level inlet 32*b* may be located a second threshold distance above ground level (e.g., approximately eight inches from the road surface). In an embodiment, a valving mechanism 34 may be provided to direct which flow is active. In an embodiment, diaphragm pumps 36*a*, 36*b* in the main sampling tube may be provided to facilitate a constant sampling intake rate, regardless of the speed of the vehicular platform. In additional or alternative embodiments, a variable sampling intake may be utilized where the rate of flow is dependent upon the speed of the vehicular platform. The chemical sensor diaphragm pump 36*a* may sample a small fraction of intake air for chemical analysis 38. Excess intake air 40 may be directed towards the exhaust exit 42 of the vehicular platform. During analysis, collected spectrums 44 (e.g., spectrums of detected or identified molecules present in the intake air samples) are coupled with position data 46 and atmospheric data 48 to localize the detected spectrums to particular locations within a coordinate system. Position data utilized in the coupling may be provided by a positioning system (e.g., a GPS system, a telecommunication system, etc.). Atmospheric data may be obtained from onboard weather sensors or yielded from surface atmospheric measurement emplacements. This paired data is then formatted for mapping 50 in one or more geographic information programs. Points are attributed to a given value from the chemical sensor, via color, size, or shape. Relating groups of points allows for visualization of a given set of localized data points, useful for gas stack modeling. Files created for the mapping program can be disseminated to local devices, such as a display device (not shown in FIG. 3) or remote systems and devices (e.g., to a remote computing device via a network).

FIG. 16 shows an embodiment of a system for detecting the source of a chemical in three dimensions. A chemical emission source emits various pollutants continuously. As this occurs, a plume may form from the source position. Depending on the nature of the site, chemicals emitted may be classified into fractions based upon weight. Lighter fractions are generally considered lighter than ambient air. Intermediate and heavy fractions are generally considered heavier than air. Differentiating between intermediate and heavier fractions may be accomplished by modeling the dispersion, whereby fractions greatly affected by the gravity term, thus having limited downwind travel, are considered heavy. Furthermore, fractions that are heavier will disperse with less altitude than subsequently lighter fractions. The motorized vehicle uses two inlets to sample effluent. Ground level for heavy targets and a higher level inlet for lighter fractions. In an embodiment, an unmanned aerial vehicle (UAV) or manned airborne vehicle with a chemical sensor may be utilized so that even lighter fractions can be sampled and/or observed. The UAV will sample these fractions in manner similar to the flow described above with respect to the vehicular deployment shown in FIG. 15.

FIG. 17 shows the sampling path and expected detection of various regions of a chemical plume. Sampling occurs along a given path in which various regions of plume concentration are traversed. As a sample is introduced and subsequently identified via the chemical sensor, detection takes place with a diffusion delay. The exact point of contact with an analyte is back-calculated in real-time accounting for membrane diffusion time and the speed of the vehicular emplacement. This process may be repeated periodically or continuously until the sampling region has been navigated. This data may then be perceived as a Gaussian dispersion, first entering a region of low concentration proceeding to higher peak concentrations and lastly successively low concentrations are observed. The yielded Gaussian dispersion of concentrations from the chemical sensor combined with positional and environmental data may be used to mathematically back-calculate the source position, as described above with respect to Eqs. 1-17.

FIG. 18 shows an example of membrane inlet mass spectrometry (MIMS) 60 for use with the present invention. Membrane inlet mass spectrometry (MIMS) 60 introduces analytes into the mass spectrometer via a semipermeable membrane. Membranes are gas permeable, hydrophobic, and usually polymer based. The advantage of this method is a variety of analytes 62*a* can be introduced in real time, with minimal or no sample preparation. Analytes 62*b* traverse from the atmospheric sampling region 64 through the membrane 66 via diffusion. Diffusion-controlled permeation introduces the analyte 62*c* to the vacuum analysis space 68. Different configurations of membrane 66 introduction exist, including but not limited to, tubular flow-over, tubular flow-through, and planar sheets. Subsequent mass analysis may takes place in the vacuum region.

Example 1

Vehicle-Mounted Portable Mass Spectrometry System for the Covert Detection Via Spatial Analysis of Clandestine Methamphetamine Laboratories Global manufacture of amphetamine-type stimulants (ATS) has risen over the past decade, and the amount of global seizures of methamphetamine has risen 158% over the past five years, up to 88 tons in 2013. There was almost 3 tons of methamphetamine seized in the United States alone by the DEA in 2014. Further complicating law enforcement efforts, methamphetamine production is possible in a myriad of locations including suburbs, trailer parks, apartments, hotels, and in mobile laboratories. A search area cannot therefore be minimized based upon specific infrastructure. Currently, law enforcement requires a broad spectrum of methods to locate such covert activities, including trained canines, undercover agents, and extensive logistical support.

Presented herein are embodiments of a vehicle-based mobile mass spectrometer configured for the detection of precursors and synthetic byproducts characteristic of methamphetamine production by utilizing atmospheric spatial analysis techniques according to embodiments, which may help supplement current law enforcement techniques and efforts by providing a powerful, mobile system. The ability to detect atmospheric effluent created from clandestine methamphetamine manufacture may provide a useful tool for law enforcement. A membrane inlet mass spectrometer may be mounted onto a vehicle that samples atmosphere while in motion. In an embodiment, the vehicle may be an all-electric drive capable hybrid vehicle. Utilizing an all-electric drive vehicle may prevent contamination of the intake samples due to exhaust and other byproducts that may be present in vehicles comprising gas combustion engines. Attributing a latitude and longitude to each spectrum collected, unique chemical fingerprints from clandestine manufacture are then mapped. This location-based mass spectrum data provides a localization to an area of interest. The synthesis of methamphetamine precursors was performed and the impurities from such reactions were observed. A mock manufacture was setup and the impurities were introduced into the atmosphere via heating. The detection of products and impurities using this mobile platform has shown the effectiveness of locating and localizing the manufacture of methamphetamine, as described in more detail below.

Illicit drug seizures are often subject to forensic analysis confirming or denying the presence of illegal ATS. Beyond confirmation of the presence of a scheduled chemical, efforts to profile the impurities present in these samples results in chemical identifiers of synthetic routes. A myriad of routes (Leuckart, reductive amination, etc.) have been used to synthesize ATS, and each method has unique precursors and impurities that can help identify the route of manufacture. Common ephedrine-based methods have also been analyzed with three different routes studied. Further analytical methods have been applied to synthesis of precursor chemicals in ATS synthesis including 1-Phenyl-2-propanone (or P2P), from which forensics have been able to determine the routes of synthesis from apprehended samples. Biological systems, most commonly baker's yeast, have been used to yield 1-phenylacetylcarbinol, a precursor to methamphetamine. The genesis of using yeast resulted from the restricted availability of ephedrine and pseudoephedrine, indicating a heightened awareness of clandestine chemists to advances in the literature. Chemometric procedures have been developed that consider ratios of impurity concentration and isotopic distributions. Methods of manufacture and precursor synthesis have been well studied and ultimately result in abilities to trace endpoint product to these individual routes and reagents.

Environmentally, these manufacturing methods often emit trace chemicals that are detectable on surfaces and in the atmosphere, but are often unregulated. Various scenarios have been constructed to mimic environments where instrumentation can be used for on-site testing. Importation of cocaine in cargo containers through the port of Miami have provided a test situation for high volume vapor sampling, with analytical methods such as ion mobility spectrometry (IMS) and gas chromatography mass spectrometry (GC/MS) providing drug identification. IMS of illegal drugs using varying temperature and concentration parameters has also been conducted in customs situations. This resulted in determination of suitable analysis conditions for amphetamine and lysergic acid diethylamide (LSD) at nanogram concentrations. Other studies have analyzed surface chemistry of contraband via IMS.

Development of additional techniques include fieldable sensors and instrumentation. The U.S. Drug Enforcement Agency (DEA) has collated efforts for detection of drugs of forensic interest. Even solvents, such as pyridine from the Leuckart synthetic method, have been focused on as a detectable material and subsequent rapid methods have been developed with IMS and photoionization for their detection. Field-deployable systems have been used in clandestine lab sites, and have been utilized in forensic processing of the scene. Biosensors and immunosensors have been developed to detect the presence of illegal drugs and even explosive chemicals. Further overviews specifically towards IMS29-32 and other detection technologies have been well documented.

Ultimately, clandestine manufacture provides two means of direct evidence, being that there are lasting environmental signatures within the area of synthesis and continual effluent during the various stages of production. Efforts to quantify environmental impacts have resulted in the creation of health and safety policies to use in clandestine lab reclamation. These strategies apply specifically to remediation of contaminated infrastructure. Analysis in soil samples show effects of manufacture exist outside the clandestine laboratory itself, often a result of improper disposal of chemicals. Ongoing methods are being developed for real time sampling and monitoring of chemical reactions involved in the manufacture process of illegal drugs, including utilization of solid phase microextraction (SPME) in capturing drug vapors. SPME fibers proved effective in observations of decomposition and reaction products. Syntheses of methamphetamine via two clandestine methods were monitored with ambient ionization methods in real time with portable mass spectrometry. Their results found that covert synthesis was identifiable throughout the reactions by the effluent produced.

Since clandestine manufacture of ATS is typically accompanied by unavoidable byproducts, reactions often exude many chemical signatures. The following work catalogs the development of methods for detection of clandestine labs using an all-electric capable hybrid vehicle mounted mass spectrometer. The system uses a custom atmospheric intake that continually samples and passes samples through a membrane inlet. Membrane inlet mass spectrometry (MIMS) uses a semi-permeable membrane to allow analytes to pass through for analysis while maintaining vacuum of the system, as described above with reference to FIG. 18. Obtained mass spectra are then GPS tagged to locations. A mock covert methamphetamine synthesis was performed, producing effluent that was subsequently detected for the presence of precursors and byproducts. The vehicle then mapped the area and data was plotted so that spatial analysis could be performed. Ultimately, the system detected the atmospheric constituents that constitute ongoing methamphetamine manufacture.

To analyze the precursors and impurities commonly found in the synthesis of an ATS, phenylacetic acid (>99%, Sigma-Aldrich, St. Louis, Mo.) was converted to 1-phenylpropan-2-one (P2P) by use of acetic anhydride (AR, Mallinckrodt, Paris, Ky.) and pyridine (99+%, ACROS Organics, New Jersey, USA) via the Dakin-West reaction. The Dakin-West reaction was originally developed to convert α-amino acids into their respective α-acetylamino-alkyl methyl ketones, but works for certain non-amino acids. This reaction mechanism, shown in FIG. 19, involves the interconversion of phenylacetic acid to its anhydride in the presence of acetic anhydride. This phenylacetic anhydride loses a proton in the presence of pyridine. It is then acylated by another acetic anhydride and subsequently deacylated to produce a β-keto acid, and finally decarboxylated to produce the final ketone product.

After the reaction was complete, the reaction mixture was then subjected to analysis within the reaction vessel without further alterations or additions. To prevent information on clandestine synthesis becoming publically available, only general details on the synthetic procedure will be given herein. All endpoint products were then classified with GC/MS (Focus GC/Polaris Q) to confirm the presence of the target precursor and expected byproducts.

Phenylacetic acid was combined with pyridine and acetic anhydride and refluxed under anhydrous conditions for a period of time. Pyridine, P2P, and acetic anhydride are all flammable liquids and as such must be kept away from any sources of ignition during the reaction process and stored in an appropriate flammable liquids cabinet. Acetic anhydride can also react violently with water, so storage and handling must preclude its exposure to sources of water.

To simulate the environment where methamphetamine synthesis has taken, or is taking, place, a mobile home trailer park, referred to as Crime Scene City, used for forensic science students was chosen as the site. At the site, multiple unoccupied mobile homes are in close proximity to one another, simulating a common environment where a "cook" could take place. The location is easily accessible, and readings can be taken with the mobile instrumentation in all directions directly adjacent to the site. Within the mobile home, the reaction mixture was placed in a bathroom on a hot plate with a stir bar and heated to temperatures consistent with a methamphetamine reaction. Windows and vents in the bathroom were opened to allow effluent to escape. Personal protective equipment (PPE) was equipped at all times within the mobile home and directly adjacent to the site to prevent the inhalation of any effluent vapors or accidental exposure via skin contact.

Figure 20:
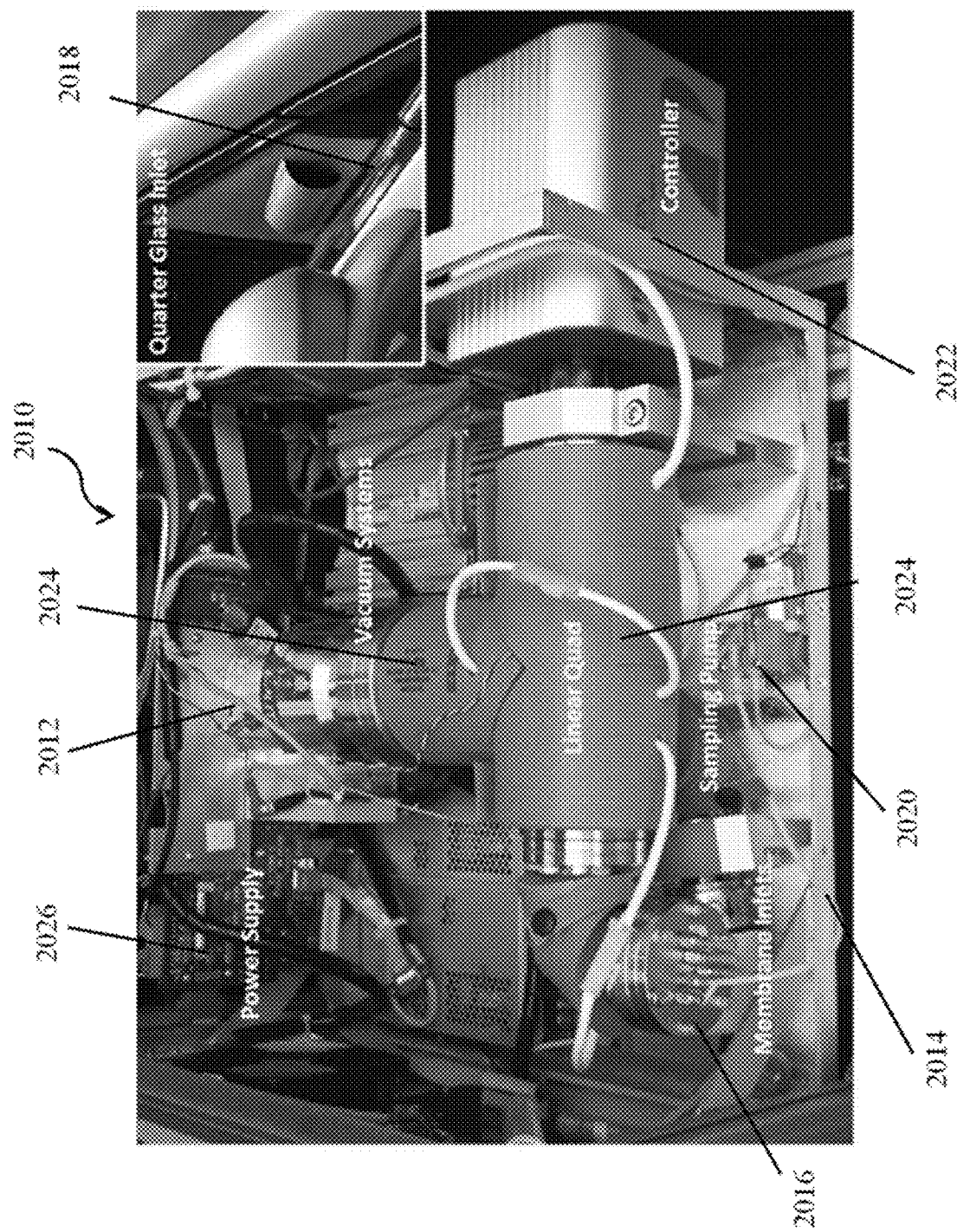
FIG. 20 shows one example of a mobile system using a mass spectrometer installation mounted where the front passenger seat existed—Inset: designed and installed air intake inlet for use while in operation and the unit is placed in a rack mountable case.

Referring briefly to FIG. 20, an exemplary chemical detection unit 2010 according to the embodiments of the present invention is shown. A mass spectrometer 2012 is a Transpector MPH (Inficon, Syracuse, N.Y.) Residual Gas Analyzer (RGA). The unit 2010 is contained in a ruggedized rack-mountable case 2014. A membrane inlet 2016 front end was designed on a 2.75" Conflat blank flange, with feed-throughs that provide mountings for the tubular membrane (Helixmark, Carpinteria, Calif.). The unit 2010 was mounted where the front seat existed in a Ford Fusion Energi™. The Fusion offered hybrid drive, what provides the ability to override traditional gasoline engine function, which removed any combustion interferences while mapping an area. Atmosphere is introduced into the system through an in-house made quarter glass replacement 2018, providing an inlet in which a diaphragm pump continuously pumps through atmosphere. From the atmospheric sampling tube a smaller diaphragm sampling pump 2020 samples a small quantity of air to pass through the tubular membrane. Also shown is a power supply 2026 and a controller 2022 connected to a linear quad 2024, which is connected to vacuum systems.

The system repeatedly scans masses and tags each scan with an associated latitude and longitude, using a combination of a Python script and Arduino-based microcontroller with GPS capability. Post processing of data was performed using Google Earth to plot obtained intensities for a given mass. In an embodiment, colored circles may be used to attribute a location and intensity to a particular sample to present the sample data in a user-friendly format. These masses may be associated with given byproducts of synthesis and further compared to baseline data obtained before the experiment began. Noticeable increases in intensity are attributed to the displacement of precursors and synthetic byproducts into the atmosphere from the experiment. Finally, the National Oceanic and Atmospheric Agency (NOAA) and Environmental Protection Agency's (EPA) Areal Locations of Hazardous Atmospheres (ALOHA) software is used in conjunction with local weather data to provide a theoretical means of effluent plume diffusion and to validate emission source predictions generated by the dynamic reverse gas stack model.

Figure 21A:
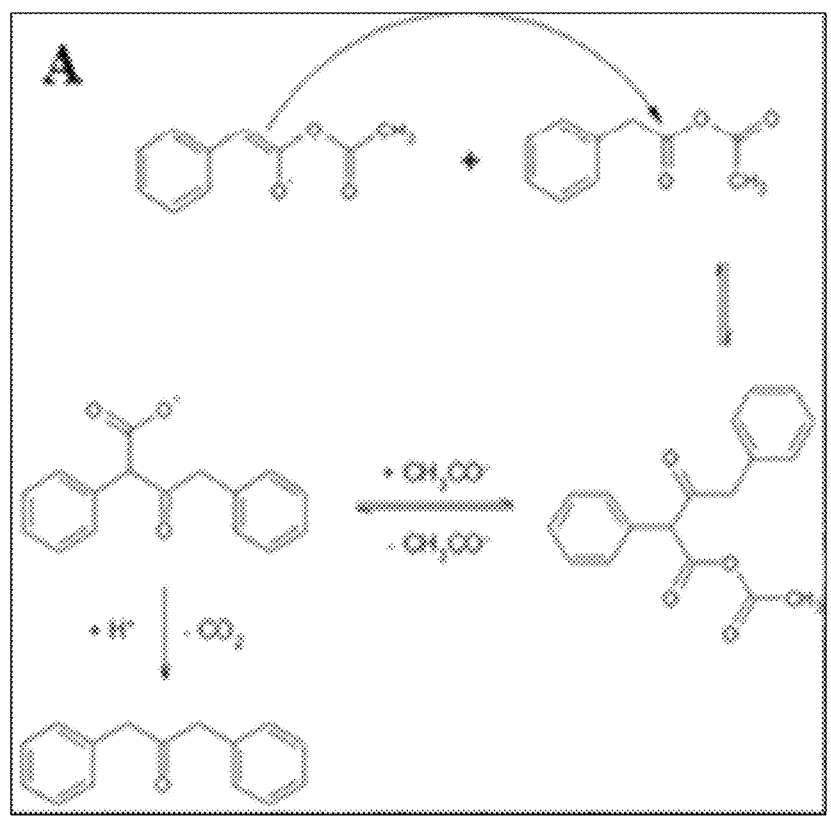
FIG. 21A shows the reaction mechanism for the production of dibenzylketone (DBK)
Figure 21B:
FIG. 21B shows the baseline mass spectrometric data for BDK.
Figure 21C:
FIG. 21C shows the data obtained data resulting from displacement of BDK during mock manufacture.

During the production of ATS precursors, side reactions are unavoidable and often show indications of the synthetic routes of manufacture used. Many of these reaction mechanisms are known in the literature, although the exact route may still be debated. For the Dakin-West reaction the most commonly seen impurity, 1,3-diphenylpropan-2-one or dibenzylketone (DBK), results from a lack of excess of acetic anhydride present in the reaction. This causes the mixed anhydride to be acylated by another mixed anhydride molecule rather than acetic anhydride and produce the dark-colored ketone impurity, as shown in FIG. 21A. The DBK impurity was tracked using the 118 m/z fragment. FIG. 21B shows baseline data illustrating no detectability of DBK within the atmosphere hours before the simulation took place; this holds true for all masses obtained. There were no detectable atmospheric constituents that could be mistaken as a false positive for a given mass associated with a precursor or byproduct. FIG. 21C indicates elevated levels as compared to baseline.

Figure 22:
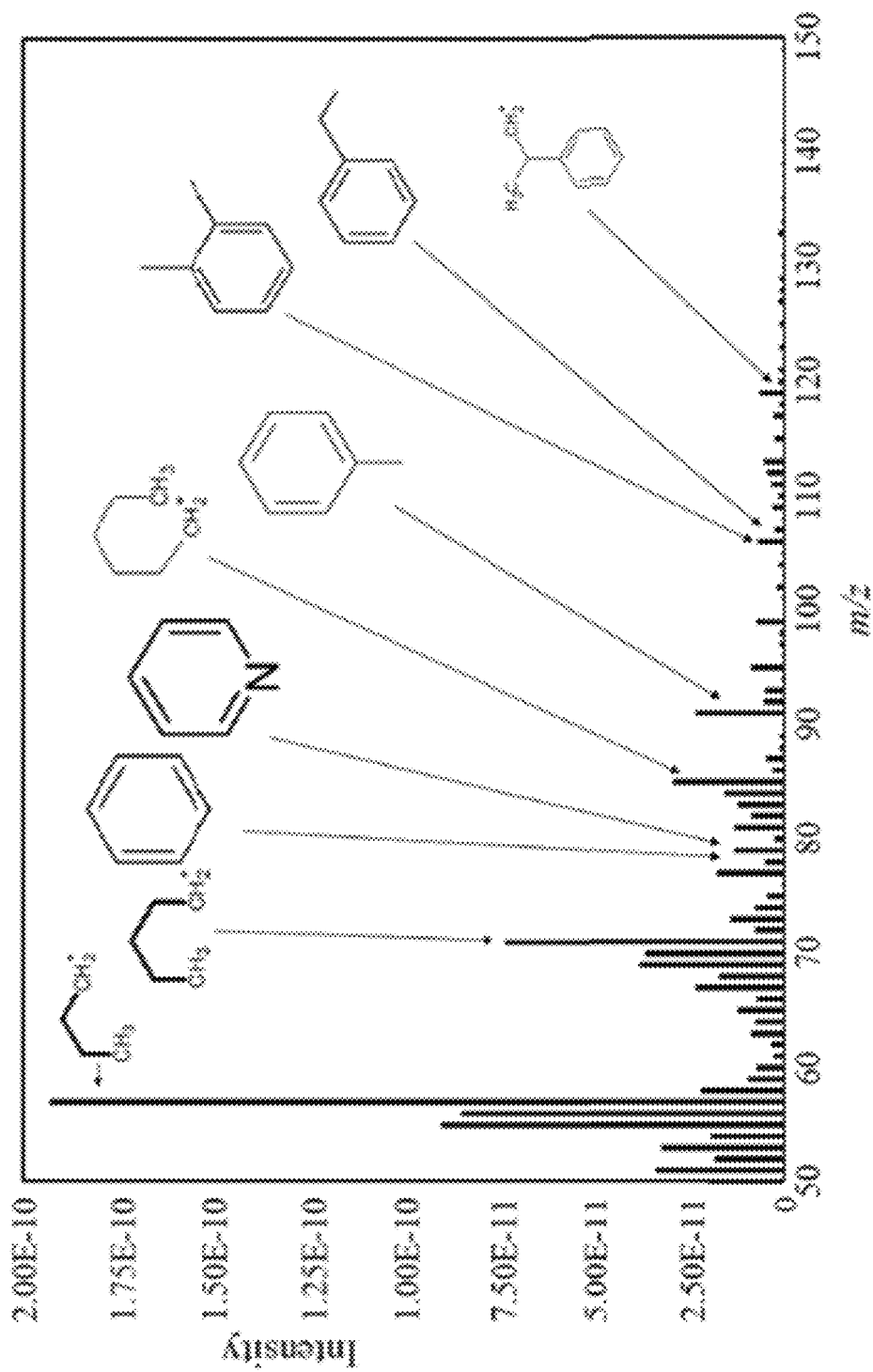
FIG. 22 is a graph that shows a representative scan obtained during operation of a vehicle.
Figure 23A:
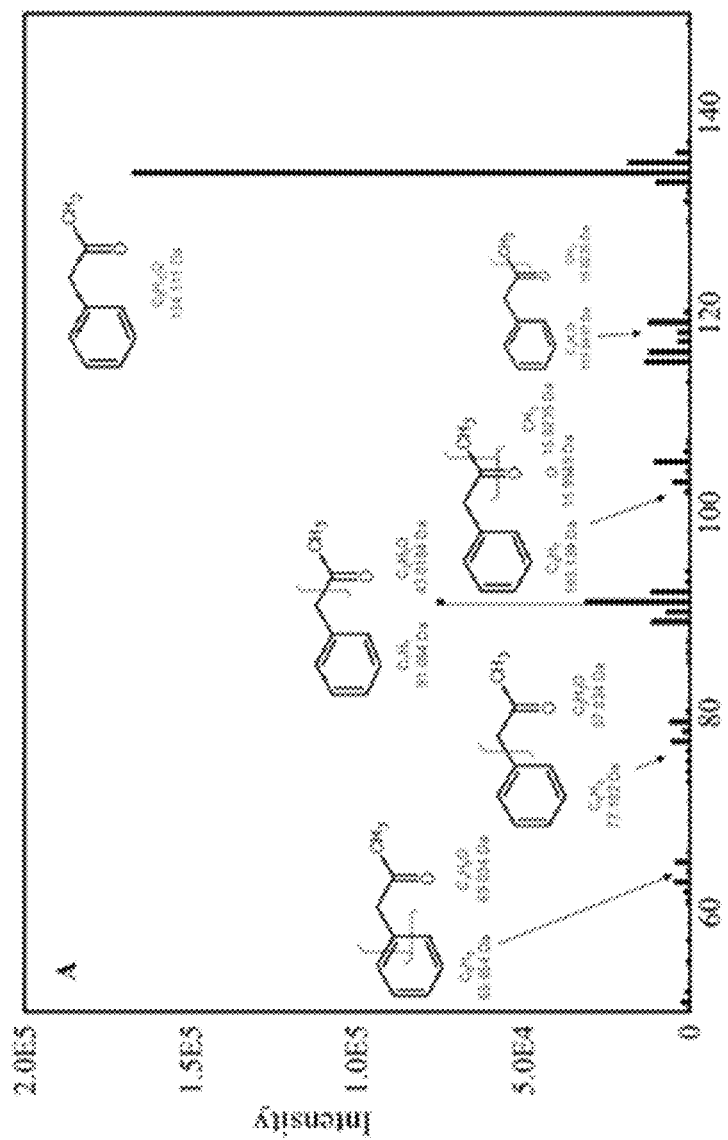
FIG. 23A shows a mass spectra of product P2P.
Figure 23B:
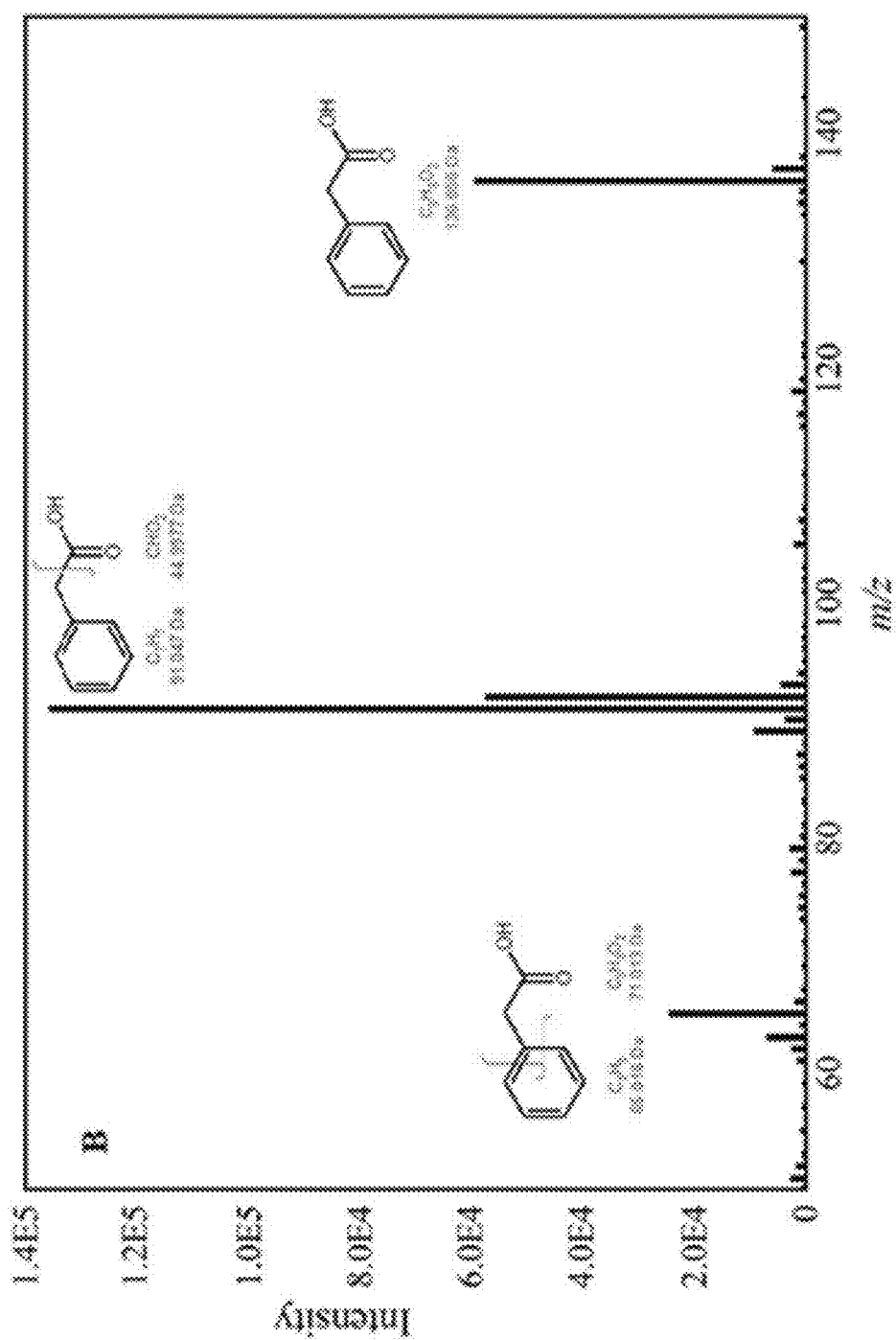
FIG. 23B shows a mass spectra of the precursor phenylacetic acid.

Many portable systems have been developed utilizing membrane inlet techniques. These systems use the same principle of allowing selective permeation of an analyte through a membrane for mass analysis. Many different materials have been studied as potential materials for membrane use; polydimethylsiloxane (PDMS) is one that has shown excellent results for aromatic compounds. The mass spectrometer and membrane inlet in the vehicular system illustrated in FIG. 20 has been used elsewhere for analysis of benzene, toluene, ethylbenzene, and xylene (commonly known as BTEX) and polycyclic aromatic hydrocarbons (PAHs). During the simulation, scans were repeatedly collected and FIG. 22 is a bar graph representative of the detected spectra. Peaks are the result of solvent or fragmentation of parent mass constituents in the manufacturing process, and those impurities have been profiled. The presence of alkanes is the result of fragmentation post-introduction as the choice of membrane is selective for chemistries that contain aromatics. FIGS. 23A and 23B illustrate mass spectra of obtained P2P and unreacted excess precursor phenylacetic acid. These resultant products, in addition to other impurities elucidated below, were used in the trial.

Figure 24A:
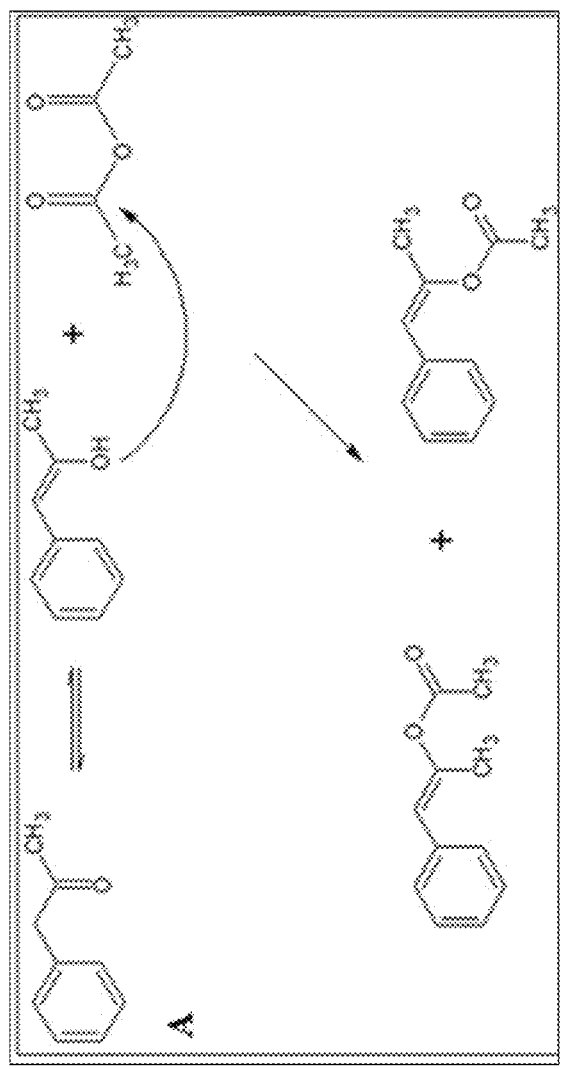
FIG. 24A shows the reaction mechanism for the production of E and Z-enol acetates of P2P.
Figure 24B:
FIG. 24B shows a plot of detection in of the P2P acetates.

Another common impurity results from the base-catalyzed enol tautomer of P2P formation. The enol tautomer becomes more kinetically favorable with the addition of base and condenses with acetic anhydride to form E- and Z-enol acetates of P2P, seen in FIGS. 24A and 24B. FIG. 24B is a plot that shows more varied concentrations. The periodic high and low intensities could be accounted for due to wind. Furthermore, the operator of the vehicle periodically overlapped each area and as chemicals were dispersed, readings of low concentrations could be attributed to an area where a once higher concentration existed, and vice versa.

Figure 25A:
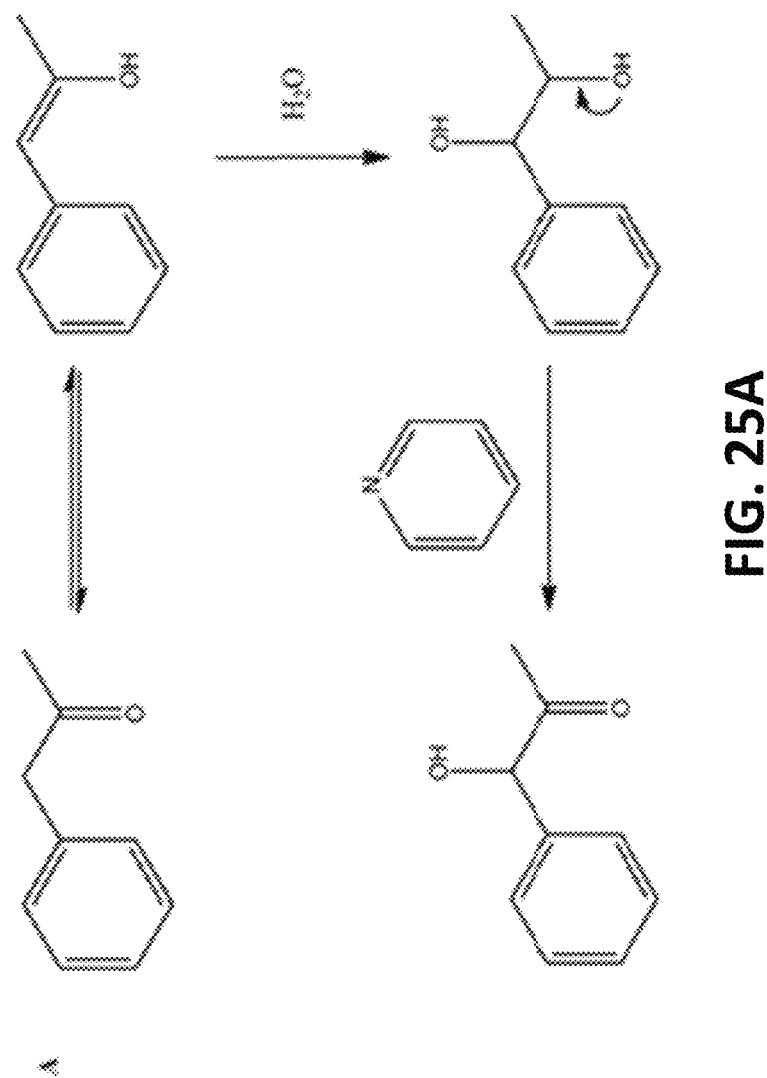
FIG. 25A shows the reaction mechanism of phenylacetylcarbinol synthesis.
Figure 25B:
FIG. 25B shows the detection of the chemical signature.

Phenylacetylcarbinol is produced by a similar reaction proposed here, but the enol tautomer instead undergoes hydration in an anti-Markovnikov fashion across the double bond, as shown in FIGS. 25A and 25B. This addition can be explained by the enhanced resonance available to the benzylic anion intermediate and presence of pyridine as a weak base.

Figure 26:
FIG. 26 shows the data obtained for benzyl acetate byproducts.
Figure 27:
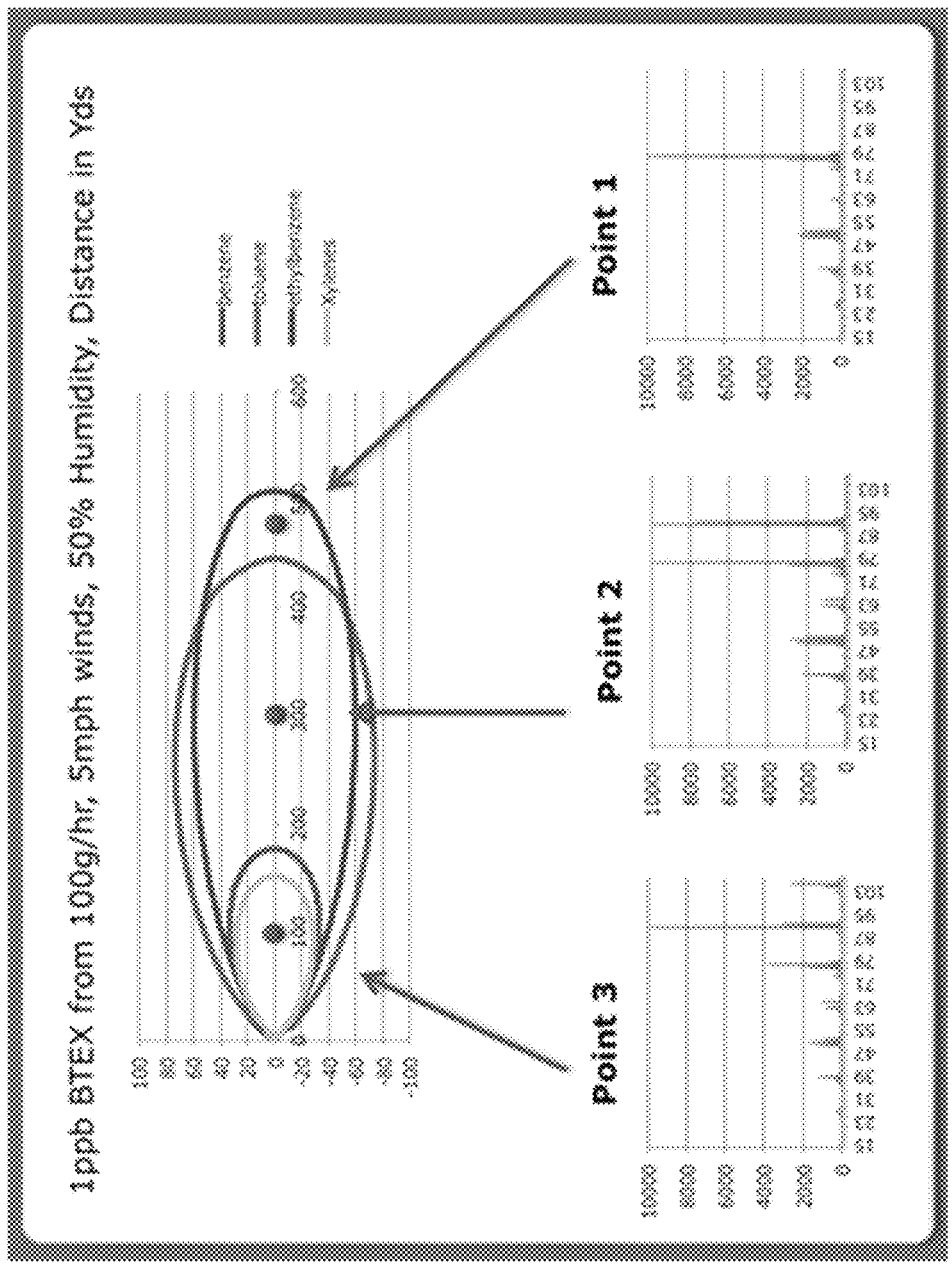
FIG. 27 shows the plume data and graphs for analytes at different locations.
Figure 28:
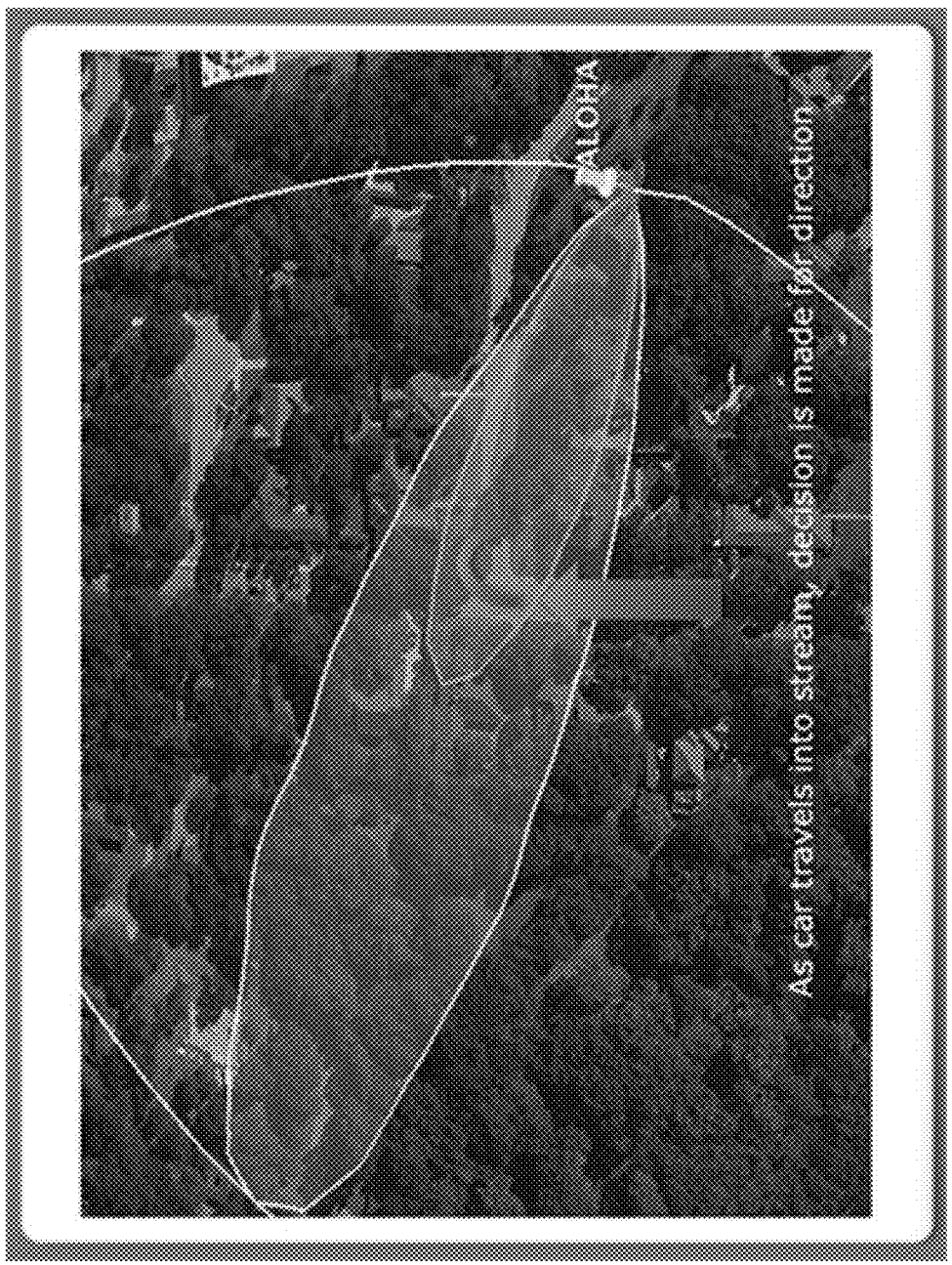
FIG. 28 shows a plume map overlaid on a real-time map that shows an example of the direction of travel for a vehicle and the detection of analytes.
Figure 29:
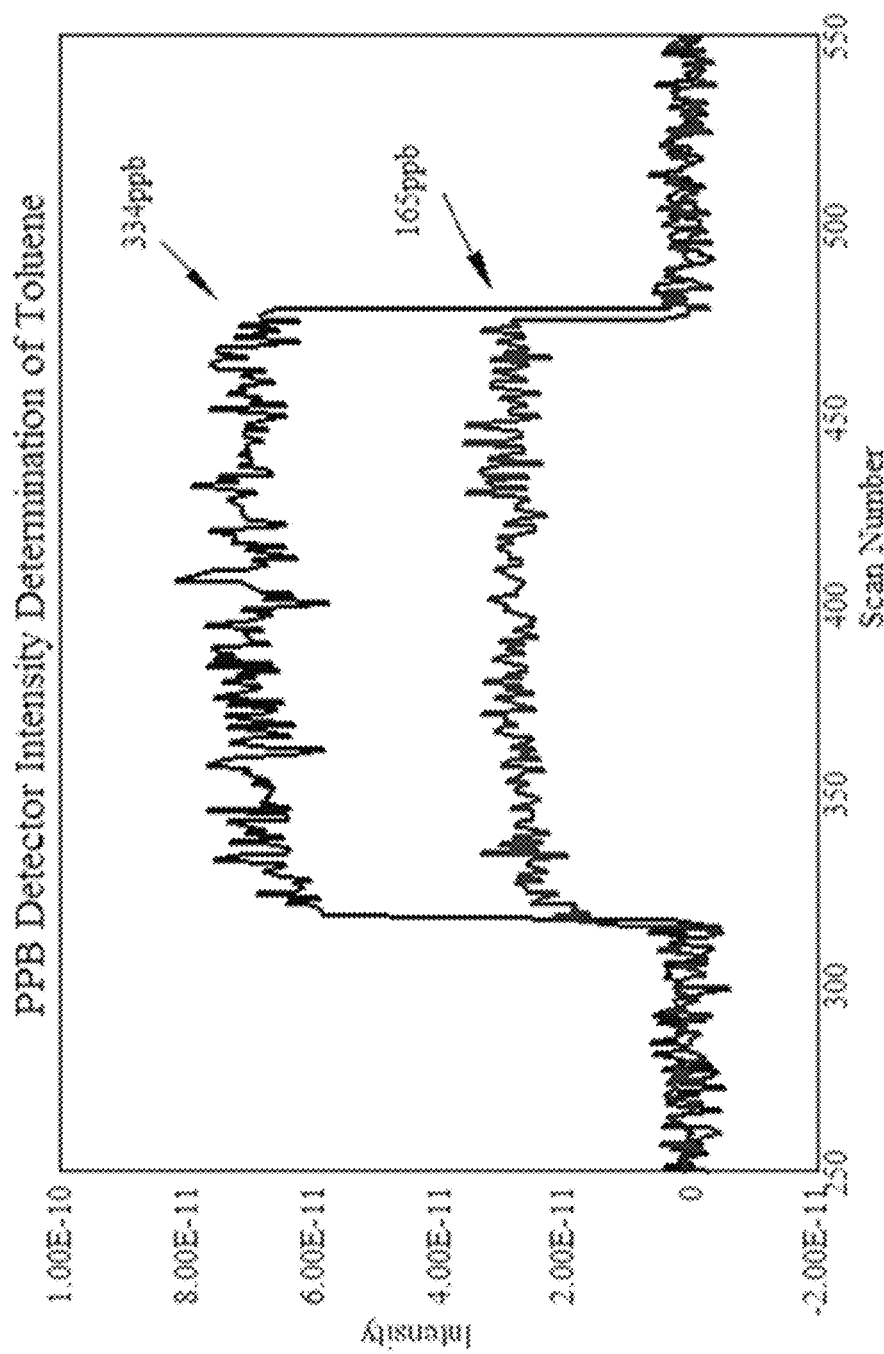
FIG. 29 shows a representative example data obtained from FlexStream concentration determination where effluent concentrations were scanned multiple times and an average detection intensity obtained.

In testing, incorporating the ALOHA software suite with the Google Earth plots overlays a theoretical calculation of diffusion streams for a target chemical. FIG. 26 is a plot of 108 m/z fragment of benzyl acetate. Benzyl acetate has been shown to be a constituent impurity of ATS synthesis. FIG. 27 shows the plume data and graphs for analytes at different locations. FIG. 28 shows a plume map overlaid on a realtime map that shows an example of the direction of travel for a vehicle and the detection of analytes. ALOHA uses chemical properties such as boiling point and molecular weight of the substance to approximate the distance of travel in weather conditions. Additional inputs account for the toxicity of the chemical. Allowing for regions to be defined with exposure limits. The plume is calculated from the source location and illustrates how windage would cause the drift downwind. The large structure south of the source location allowed for chemical elements to be pushed eastward along the wall of the structure. The combination of experimental data and theoretical plume predictions provide many opportunities for further validation trials. Given the location of an active ATS synthesis, the software can be used to predict where detectable constituents are. Mass data predicted by ALOHA dispersion models was applied post experiment, and matches well with experimental mass data collected via sampling. This validates that collected chemical data can provide reliable inputs for calculating a dynamic reverse gas stack model as described above with respect to Equations 1-17.

The detection of chemical markers from ATS synthesis allows for the detection of other illegal drugs manufactured in the same manner. The present invention can also be applied to detect those synthetic routes. Statistical analysis of data provides further localization. The highly mobile platform makes rapid deployment possible. The real time monitoring can actively alert an operator toward a given location, zeroing in on a target manufacture. The system is discrete enough to use in public, may enable law enforcement to obtain non-infringing samples that could aid in obtaining search warrants, for example.

Example 2

A Mounted Portable System in a Hybrid Vehicle for Spatial Quantitation and Mapping of Pollutants The use of a vehicle-based mass spectrometer or chemical sensing device for spatial mapping and quantitation can be useful to a community in identifying local atmospheric chemicals. Vehicular mapping of areas adjacent to known industrial activities that potentially emit harmful contaminants will provide real time data. As a regulatory tool, this emplacement can qualify a site of activity to be in compliance with environmental protocols. Furthermore, the emplacement has been effective in mapping urban environments. The use of an all-electric drive capable vehicle mounted with a mass spectrometer will remove any contamination of the analysis from internal combustion. This may allow for mapping in confined regions without concern for exhaust gases. The Membrane Inlet Mass Spectrometry (MIMS) method uses semi-permeable materials that allow for the selective transmission of analytes into the device. Sampling, GPS localization, and other atmospheric data may be accomplished through a variety of techniques, including use of open-source microcontrollers. Highlights and preliminary data obtained during a study are described below and exhibit the capabilities of this type of deployable MIMS system.

Mass spectrometry is an analytical technique that detects the mass to charge ratios of gas phase ions of interest. Although these systems have been routinely limited to research lab based analysis, there has been considerable development of miniaturized and portable mass spectrometer systems. The Membrane Inlet Mass Spectrometry (MIMS) technique lends itself to portability. Consequently, MIMS is becoming a common method of sample introduction that is subject to considerable development. MIMS allows for minimal sample preparation, continuous sampling, and exclusion of complicated analyte introduction techniques. Sampling may be accomplished using a semi-permeable membrane that allows selective analyte passage into the vacuum of the mass spectrometer. MIMS and other portable systems are becoming the preeminent choice of environmental analysis with increasing opportunities for the future development of specialized systems. Expectantly, these systems will become a mainstream tool to provide real time results with regard to pollutants in a site's atmosphere.

Portable instrumentation originated with miniaturization and ruggedizing of laboratory style instruments. Early techniques for in situ analysis included the use of miniaturized magnetic sector mass analyzers and gas chromatography-mass spectrometry instrumentation. Innovative efforts utilized atmospheric pressure ionization methods, such as Direct Analysis in Real Time (DART) and Desorption Electrospray Ionization (DESI) techniques. Measurements taken with deployable systems have been developed to monitor effluent matter from industrial processes, chemical concentrations resulting from vehicle exhaust, and chemical warfare agents. Recent attempts to increase portability and miniaturization have resulted in backpack and handheld systems.

The emphasis in developing a portable mass spectrometer system now incorporates the ability to test these systems in non-conventional situations where the data is not only quantitative but additionally has spatially relevant associations. Spatial mapping has previously been accomplished across Northern Spain allowing for visualization of temporal changes in concentrations of volatile organic complexes (VOCs) with deployable systems. Mapping of water quality and the detection of chemical plumes in marine environments have been accomplished by dedicated systems. Mass spectrometers are now being used on unmanned aerial platforms with spectrum data determined along a given flight path for volcanic analysis. These innovative methods provide excellent spatially resolved data for their respective sites.

Vehicular installations are certainly the most common platform for spatial analysis. One of the first moveable mass spectrometers was a van for rapid environmental analysis. Additional efforts to provide specialized drivable laboratories have resulted in monitoring units for coal tar clean up. Other transportable laboratories provide local analysis of trace gases providing emission source characteristics. All the advancements mentioned culminate in ruggedized and highly portable mass spectrometer based systems that are no longer intended for stationary vehicular platforms. Application of these systems centers on analyzing volatile organic compounds (VOCs), with an emphasis on benzene, toluene, ethylbenzene, and xylenes (commonly referred to as BTEX), polycyclic aromatic hydrocarbons (PAHs), and alkyl benzenes. These chemicals are known to be toxic and carcinogens. Recent efforts have provided street level data in mobile systems mapping various VOCs and other chemicals of interest. However, these systems are mounted in vehicles in which the method of locomotion is internal combustion and research has indicated that the origins of many VOCs are from petroleum ignition.

In contrast to these systems, which are subject to error (e.g., due to the use of conventional combustion engines), embodiments of the present disclosure may utilize vehicular-based system that incorporates the MIMS technique for detection of PAHs and BTEX installed in an all-electric drive capable vehicle, thereby eliminating or substantially reducing the error/interference caused by byproducts produced by combustion engine systems. Therefore, any possibility of exhaust interference from the mobile unit could be eliminated. The Ford Fusion Energi™ is a commercial hybrid vehicle capable of electric drive and internal combustion power generation. This allows for travel over distances commonly unreachable via battery-only vehicles. Upon arrival at the test site, the internal combustion engine can be immediately overridden in order to prevent exhaust gases that may create interference. This platform also allows for close proximity spatial mapping in which the system maps following a grid, such as an industrial park or drilling site, thus providing concentrations of specific VOCs present in an entire region. Field testing for fracking and petroleum activities sampled atmosphere near a deep well injection site upon the Barnett shale region and the Eagle Ford shale play in central Texas. Urban environmental testing mapped Dallas, Texas, and yielded results that are relatable to active construction and areas of high traffic. The mass spectrometer itself may be powered by an onboard 110V supply, and provides an approximate distance of 25 miles of battery-only drive and analysis time during operational sampling.

For example, the portable system itself may be built in a rack mountable case and may contain a Transpector MPH Residual Gas Analyzer (RGA), as shown in FIG. 20. The method of mass analysis may be accomplished with a linear quadrupole and a Faraday cup/electron multiplier detector. The membrane inlet may be constructed on a 2.75 inch CF vacuum blank flange. Each set of feed-throughs is designed to accommodate 0.012 to inch inner diameter membrane. The membrane utilized for the experimental analysis described herein was a 0.020 inch Dow Corning Silastic (60-011-02, Helixmark, Carpinteria, Calif.). Vacuum may be maintained by a Pfeiffer (Asslar, Germany) MVP020-3DC diaphragm pump with a Pfeiffer SplitFlow 80 turbomolecular pump.

The inlet for atmospheric sampling may be provided through the immobile 'quarter glass' of the front passenger car door. The original glass was removed and an in-house custom made inlet scoop was installed into existing mountings, as shown in FIG. 20 at inset 2018. A diaphragm pump (UN84.3ANDC, KNF, Trenton, N.J.) may be used to provide constant flow of the sampled atmosphere. Furthermore, a small diaphragm pump (W311-11, Parker Hannifin, Mayfield Heights, Ohio) may be used to provide suction from main sample tubing to the inlet of the mass spectrometer.

The Ford Fusion Energi™ is a commercially available vehicle, modified for mounting of the instrumentation and equipment by removing the front passenger seat. Using the existing mountings for the seat, the system was mounted on in-house built 80-20 hardware. Further modifications concentrated on isolating vibrations. In an embodiment, an operator of the instrumentation may be seated in the rear passenger side seat of the vehicle and may utilize an installed workspace for analysis. In an embodiment, the entirety of the system may be powered from the batteries used for the electric motor in the car.

Data acquisition may be managed via a laptop or other computing device running a program configured to control the system to perform sampling operations. The program may be written in a suitable programming language, such as Python, and scripting may also be used to control the operations of the system during sampling. For example, a script may manage the mass scans from the spectrometer to perform repeated scanning and timestamping of the data. Instrumentation may be provided to capture other relevant data, such as location data and environmental data, and the instrumentation may be communicatively coupled to the computing device. For example, a primary microcontroller (e.g., an Arduino Mega 2560 (Strambino, Italy) may be attached to a device (e.g., a SparkFun Weather Shield (SparkFun Electronics, Niwot, Colo.)) configured to detect preliminary data regarding temperature, humidity, and pressure, and positioning data may be provided by a GPS receiver (e.g., Sparkfun Electronics GP-11571). The mass spectra and above data may be combined via timestamps to link a GPS location to a mass of interest.

Simulation of varying concentrations on analytes were accomplished using a KIN-TEK (Austin, Tex.) FlexStream Gas Standards Generator. This instrument is used to control emissions of trace concentration mixtures. Since concentration level is related to temperature, setting the FlexStream to a certain temperature resulted in a controlled and known concentration, FIG. 29. Intensities measured could then be translated into concentration levels (e.g., parts-per-billion). Furthermore, observations can be made concerning permeability of analytes through the membrane, noting how quickly analytes reach the mass analyzer and detector. Standard curves are created by exposing various concentrations to the membrane inlet. This yields a linear relation of detector intensity to concentration and allows for quantitative results.

Post data acquisition processing operates to combine the sample data and the position data, as well as environment data to present the observed samples as a gas stack model that visually depicts the dispersion of a molecule(s) of interest over the sampled area. In an embodiment, third party software may be utilized to present the dynamic reverse gas stack model overlaid on a map of the geographic area where the samples were obtained. For example, third party programs such as Google Earth and the National Oceanic and Atmospheric Agency (NOAA) and Environmental Protection Agency's (EPA) Areal Locations of Hazardous Atmospheres (ALOHA) software may be used to present the models in a user friendly format. The latitude and longitude obtained is used to locate where to plot the concentration data of the analyte. Each scan may be represented in Google Earth via a color coded circle (or another symbol), and a legend may be provided that correlates particular color coded symbols to concentration values or ranges, thereby allowing a user to view the distribution concentrations across the sampled area. It is note that in some embodiments color coding may not be used, and other techniques may be utilized to denote different observed concentrations. In an embodiment, the obtained values can be further processed and heat mapped to predict point source locations. In an embodiment, ALOHA software or a similar tool may be utilized in modeling the plumes from toxic chemicals, including those from predicted point source locations. Color coded zones of predicted toxicity can be calculated and illustrated in the map of the geographic area where the samples were obtained. This allows theoretical and experimentally obtained data to be overlaid.

Figure 30A:
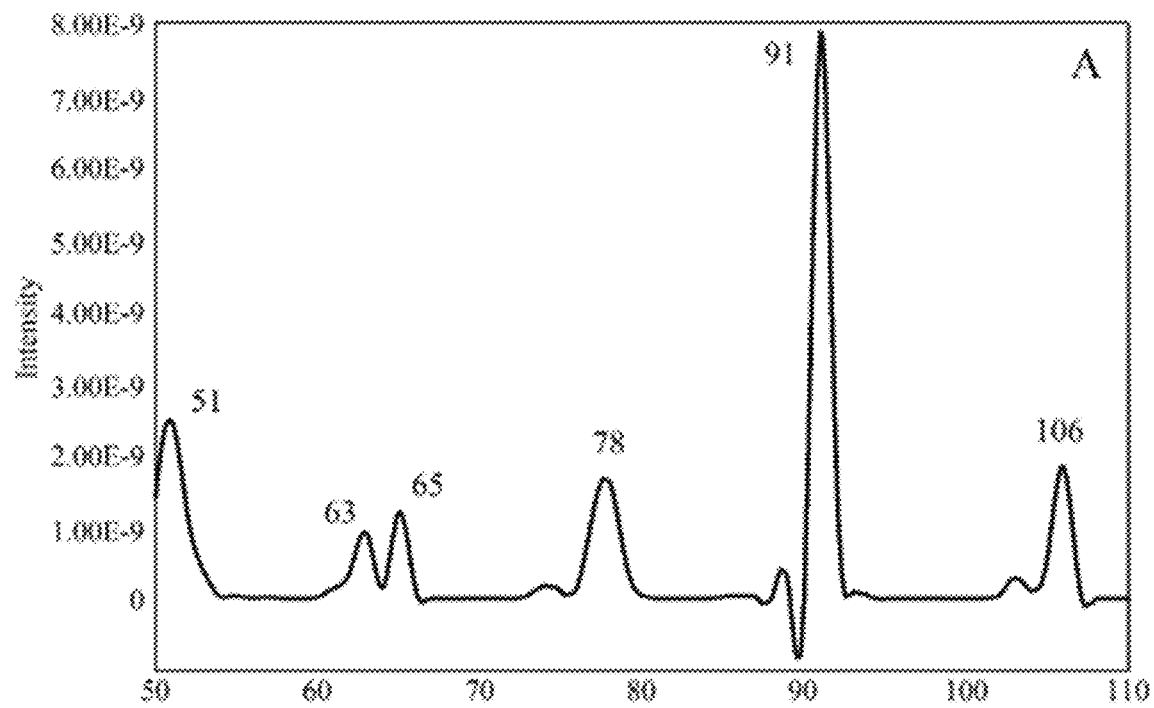
FIG. 30A shows mass spectra of benzene (78 m/z) toluene (91.92 m/z), and ethylbenzene (106 m/z) and xylene (106 m/z) atmospheric pollutants.
Figure 30B:
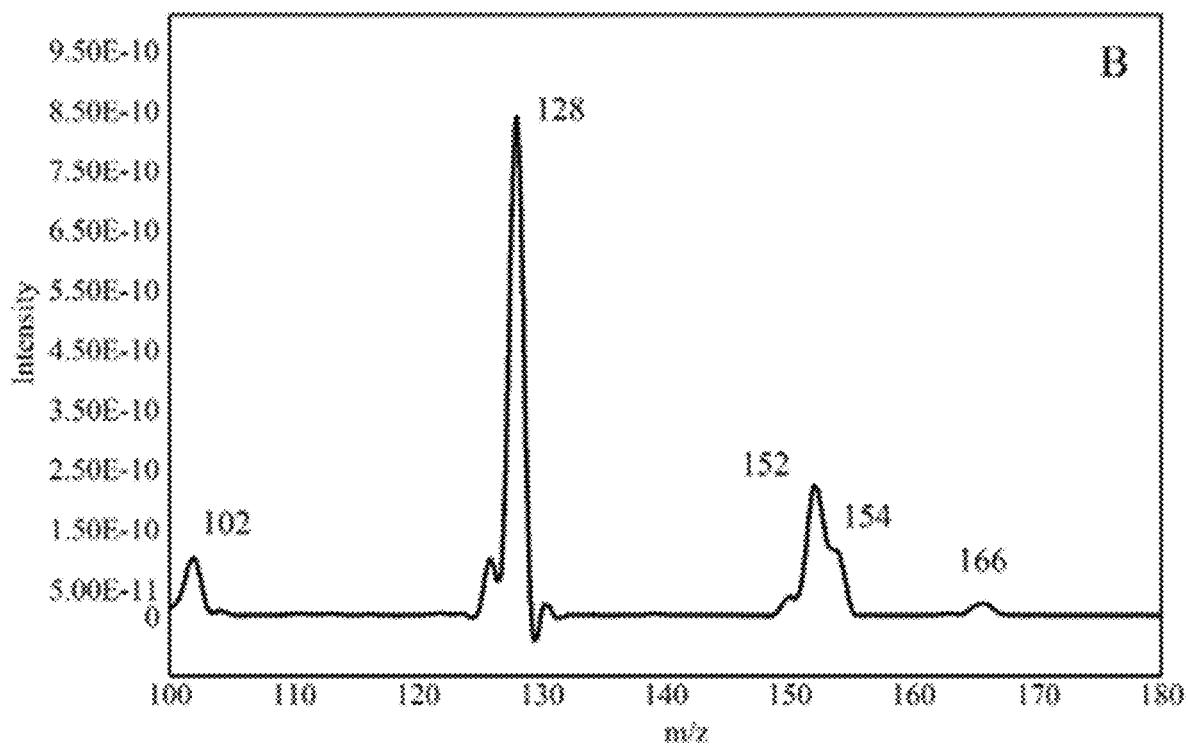
FIG. 30B shows mass spectra of PAH constituents naphthalene (128 m/z), acenaphthylene (152 m/z), acenaphthene (154 m/z), and fluorene (166 m/z)

The detection of volatile organic compounds (VOCs) is the primary intention of this system. Various laboratory prepared atmospheres are used before each data run to ensure permeability of the analytes of interest. FIGS. 30A-30B show the obtained spectra of two such samplings that are representative of the compounds that were anticipated to be detected. These test runs were performed with parts-per-billion quantities. Once the expected results are confirmed the unit may be deployed to the region of interest.

Figure 31:
FIG. 31 shows a GPS tagged spectra reflecting concentration of toluene throughout the city of Denton.

The study proceeded along approximately five miles of Denton, Tex. roads and interstate highway. Each scan of masses took approximately 2 seconds to accomplish. FIG. 31 depicts the concentration of toluene obtained from mobile analysis, which was plotted into Google Earth. The northern drive was through areas of ongoing construction and near an art building on the campus of the University of North Texas. The art building is of considerable interest as spray fixative is often used in close proximity to the building. This could account for the higher levels of toluene detected. Analysis that took place in less open areas (e.g. neighborhoods and heavily deciduous regions) had higher detected concentrations. Interstate highway analysis provided the lowest levels of detection, most likely due to the constant circulation of atmosphere.

Figure 32:
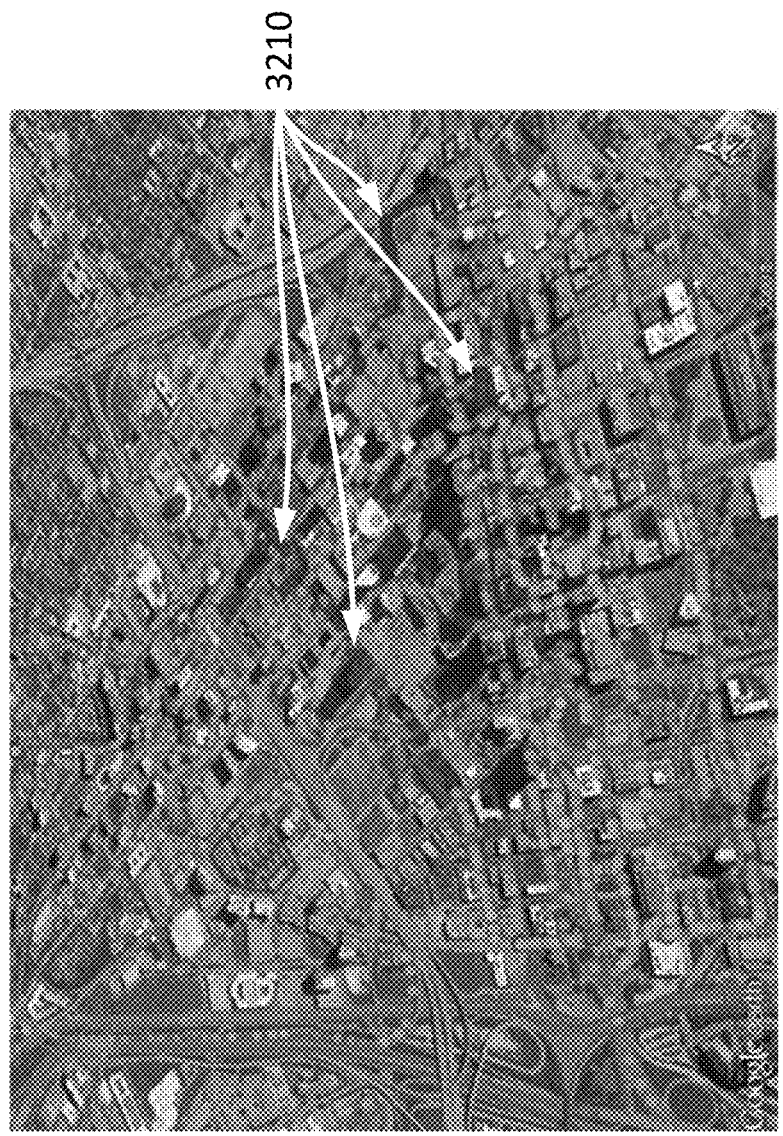
FIG. 32 shows benzene mapping data from MS analysis in the Dallas urban environment.

Urban detection observed the composition of BTEX, PAHs, and other VOCs in an urban environment. FIG. 32 illustrates concentrations of benzene. Of note are the areas depicted by the lines 3210, which indicate low concentrations. These areas are located within an area with little personal transportation; it is a central hub region of public transportation. As such, lower quantities of chemicals are present due to fewer emissions from internal combustion. Higher concentrations are located in the southern area of interest, where active construction is present, as well as high quantities of vehicular traffic.

Figure 33:
FIG. 33 shows benzene mapping data overlaid with an ALOHA dispersion model.

One intended application of this system is to provide information on deep well and hydraulic fracking. These are two notable local activities, and are the subject of nationwide environmental concerns. While regulatory matters constantly evolve and testing of sites is a necessary and expensive process, the system of embodiments, as described herein, has been demonstrated to be operable to map areas in close proximity to these operations. Direct access for close proximity testing is restricted in these drilling operations but neighboring areas within approximately 100 feet are possible; often times these areas are within residential and other highly populated areas. This site showed levels below Occupational Safety and Health Administration (OSHA) permissible exposure limits (PEL) of 1 ppm. Atmospheric factors influence how effluent will travel. The wind was traveling west to east, which is most notable from the plotted data in the figure. Combining the experimentally obtained data with the ALOHA software has allowed for an overlay of the theoretical plume from the point source location. The software does require a measure of the mass of effluent entering the atmosphere. This plot uses an arbitrary value of 1 gram per minute, this allowed for depiction of the capabilities of this mobile platform in conjunction with the ALOHA software. Unfortunately, access was not granted to obtain a direct measurement and data from operators of such sites is often not made available. Accurate weather data for the time of the analysis such as humidity, temperature, and windage was used for the calculations. FIG. 33 depicts spatial data of benzene in a neighborhood in close proximity to a deep well injection site upon the Barnett Shale.

This platform is especially useful as a regulatory aid and determination of conformance to protocols. At present, active drilling must be suspended to perform testing at a site. This incurs shutdown costs of approximately $100,000. Additionally, upon reactivation of petroleum pumping the well site usually does not reach previous output. This is an unfortunate side effect of testing, and presents a conflict with respect to maintaining output and profitability of a given site. Drive-by testing using embodiments of the present disclosure would allow for qualification of a given site without a need for shutdown. Air quality would be confirmed and quantitation of harmful chemicals obtained. This removes the corporate decision-making process of actively reducing a well site's profitability to ensure conformity to regulatory standards.

This mounted system has a number of applicable uses. Mapping roadways and regions where there is significant industrial activity that produces effluent yields excellent data sets in which conclusions such as plume tracking and quantity may be made. Performing such observations repeatedly would yield temporal associations, such as determining if a source is more active at certain times of day or while certain industrial processes of combinations of industrial processes are performed. Furthermore, the ability to integrate data obtained by the system with third party mapping software, such as Google Earth, allows for an unskilled operator to observe the data in a software environment familiar to most users. Further goals include working with petroleum companies to use the mobile system as an aid in proving safety of further drilling operations and with regulatory agencies. This system would be poised to provide quick spatial analysis and quantitation while operations remain ongoing, eliminating the need for site-wide shut down. Finally, a hybrid vehicle with electric-only drive capability during sampling removes interferences that would occur from traditional combustion engine mounted systems.

Figure 34:
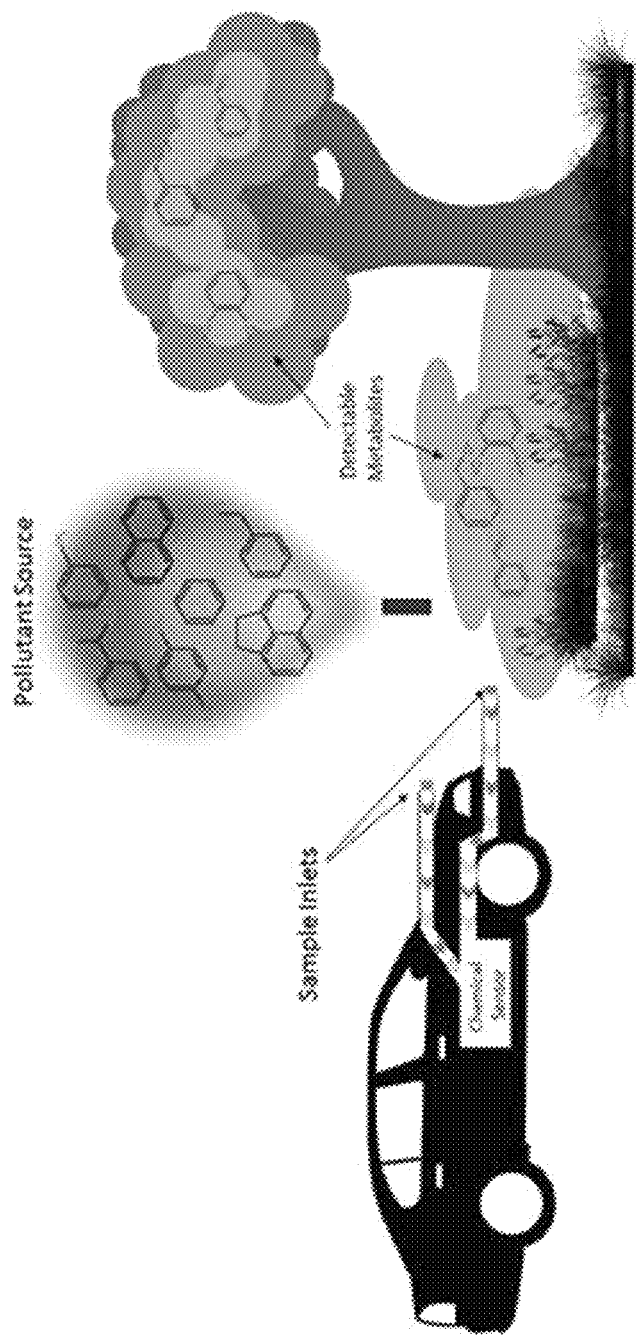
FIG. 34 shows an illustration of target molecule collection via a vehicular mass spectrometer.

Detection of chemicals released into the environment is routinely accomplished. Quantitative results and spatially relevant data sets yield excellent mapping data (FIG. 34). Extension of this technology would sense the metabolites from local flora and fauna. Ingestion of BTEX, PAHs, and other VOCs are metabolized by a common pathway between bacteria and fungi; this results in precursors used in the Krebs cycle. Deciduous organisms have a similar pathway. At present, detection of these known chemical constituents, especially catechol, would confirm the presence of pollutants in the environment and their active metabolism. Quantification of target chemicals resulting from cellular processes would determine the extent of pollution within a given region.

Example 3

Method for Reverse Atmospheric Dispersion Calculations to Locate Sources of Emission of Pollutants and Other Chemical Interests Innovative methods to monitor air quality is at the forefront of public health and environmental concerns constantly changing atmospheric contaminants, including increased instances of cancer. Current methodologies for air pollution monitoring include analytical devices that observe long term changes in atmospheric quality. Often analytical results are used to qualify given regions with higher or lower prevalence of air pollutants. Analytical models are often used to approximate and track plumes of pollutants from a point source and estimate their downwind concentrations. Chemical interests for dispersion modeling and analytical detection include, but are not limited to, polycyclic aromatic hydrocarbon emissions (PAHs) from unconventional petroleum drilling or effluent from clandestine drug manufacture. The unification of atmospheric dispersion modeling with field portable mass spectrometry datasets of the present invention may enable users to determine the location of a pollutant source.

Portable instrumentation has seen an escalation in the field of atmospheric monitoring. Increasing automation, small footprints, and lower power requirements highly regard the remote deployment of these systems. The capability of these systems to yield real time and rapid analysis best serve the requirements of continual atmospheric monitoring. Analytical systems designed for detection of organic compounds from atmospheric environments include gas chromatography-mass spectrometry (GC-MS), high pressure liquid chromatography-mass spectrometry (HPLC), infrared spectroscopy (IR), and ultraviolet-visible spectroscopy (UV-Vis). Results from these methods often target volatile organic compounds (VOCs) and specific alkylbenzene subsets including benzene, toluene, ethylbenzene, and xylenes (BTEX).

Specific methods that pertain to minimal sample extractive and preparative techniques for sampling atmospheric and aqueous pollutants have been developed. Solid phase micro extraction (SPME) methods extract chemical interests from atmospheric media and target VOCs subsequent analysis, such as by GC-MS. Aqueous sampling is accomplished by single drop micro-extraction (SDME), liquid phase micro-extraction (LPME), or direct aqueous injection (DAI). Dispersive vapor extraction (DVE) is used to extract volatile compounds from mixed gas samples. Although these methods yield good analytical results, they are spatially limited to the number of samples obtained for a given region and thereby yielding a small area of point source results.

Mass spectrometry has seen evolutionary development in the environmental monitoring field. Design needs for the development of portable mass spectrometry systems have been elucidated. Efforts to ruggedize and improve instrumentation for field use is of strong communal development. Field portable GC-MS systems have been developed for targeted chemical warfare agents in situ and other homeland security related applications. Underwater and aqueous sampling systems have been developed for targeted applications, including dissolved VOCs. Portable systems have seen targeted development for environmental pollutant analysis. These systems yield high quality mass spectrometry data for their given application and sampling region.

Temporally and spatially relevant measurements are becoming more mainstream. As analytical instrumentation continues to be refined for portability and remote operation these data sets provide snapshots of pollutants in a given area. For instance, changes in trace gas concentration in Himalayan regions over multiple months observed concentration changes that were attributable to monsoons and ongoing forest fires. Specialized units have been used for volcanic analysis, including UAV emplacement. Vehicular units have provided spatially and temporally relevant data sets, each with specialized targeted uses. Membrane inlet mass spectrometry (MIMS) is especially useful for such measurements, as the online continual sampling ability allows for active regional mapping.

Temporal and spatially relevant data sets from mobile systems provide experimental data that includes passive and diffusive sampling techniques and subsequent laboratory analysis. The application of geographic information systems (GIS) to the obtained data sets allows for heat mapping and other plotting methods. This includes the observation of air dispersion and changes in concentration as plumes travel. Real time measurements can be immediately inputted to air dispersion modeling whereby instrumentally-obtained datasets can be applied to modeling theories.

Air dispersion modeling approximates the diffusion of chemicals of interest, while taking into account various meteorological conditions. These models approximate dispersion from point source locations. Air dispersion modeling techniques and models are varied, but one of considerable interest is those based upon Gaussian dispersions. These models approximate dispersion across a given landscape and altitude, with results being a 'parts-per' concentration for a calculated endpoint. Oftentimes, these data sets are displayed as contour plots, summarizing multiple calculations for a dispersion over a given region.

Atmospheric dispersion models have seen various application. This includes coal power plant exhaust dispersion models in Japan targeting mercury levels. These models evaluated estimated regional atmospheric distribution of mercury, including background concentrations, and those contributed by the power plant. Volcanic ash dispersal has been approximated, exemplifying that air dispersion models apply to not only chemical constituents but also particulate matter. Such models also measure long distance transport of air pollutants. Furthermore, models account for varied regional qualities, including urban landscapes, and various atmospheric conditions.

Models have been the subject of many extensive experiments to validate their approximations to detected chemical concentration. Efforts to determine atmospheric dispersion parameters use experimental data to estimate standard deviation of Gaussian models, with good agreeance. Wind tunnels have been used to evaluate smoke stack plumes and improve on theoretical models. Smoke plumes from agricultural fires have been evaluated and tracked using ground-based LiDAR. In addition, the Environmental Protection Agency has developed tools for tracking feedlot emissions and industrial applications.

Embodiments of the present disclosure may use mobile mass spectrometry techniques to produce analytical data that represents a Gaussian dispersion downwind, which can be used to determine an approximate area where effluent is originating from. The dynamic reverse gas stack model with a Gaussian dispersion presented here is a method using reverse atmospheric dispersion calculations to locate sources of emission of pollutants and other chemical interests.

In embodiments where a chemical detection system according to embodiments of the present disclosure is mounted in a hybrid electric vehicle, the system may intake air through one of two locations, either an inlet where the quarter glass of the car was or through a modified intake where the fog lamp location was originally. The system may have a constant flow of air that provides sample for repeated analysis through a membrane inlet. Each mass scan is tagged with location data (e.g., a latitude and longitude obtained from a GPS system) that may be used for data visualization, as described above. In an embodiment, a model may be developed using the information associated with detected chemicals and the corresponding location data. In additional or alternative embodiments, a back-packable unit similar to the model used in the mobile unit may be used for small-scale testing (e.g., small scale testing as shown in FIG. 8). In embodiments, the system may be configured to integrate the data for presentation to a user via third party software, such as ALOHA and Google Earth software packages for, or custom/on-board software may be provided as part of the system and may be used to generate image data for presentation to the user.

The dispersion model used the Environmental Protection Agency's ALOHA software suite for validation purposes and to visualize hypothetical dispersed plumes. Atmospheric dispersion modeling uses Gaussian dispersions to approximate release and concentration downwind from a release source.

Thus, the device, analytical tools, methods, and models taught herein, independently or together, unify atmospheric dispersion and other meteorological phenomenon targeting chemical interests with a developed mobile mass spectrometer system. As mobile mass spectrometer and other chemical sensors are developed, applying a reverse atmospheric model to datasets will provide an additional avenue to determine how sources of pollution and activities that produce effluent behave. Furthermore, refinement of the examples and models shown herein is possible as real-time data points are obtained for a give analysis, and can be correlated to atmospheric conditions. Rather than using air sampling canisters and tracer gases for atmospheric modeling, actual sources of pollution can be modeled. Analysis in the environment lends itself to rapid sampling, as more data points for a given region hone the Gaussian dispersion. Using the present invention, the dispersion of chemicals in a variety of terrains, meteorological conditions, and emission characteristics allows for determining point source location.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference in their entirety to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A system comprising:
   a plurality of molecule detectors, wherein each molecule detector of the plurality of molecule detectors is disposed at a different location within a geographic area and configured to generate information representative of one or more target molecules present in samples of an environment,
   a reverse gas stack modelling device communicatively coupled to the plurality of molecule detectors, the reverse gas stack modelling device comprising:
      a memory; and
      one or more processors communicatively coupled to the memory and configured to:
         obtain location information representative of the different locations corresponding to the plurality of molecule detectors;
         receive, from the plurality of molecule detectors, the information representative of the one or more target molecules present in the samples;
         determine a dynamic reverse gas stack model for the one or more target molecules by back-calculating a dispersion of the one or more target molecules from the different locations corresponding to the plurality of molecule detectors to a location for a source or effluent for the one or more molecules, the information representative of the one or more molecules present in the samples and the location information, wherein the dynamic reverse gas stack model is configured to visually represent an atmospheric, Gaussian dispersion of a plume corresponding to the one or more molecules, wherein the dynamic reverse gas stack model is determined without using characteristics associated with the source or effluent for the one or more molecules as independent variables, and wherein the characteristics associated with the source or effluent comprises one or more of the location for the source or effluent, elevation of the source or effluent, and emission rate of the source or effluent; and
         predict the location for the source or effluent for the one or more target molecules based on the dynamic reverse gas stack model.

2. The system of claim 1, wherein the geographic area comprises a city or portion of the city.

3. The system of claim 1, wherein the geographic area comprises a refinery, a chemical production facility, an oil production facility, an underground area, or a building.

4. The system of claim 1, wherein the plurality of molecule detectors are permanently installed at the different locations.

5. The system of claim 1, wherein the plurality of molecule detectors are temporarily installed at the different locations.

6. The system of claim 1, wherein the location information is obtained from the memory of the reverse gas stack modelling device.

7. The system of claim 1, wherein each molecule detector of the plurality of molecule detectors comprises a Raman spectrometer, an infrared (IR) spectrometer, a chemical sensor, or a mass spectrometer.

8. The system of claim 1, wherein the one or more processors are configured to obtain additional data from one or more data sources, and wherein the predicted location of the source or effluent is determined based on the additional data.

9. The system of claim 8, wherein the additional data comprises wind speed data, wind direction data, temperature data, barometric pressure data, infrastructure data, or a combination thereof.

10. The system of claim 1, wherein each molecule detector of the plurality of molecule detectors comprises a sampling pump configured to increase a sampling volume by increasing throughput of the molecule detector.

11. The system of claim 1, wherein each molecule detector of the plurality of molecule detectors comprises specific detectors for one or more types of molecules associated with chemicals comprising polycyclic aromatic hydrocarbon emissions (PAHs), benzene, alkyl benzene, chlorobenzene, or trichlorobenzene, isopropylbenzene, ethylbenzene, cyclohexanone, xylene, p-cymene, hydrocarbons produced by oil and gas exploration or extraction, methane, ethane, propane, butane, pentane, hexane, toluene, trichloroethene, chloroform, tetrachloroethane, 1,1,1-trichloroethane, 1,1,2,2-tetrachloroethane, xylene, carbon tetrachloride, 1,1-dichloroethane, and 1,2-dichloroethane.

12. The system of claim 1, wherein the plurality of molecule detectors are attached to buildings, street lamps, signs, subway systems, sewer systems, or other infrastructure within the geographic area.

13. A method for detecting a source for one or more molecules comprising:
   obtaining, by one or more processors, location information identifying locations of a plurality of molecule detectors within a geographic area, wherein each molecule detector of the plurality of molecule detectors is configured to generate information representative of one or more target molecules present in samples of an environment;
   receiving, by the one or more processors from the plurality of molecule detectors, the information representative of the molecules present in the samples;
   determining, by the one or more processors, a dynamic reverse gas stack model for the one or more target molecules by back-calculating a dispersion of the one or more target molecules from the locations corresponding to the plurality of molecule detectors to a location for a source or effluent for the one or more molecules, the information representative of the one or more molecules present in the samples and the location information, wherein the dynamic reverse gas stack model is configured to visually represent an atmospheric, Gaussian dispersion of a plume corresponding to the one or more molecules, wherein the dynamic reverse gas stack model is determined without using characteristics associated with the source or effluent for the one or more molecules as independent variables, and wherein the characteristics associated with the source or effluent comprises one or more of the location for the source or effluent, elevation of the source or effluent, and emission rate of the source or effluent; and predicting, by the one or more processors, the location for the source or effluent for the one or more target molecules based on the dynamic reverse gas stack model.

14. The method of claim 13, wherein the geographic area comprises a city or portion of the city.

15. The method of claim 13, wherein the geographic area comprises a refinery, a chemical production facility, an oil production facility, an underground area, or a building.

16. The method of claim 13, wherein the plurality of molecule detectors are permanently or temporarily installed within the geographic area.

17. The method of claim 13, wherein each molecule detector of the plurality of molecule detectors comprises a Raman spectrometer, an infrared (IR) spectrometer, a chemical sensor, or a mass spectrometer.

18. The method of claim 13, wherein the one or more processors are configured to obtain additional data from one or more data sources, and wherein the predicted location of the source or effluent is determined based on the additional data, wherein the additional data comprises wind speed data, wind direction data, temperature data, barometric pressure data, infrastructure data, or a combination thereof.

19. The method of claim 13, wherein each molecule detector of the plurality of molecule detectors comprises specific detectors for one or more types of molecules associated with chemicals comprising polycyclic aromatic hydrocarbon emissions (PAHs), benzene, alkyl benzene, chlorobenzene, or trichlorobenzene, isopropylbenzene, ethylbenzene, cyclohexanone, xylene, p-cymene, hydrocarbons produced by oil and gas exploration or extraction, methane, ethane, propane, butane, pentane, hexane, toluene, trichloroethene, chloroform, tetrachloroethane, 1,1,1-trichloroethane, 1,1,2,2-tetrachloroethane, xylene, carbon tetrachloride, 1,1-dichloroethane, and 1,2-dichloroethane.

20. The method of claim 13, further comprising generating an additional reverse gas stack model using additional information obtained by a mobile molecule detection platform in response to detecting one or more target molecules based on the samples obtained from the plurality of molecule detectors.

* * * * *